(12) United States Patent
Lee

(10) Patent No.: US 12,257,418 B2
(45) Date of Patent: Mar. 25, 2025

(54) INFUSION PUMP CONTROL METHOD, INFUSION PUMP AND TUBE CASSETTE FOR FLUID DELIVERY

(71) Applicant: EPIC MEDICAL PTE LTD, Singapore (SG)

(72) Inventor: Freddie Eng Hwee Lee, Singapore (SG)

(73) Assignee: EPIC MEDICAL PTE. LTD., Singapore (SG)

( * ) Notice: Subject to any disclaimer, the term of this patent is extended or adjusted under 35 U.S.C. 154(b) by 1091 days.

(21) Appl. No.: 16/682,843

(22) Filed: Nov. 13, 2019

(65) Prior Publication Data

US 2020/0147303 A1    May 14, 2020

Related U.S. Application Data

(60) Provisional application No. 62/760,136, filed on Nov. 13, 2018.

(51) Int. Cl.
*A61M 5/168* (2006.01)
*A61M 5/14* (2006.01)
(Continued)

(52) U.S. Cl.
CPC .... *A61M 5/16877* (2013.01); *A61M 5/14232* (2013.01); *A61M 5/16831* (2013.01);
(Continued)

(58) Field of Classification Search
CPC .......... A61M 5/16877; A61M 5/14232; A61M 5/172; A61M 2005/1402; A61M 2205/12;
(Continued)

(56) References Cited

U.S. PATENT DOCUMENTS 4,838,856 A    6/1989  Mulreany et al.
5,078,683 A    1/1992  Sancoff et al.
(Continued)

FOREIGN PATENT DOCUMENTS

WO    WO 2008/106589 A2    9/2008
WO    WO 2016/089775 A1    6/2016

OTHER PUBLICATIONS

European Patent Application No. 19209003.3; Extended Search Report; dated Feb. 12, 2020; 11 pages.

*Primary Examiner* — Lauren P Farrar
(74) *Attorney, Agent, or Firm* — BakerHostetler

(57) ABSTRACT

A method reads fluid delivery specification from a tube cassette and carry out infusion upon acceptance of the fluid delivery specification. An infusion pump comprises a housing having a compartment into which a tube cassette is receivable; a controller; a label reader disposed in the housing, accessible to the cassette compartment and coupled to the controller; a user interface disposed in the housing and coupled to the controller, the user interface including a screen, a first operator and a second operator coupled to the user interface. The first and second operators provide a first response signal to the controller for a prompt displayed on the screen and a second response signal to the controller for a request displayed on the screen. A tube cassette has a label bearing fluid delivery specification and allows fluid infusion upon the specification in the label matching parameters stored in an infusion pump.

20 Claims, 65 Drawing Sheets

(51) Int. Cl.
*A61M 5/142* (2006.01)
*A61M 5/172* (2006.01)
*A61M 5/36* (2006.01)

(52) U.S. Cl.
CPC ............ *A61M 5/172* (2013.01); *A61M 5/365* (2013.01); *A61M 2005/1402* (2013.01); *A61M 2005/16863* (2013.01); *A61M 2205/12* (2013.01); *A61M 2205/18* (2013.01); *A61M 2205/3331* (2013.01); *A61M 2205/3379* (2013.01); *A61M 2205/50* (2013.01); *A61M 2205/502* (2013.01); *A61M 2205/505* (2013.01); *A61M 2205/52* (2013.01); *A61M 2205/584* (2013.01); *A61M 2205/6063* (2013.01); *A61M 2205/6072* (2013.01); *A61M 2205/8206* (2013.01)

(58) Field of Classification Search
CPC ...... A61M 2205/3379; A61M 2205/50; A61M 2205/502; A61M 2205/52; A61M 2205/6063; A61M 1/14; A61M 1/28
See application file for complete search history.

(56) References Cited

U.S. PATENT DOCUMENTS

| | | | | |
|---|---|---|---|---|
| 5,317,506 A | * | 5/1994 | Coutre | A61M 5/16831 |
| | | | | 128/DIG. 13 |
| 5,505,696 A | * | 4/1996 | Miki | A61M 5/365 |
| | | | | 604/67 |
| 6,106,498 A | | 8/2000 | Friedli et al. | |
| 2004/0051368 A1 | | 3/2004 | Caputo et al. | |
| 2005/0209563 A1 | | 9/2005 | Hopping et al. | |
| 2011/0313395 A1 | * | 12/2011 | Krulevitch | A61M 5/24 |
| | | | | 604/82 |
| 2013/0191770 A1 | | 7/2013 | Bartz et al. | |
| 2016/0008529 A1 | * | 1/2016 | Hoffman | A61M 1/28 |
| | | | | 604/28 |
| 2017/0028110 A1 | * | 2/2017 | Smith | A61M 1/73 |
| 2021/0162115 A1 | * | 6/2021 | Surine | A61M 5/142 |

* cited by examiner

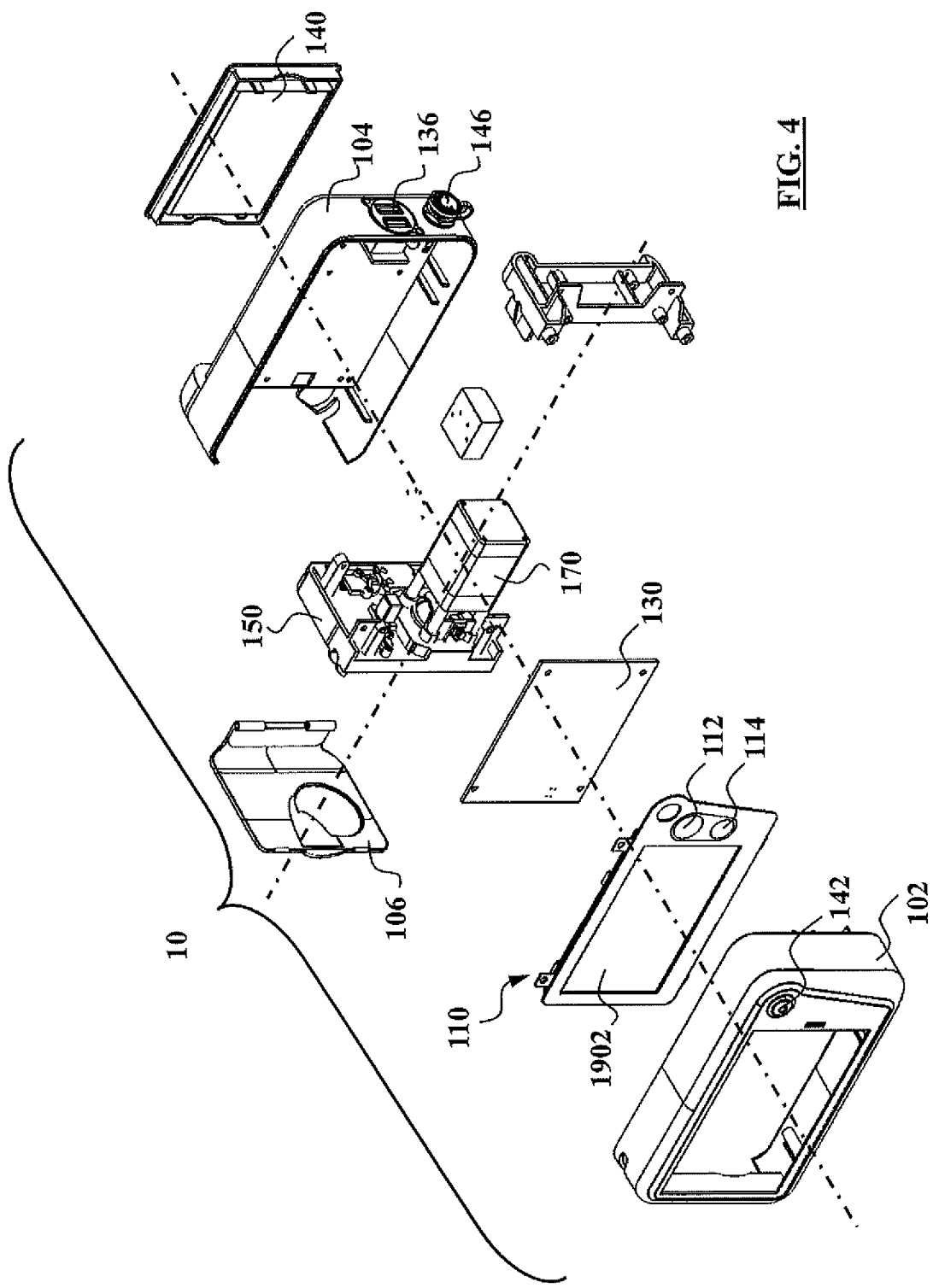

INFUSION PUMP CONTROL METHOD, INFUSION PUMP AND TUBE CASSETTE FOR FLUID DELIVERY

CROSS-REFERENCE TO RELATED APPLICATIONS

This application claims priority to U.S. Patent Application Ser. No. 62/760,136 filed Nov. 13, 2018, the disclosure of which is hereby incorporated by reference as if set forth in its entirety herein.

TECHNICAL FIELD

Disclosed herein relates to a medical apparatus and control method and a tube cassette and particularly to a medical infusion pump control method, an infusion pump and a tube cassette for use with an infusion pump for fluid delivery.

BACKGROUND

Infusion pumps are used in medical applications for delivering fluid medicine under precise and slow flow rate. Conventional infusion pumps require user input via keyboard or touch screen during initialization and setup. Amongst critical parameter inputs, flow rate required for medication delivery is provided by manual input. Infusion pumps with such user interface results in the control being dependent on user inputs are vulnerable to human error. Human errors are the most dominant source of adverse events in the use of infusion pumps. It is relatively easy to make mistakes in decimal inputs that lead to infusion flow rates that are multiples of the intended flow rate. It is therefore desirable to provide an infusion pump and control method to reduce the likelihood of human errors in operating the infusion pump

SUMMARY

In the disclosed invention the use of barcodes (or any form of a code system) on the infusion administration line, in this instance configured as a tube cassette, offers a means of separating the control inputs from the pump itself. This not only reduces risks associated with human errors but also prevents the therapy given to patients at home from inappropriate intervention as the pump is prevented from receiving unsafe inputs via the user interface.

In one aspect, the present disclosure provides an infusion pump control method, which comprises obtaining an information of a fluid delivery specification from a tube cassette loaded to the infusion pump; displaying the information of the fluid delivery specification at a user interface of the infusion pump; receiving a first response signal via the user interface; and setting the infusion pump according to the first response signal.

In one embodiment, obtaining an information of a fluid delivery specification from a tube cassette comprises scanning an optical label borne on the tube cassette, wherein the optical label is embedded with a code corresponding to the fluid delivery specification.

Preferably, the fluid delivery specification includes a flow rate under which the fluid delivery is to be carried out, the first response signal includes one of an affirmative indication of accepting the flow rate and a negative indication of rejecting the flow rate.

Preferably, upon the first response signal received being the affirmative indication, operating the infusion pump includes configuring the fluid delivery under the flow rate accepted.

Preferably, the fluid delivery specification includes a Volume-To-Be Infused (VTBI) under which the fluid delivery is to be carried out, the first response signal includes one of an affirmative indication of accepting the VTBI and a negative indication of revising the VTBI.

Preferably, upon the first response signal received being the affirmative indication, operating the infusion pump includes configuring the fluid delivery under the VTBI accepted.

Preferably, the method further comprises displaying at the interface a request for a priming and receiving a second response signal via the user interface for the request.

Preferably, the second response signal includes one of an affirmative indication of carrying out the priming and a negative indication of skipping the priming.

Preferably, wherein upon the second response signal being the affirmative indication, operating the infusion pump includes carrying out the fluid delivery under the flow rate accepted and the VTBI accepted after the priming.

Preferably, upon the second response signal being the negative indication, operating the infusion pump includes carrying out the fluid delivery under the flow rate accepted and the VTBI accepted without the priming.

Alternatively, upon the first response signal received being the negative indication, operating the infusion pump includes enabling input of a customized VTBI at the interface, and configuring the fluid delivery under the customized VTBI.

Preferably, the method further comprises prompting at the interface a request for a priming and receiving a second response signal via the user interface for the request.

Preferably, the second response signal includes one of an affirmative indication of carrying out the priming and a negative indication of skipping the priming. Upon the second response signal being the affirmative indication, operating the infusion pump includes carrying out the fluid delivery under the flow rate accepted and the customized VTBI after the priming.

Alternatively, upon the second response signal being the negative indication, operating the infusion pump includes carrying out the fluid delivery under the flow rate accepted and the customized VTBI without the priming.

Preferably, upon the first response signal received being the negative indication, operating the infusion pump includes awaiting the tube cassette to be replaced and loaded to the infusion pump.

Preferably, the method further comprises displaying at the user interface a notice of replacing the tube cassette.

Preferably, the method further comprises displaying at the user interface a notice of replacing the tube cassette.

Preferably, the method further comprises checking the fluid delivery specification against a predetermined set of parameters stored in the infusion pump, wherein upon the fluid delivery specification matching all the predetermined set of parameters, operating the infusion pump includes carrying out the fluid delivery according to the fluid delivery specification.

The predetermined set of parameters may include a flow rate, a Volume-To-Be Infused (VTBI), a date, a time and a sequence ID under each of which the fluid delivery is to be carried out.

Preferably, the method further comprise checking the fluid delivery specification against a predetermined set of parameters stored in the infusion pump, wherein upon the fluid delivery specification mismatching at least one of the predetermined set of parameters, operating the infusion pump includes awaiting the tube cassette to be replaced and loaded to the infusion pump.

Preferably, the predetermined set of parameters include a flow rate, a Volume-To-Be Infused (VTBI), a date, a time and a sequence ID under each of which the fluid delivery is to be carried out.

According to another aspect, the present disclosure provides an infusion pump including a housing having a cassette compartment into which a tube cassette is receivable, a controller disposed in the housing, a label reader disposed in the housing, accessible to the cassette compartment and coupled to the controller, and a user interface disposed in the housing and coupled to the controller. The user interface includes a screen a first operator and a second operator coupled to the user interface. The first operator and the second operator are configured to provide a first response signal to the controller for a prompt displayed on the screen and a second response signal to the controller for a request displayed on the screen.

Preferably, the label reader is to scan an optical label borne on a tube cassette loaded into the cassette compartment to decode a fluid delivery specification from the optical label and transmit the fluid delivery specification to the controller.

Preferably, the fluid delivery specification includes a flow rate under which a fluid delivery is to be carried out. The first response signal includes one of an affirmative indication upon execution of the first operator for accepting the flow rate and a negative indication upon execution of the second operator for rejecting the flow rate.

Preferably, the infusion pump is configured to carry out a fluid delivery under a flow rate accepted upon the controller receiving the affirmative indication by execution of the first operator.

Preferably, the fluid delivery specification includes a Volume-To-Be Infused (VTBI) under which the fluid delivery is to be carried out, the first response signal includes one of an affirmative indication upon execution of the first operator for accepting the VTBI and a negative indication upon execution of the second operator for revising the VTBI.

Preferably, the infusion pump is configured to carry out a fluid delivery under the VTBI accepted upon the controller receiving the affirmative indication by execution of the first operator.

Preferably, the request is for priming the infusion pump, and the infusion pump is configured to carry out the priming upon the second response signal being generated by execution of the first operator and carry out the fluid delivery under the flow rate accepted and the VTBI accepted.

Preferably, the request is for priming the infusion pump, and the infusion pump is configured to skip the priming upon the second response signal being generated by execution of the second operator and carry out the fluid delivery under the flow rate accepted and the VTBI accepted.

Preferably, the infusion pump is configured to enable input from the user interface a customized VTBI upon the controller receiving the negative indication by execution of the second operator.

Preferably, the request is for priming the infusion pump, and the infusion pump is configured to carry out the priming upon the second response signal being generated by execution of the first operator and carry out the fluid delivery under the flow rate accepted and the customized VTBI.

Alternatively, the request is for priming the infusion pump, and the infusion pump is configured to skip the priming upon the second response signal being generated by execution of the second operator and carry out the fluid delivery under the flow rate accepted and the customized VTBI.

Preferably, the infusion pump is configured to be suspended upon the controller receiving the negative indication by execution of the second operator.

Preferably, the infusion pump is configured to display on the screen a notice of replacing the tube cassette.

Preferably, the infusion pump further comprises a memory device coupled to the controller, the memory device includes a predetermined set of infusion parameters stored therein, wherein the controller is configured to check the fluid delivery specification against the predetermined set of infusion parameters.

Preferably, the infusion pump is configured to carry out an infusion upon the fluid delivery specification matching all the predetermined set of parameters.

Preferably, the predetermined set of parameters include a flow rate, a Volume-To-Be Infused (VTBI), a date, a time and a sequence ID under each of which the fluid delivery is to be carried out.

Preferably, infusion pump is configured to refuse an infusion upon the fluid delivery specification mismatching at least one of the predetermined set of parameters.

Preferably, the predetermined set of parameters include a flow rate, a Volume-To-Be Infused (VTBI), a date, a time and a sequence ID under each of which the fluid delivery is to be carried out.

According to a further aspect, the present disclosure provides a tube cassette for use with a n infusion pump for medication fluid delivery, the tube cassette includes a housing engageable to an infusion pump, a fluid channel fixedly arranged in the housing and an actuator movably coupled to the housing and abuts against the fluid channel to form a deformed portion on the fluid channel, wherein movement of the actuator carries the deformed portion downstream the fluid channel to expel a fluid out of the fluid channel.

Preferably, the fluid channel having an inlet fixed to a first edge of the housing and an outlet fixed to a second edge of housing, wherein the inlet and the outlet are distinctively oriented from the housing, wherein movement of the actuator carries the deformed portion downstream the fluid channel to expel the fluid out of the outlet of the fluid channel.

Preferably, the fluid channel having an executing segment between the inlet and the outlet and arranged to surround the actuator, wherein the actuator is rotatably coupled to the housing and rotatable relative to the housing along a path having a first section separating from the executing segment and a second section intersecting the executing segment.

Preferably, the actuator comprises a cylindrical driving member rotatably coupled to the housing about a center axis, a set of cylindrical rollers disposed in the housing and rotatably engaged to the cylindrical driving member, wherein at least one of the set of cylindrical rollers is movable along the path to circulate from an idle position within the first section, to a first working position entering the second section, to a second working position departing the second section and back to the idle position.

Preferably, the actuator comprises at least two cylindrical rollers evenly arranged surrounding the cylindrical driving member, wherein at least one of the cylindrical rollers is brought into abutment with the executing segment at a given moment during a rotational movement of the actuator.

Preferably, the executing segment is arranged to overlap at least two third of the full circular movement path of the at least two cylindrical rollers.

Preferably, the infusion pump further comprises a label attached to the housing and readable by the infusion pump, wherein the label has embedded therein a code corresponding to a fluid delivery specification of the tube cassette.

Preferably, the fluid delivery specification includes a flow rate, a Volume-To-Be Infused (VTBI), a date, a time and a sequence ID under each of which the fluid delivery is to be carried out.

Preferably, the label is programmable by a computer such that an infusion pump to which the tube cassette is loaded carries out an infusion according to the fluid delivery specification decoded from the label.

These and other aspects and advantages of the present application will become apparent from the following detailed description, illustrating by way of example the technical solution of the present application.

BRIEF DESCRIPTION OF THE DRAWINGS

Embodiments of the present application are disclosed hereinafter with reference to the drawings, in which:

FIG. 4 is an exploded front view of the infusion pump shown in FIG. 1;

DETAILED DESCRIPTION

Figure 1:
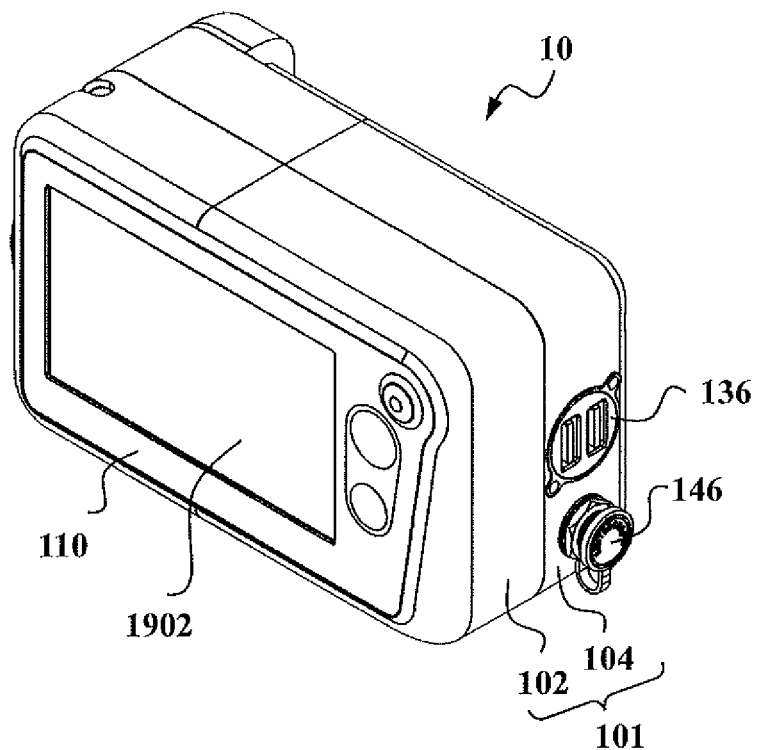
FIG. 1 is a perspective view of an infusion pump according to one embodiment of the present invention.
Figure 2:
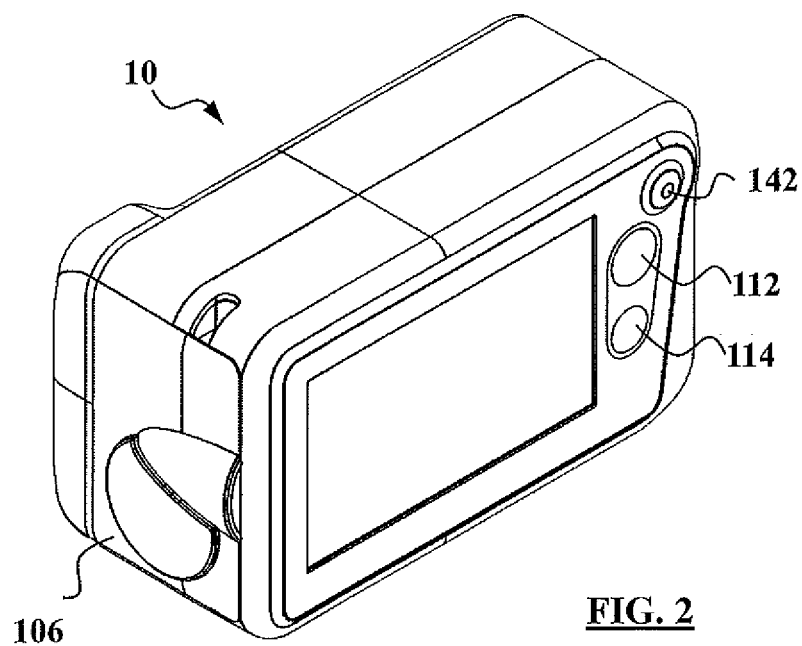
FIG. 2 is a perspective left view of the infusion pump shown in FIG. 1.
Figure 3A:
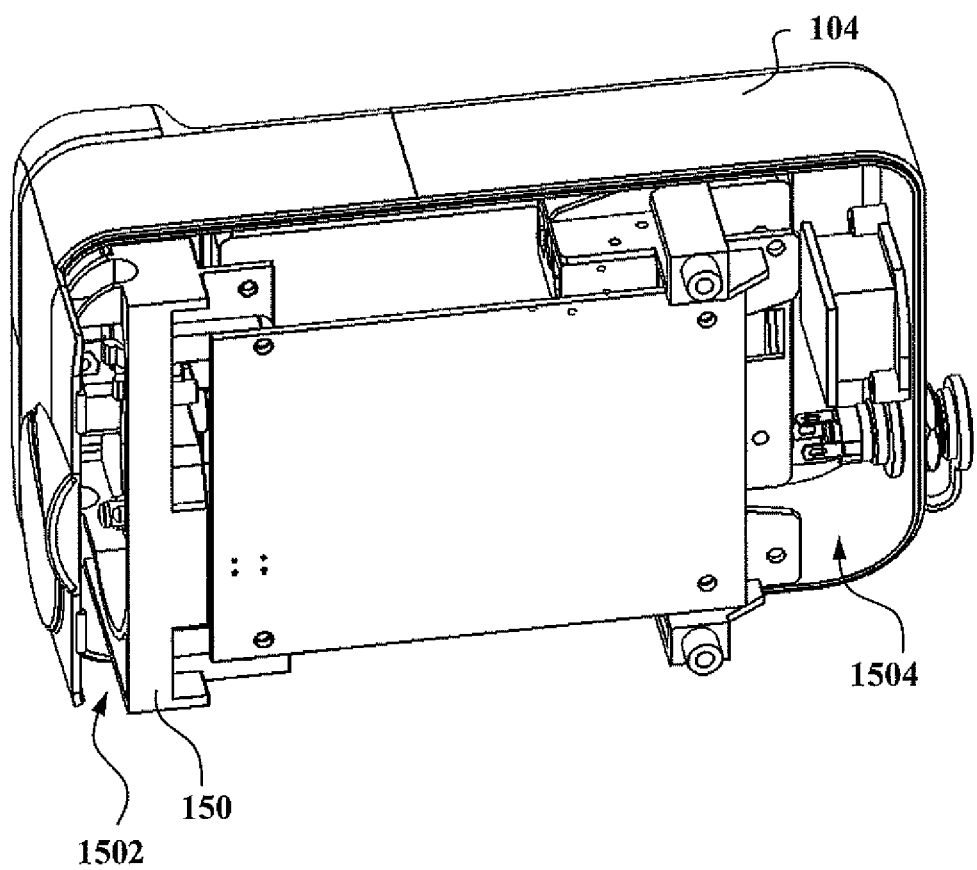
FIG. 3A is a perspective partial view of the infusion pump shown in FIG. 1 in which some of components are omitted.
Figure 3B:
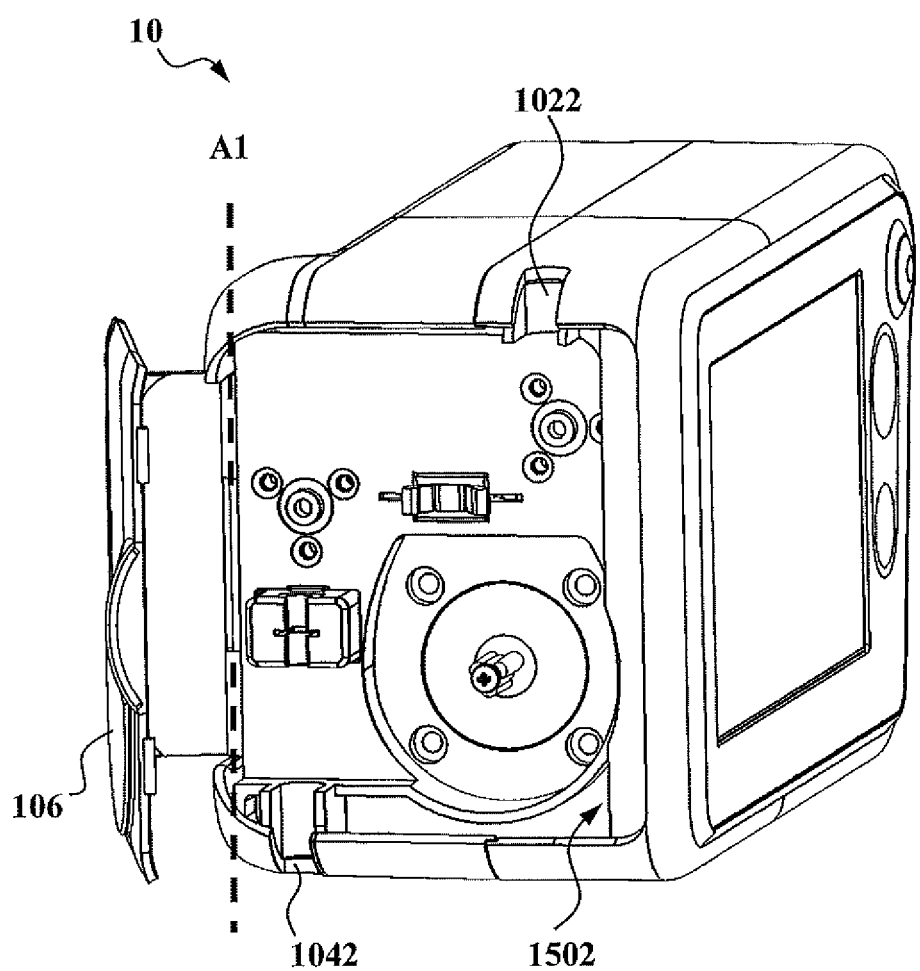
FIG. 3B is a perspective left view of the infusion pump shown in FIG. 1 with a cassette compartment door opened.
Figure 3C:
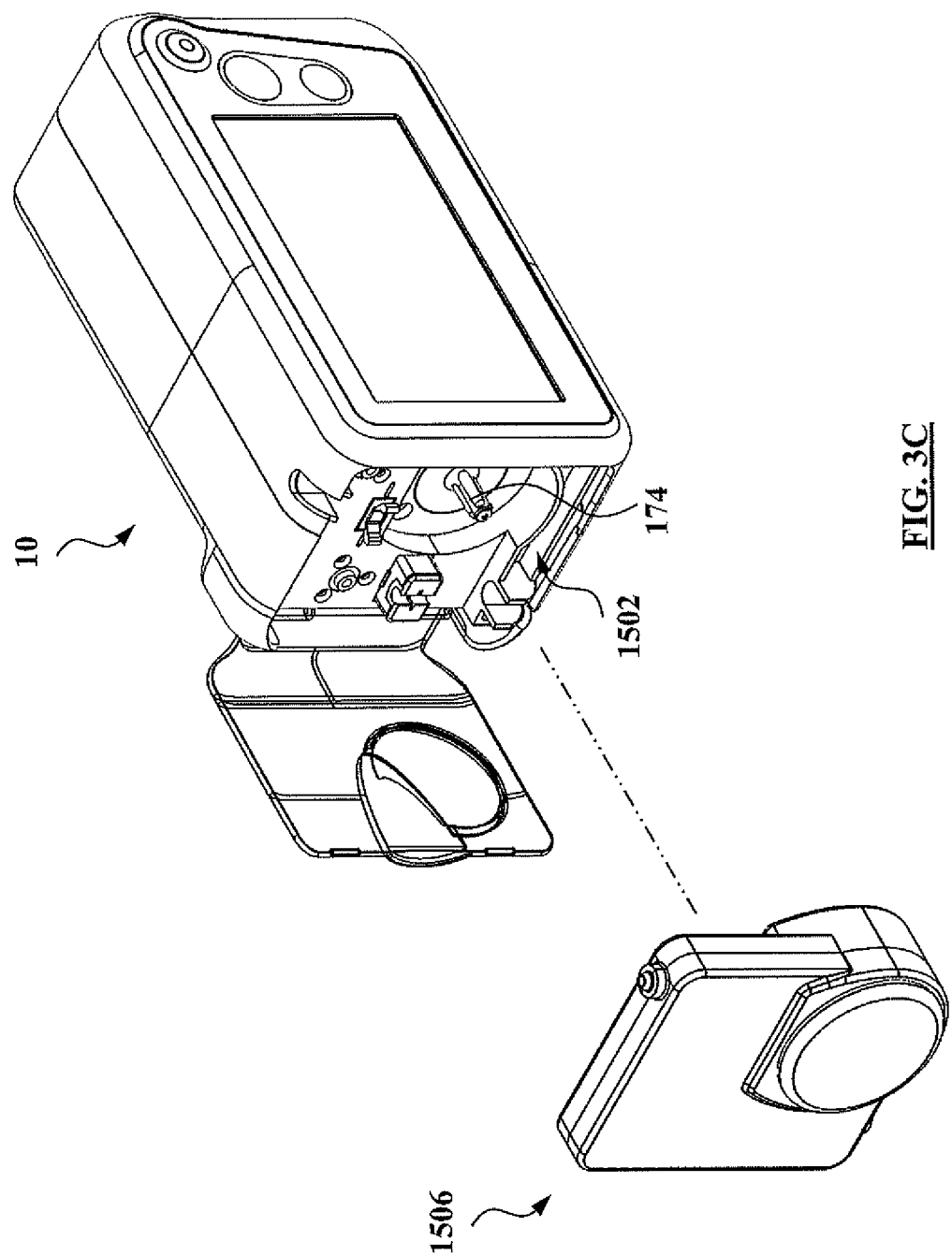
FIG. 3C is a perspective left view of the infusion pump shown in FIG. 1 and a tube cassette to be loaded into the cassette compartment.
Figure 3D:
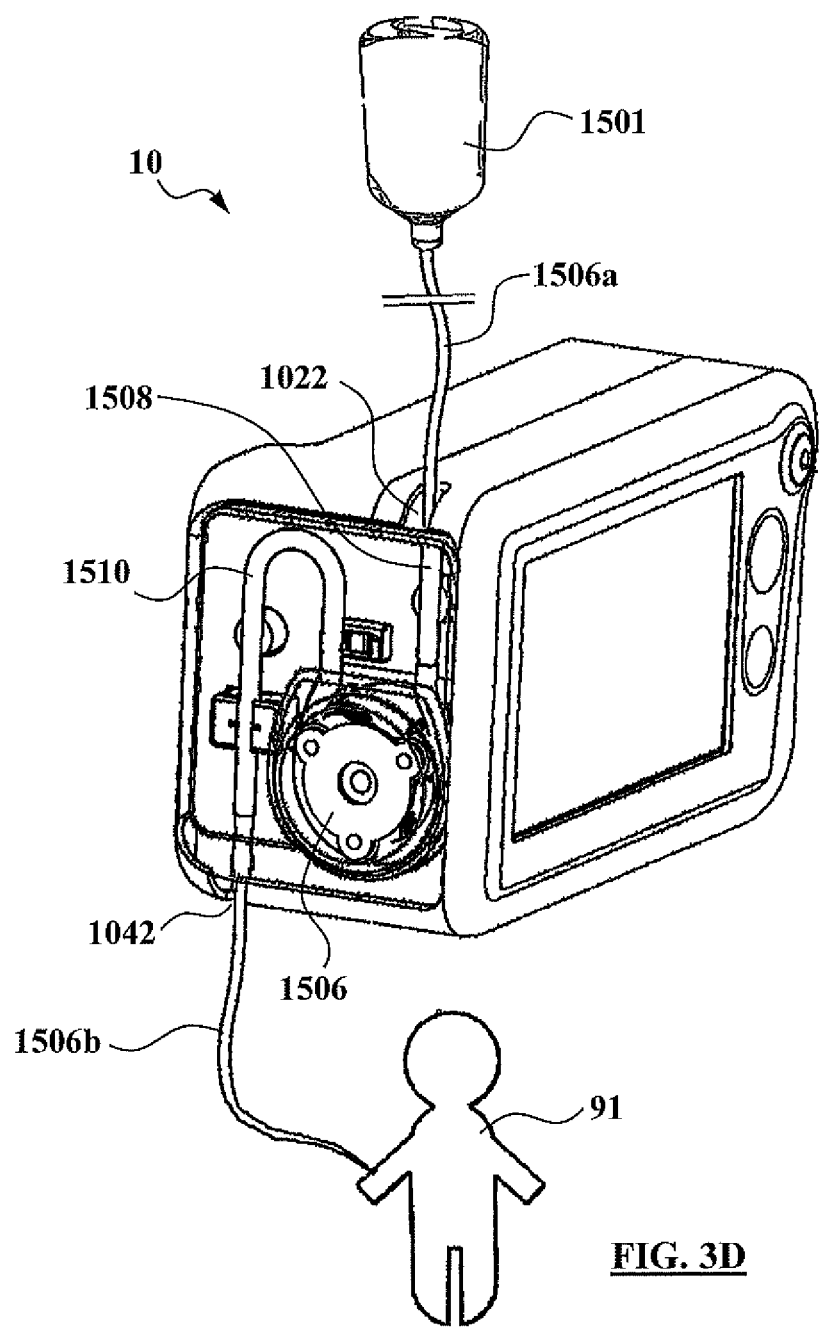
FIG. 3D is a perspective left view of the infusion pump shown in FIG. 1 with a tube cassette loaded into the cassette compartment.
Figure 5:
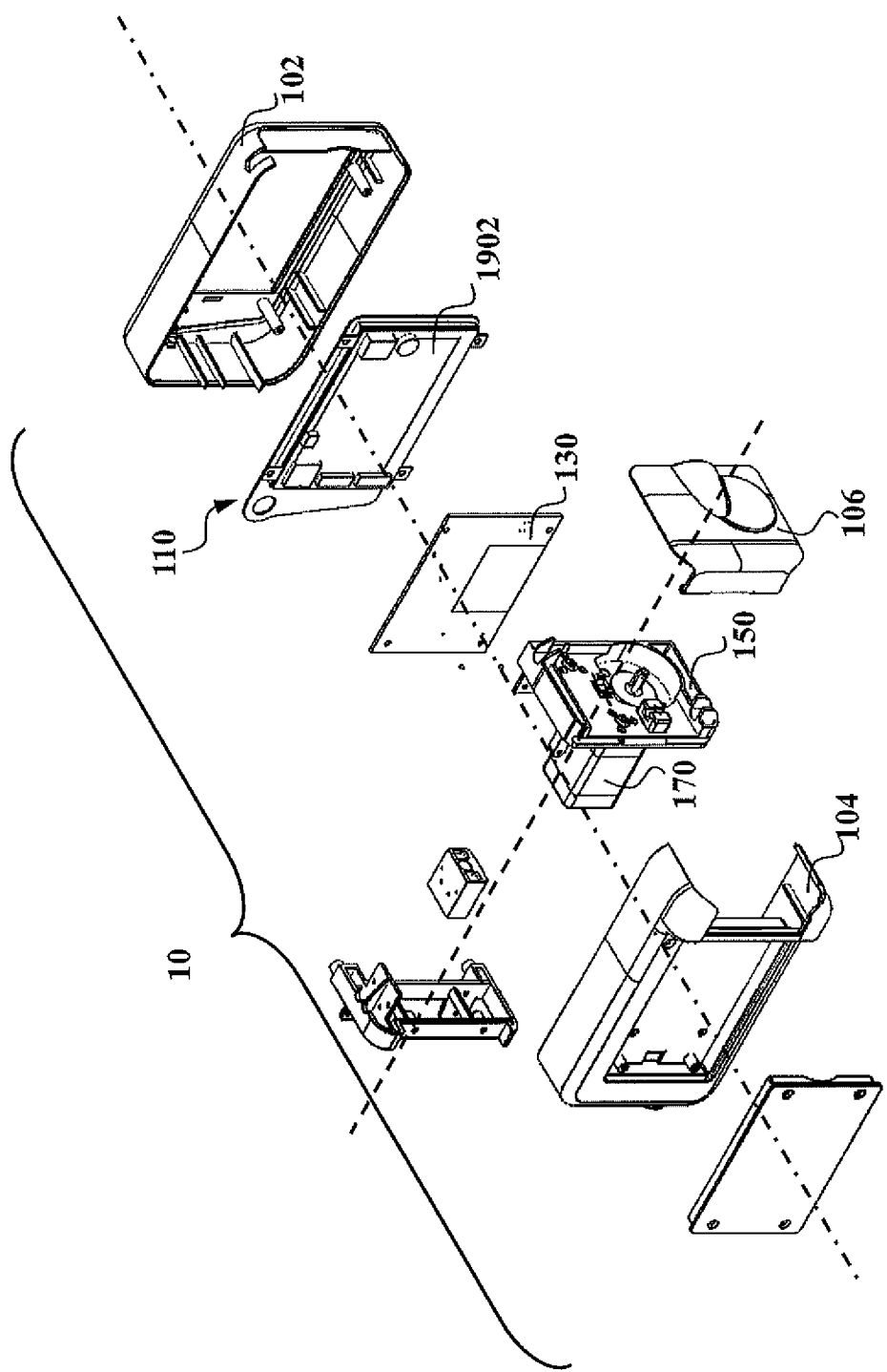
FIG. 5 is an exploded back view of the infusion pump shown in FIG. 1.
Figure 6A:
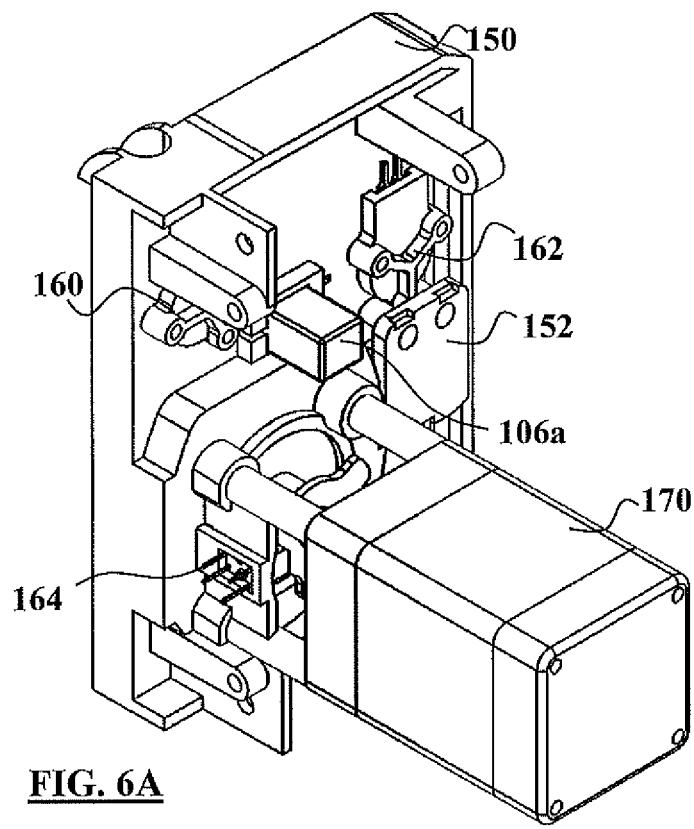
FIG. 6A is a perspective back view showing the cassette holder and components mounted thereto of the infusion pump shown in FIG. 1.
Figure 6B:
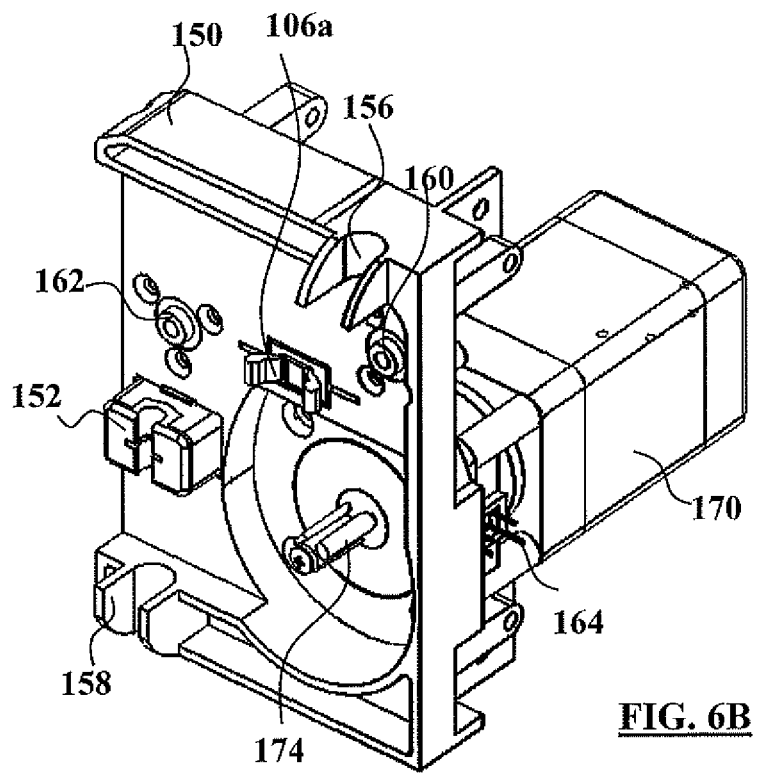
FIG. 6B is a perspective front view of FIG. 6A.
Figure 7A:
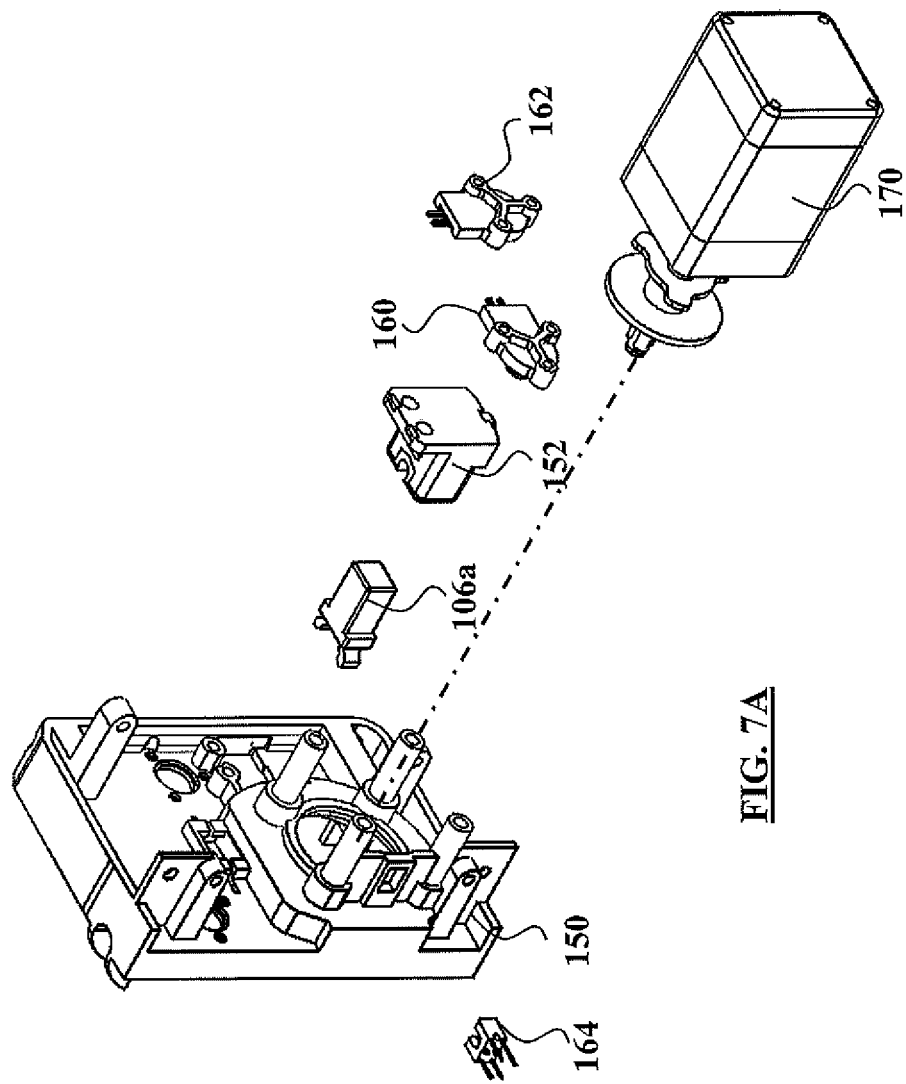
FIG. 7A is an exploded front view of the cassette holder of FIG. 6A.
Figure 7B:
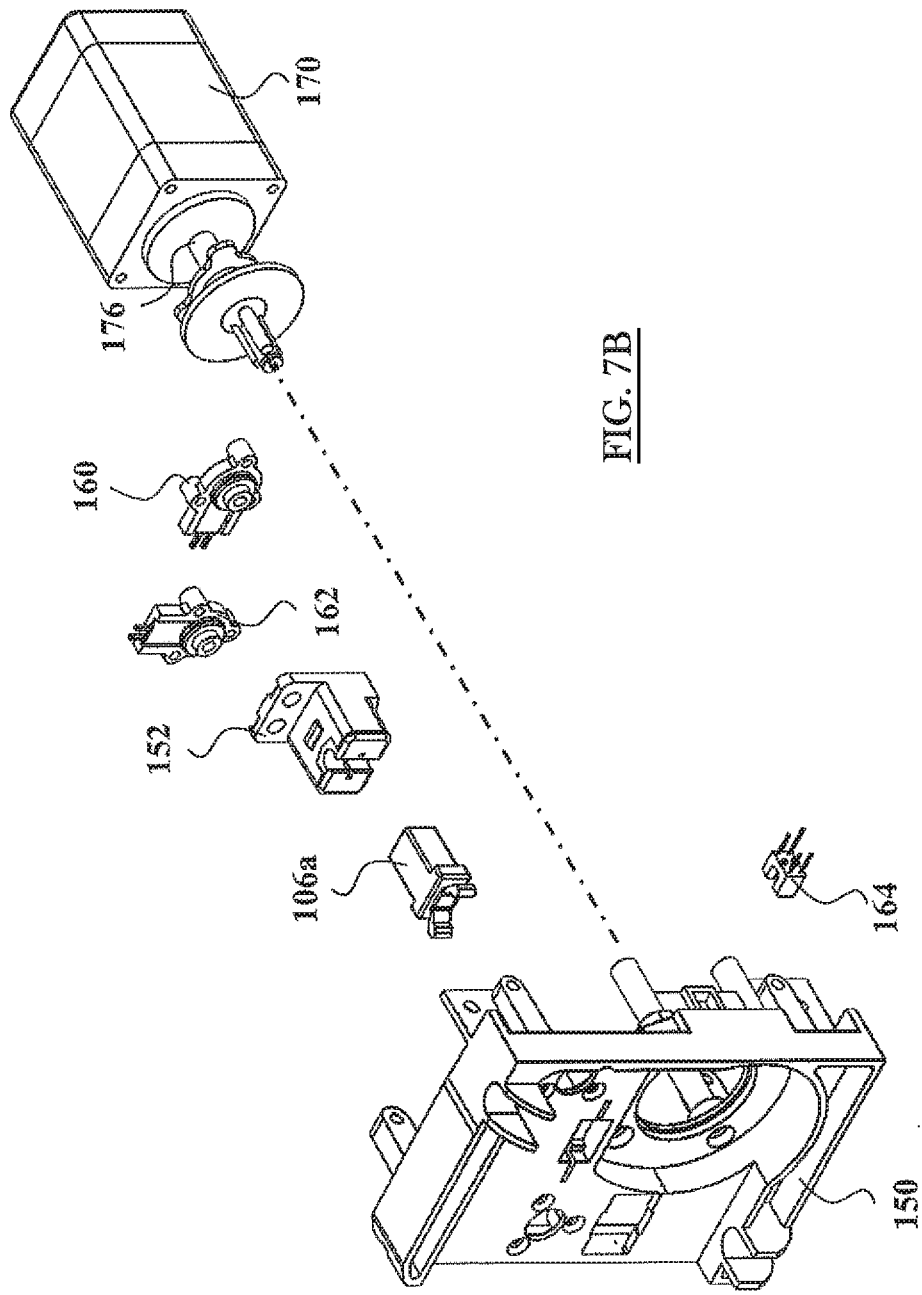
FIG. 7B is an exploded back view of the cassette holder of FIG. 6A.

It will be readily understood that the components of the embodiments, as generally described and illustrated in the figures herein, may be arranged and designed in a wide variety of different configurations in addition to the described example embodiments. Thus, the following more detailed description of the example embodiments, as represented in conjunction with the figures, is not intended to limit the scope of the embodiments, as claimed, but is merely representative of example embodiments.

Reference throughout this specification to "one embodiment", "another embodiment" or "an embodiment" (or the like) means that a particular feature, structure, or characteristic described in connection with the embodiment is included in at least one embodiment. Thus, the appearance of the phrases "in one embodiment" or "in an embodiment" or the like in various places throughout this specification are not necessarily all referring to the same embodiment.

Furthermore, the described features, structures, or characteristics may be combined in any suitable manner in one or more embodiments. In the following description, numerous specific details are provided to give a thorough understanding of embodiments. One skilled in the relevant art will recognize, however, that the various embodiments can be practiced without one or more of the specific details, or with other methods, components, materials, etc. In other instances, some or all known structures, materials, or operations may not be shown or described in detail to avoid obfuscation.

As shown in FIGS. 1 to 7, in one embodiment, a medical infusion pump 10 comprises a front housing 102 and a back housing 104 engaged with each other, forming a casing 101 in which a cassette compartment 1502 and a main compartment 1504 are formed. A cassette holder 150 is positioned between the cassette compartment 1504 and the main compartment 1502 (FIG. 3A). The infusion pump 10 includes a cassette compartment cover 106 rotatably coupled to the casing 101 about a pivot A1 (FIG. 3B). When the cassette compartment cover 106 is opened, the cassette compartment 1502 is exposed for loading a tube cassette 600 therein (FIG. 3C and FIG. 3D). When the cassette compartment cover 106 is closed, the cassette compartment 1502 is protected.

The infusion pump 10 includes a latch 106a coupled to the cassette holder 150 for securing a tube cassette 600 loaded in the cassette compartment 1502.

The casing 101 has a first opening 1022 formed at a top portion, and a second opening 1042 formed at a bottom portion of the back housing 104. The first opening 1022 is used to accommodate an inlet tube 1506a to be connected to an inlet of the tube cassette 600. The second opening 1042 is used to accommodate an outlet tube 1506b to be connected to an outlet of the tube cassette 600.

The infusion pump 10 has a first pressure sensor 160 and a second pressure sensor 162 mounted to the cassette holder 150, for detecting the fluid pressure of an upper tube segment 1508 and a lower tube segment 1510 of the tube cassette 600, respectively. The pressure of the upper tube segment 1508 and/or the lower tube segment 1510 detected by the first and second pressure sensors are used to monitor and detect occlusion at the upper tube segment 1508 and/or the lower tube segment 1510, respectively.

The infusion pump 10 includes at least one air in line sensor 164 mounted to the cassette holder 150 for detecting whether air in line occurs in the tube cassette 600 loaded in the cassette compartment 1502, during priming and infusion operations of the infusion pump 10.

A stepper motor 170 is disposed in the main compartment 1504 and mounted to the cassette holder 150, for driving the tube cassette 600 loaded in the cassette compartment 1502, to enable priming and infusion operations of fluid medicine through the tube cassette 600. A main body portion of the stepper motor 170 is positioned in the main compartment 1504. The stepper motor has a motor shaft 174 extending into the cassette compartment 1502, for engaging a tube cassette 600 loaded in the cassette compartment 1502. The stepper motor 170 is positioned with the shaft 174 parallel to the screen 1902, such that the volume and dimension of the infusion pump 10 can be more compact.

The infusion pump 10 may include a barcode reader 120 positioned in the main compartment 1504, for reading a barcode on the tube cassette 600 loaded in the cassette compartment 1502.

The infusion pump 10 has a user interface e.g. control panel 110 accessible from the front housing 102. The control panel 110 includes a screen 1902 for displaying information, instructions and questions and status of the infusion pump 10, during an infusion operation. In some of the configuration operations, the screen 1902 is configured to be a touch screen keyboard or keypad for entering data, setup parameters and related information into the infusion pump 10, for system configuration and set up. The control panel 110 has a first operator such as a green colored button 112 and a second operator such as a red colored button 114 mounted thereon. The first (green) button 112 and the second (red) button 114 are configured for receiving a user's instructions upon the user responding to a prompt or a question displayed on the screen 1902, or for an instruction sent to the infusion pump 10.

The infusion pump 10 has a printed circuit board (PCB) 130 disposed in the main compartment 1504. The PCB 130 has a processing unit 132 mounted thereon and a memory device 134 coupled to the processing unit 132. The processing unit 132 is configured to execute programs for the operation of the infusion pump 10. The memory device 134 is configured to store initial system setup data, parameters and relative information, and programs to be executed by the processing unit 132.

The infusion pump 10 has an audio alarm device 180 to provide status alert, a power switch 142 for controlling power supply to the infusion pump 10, a battery 140 and a power connector 146 for supplying power to the infusion pump 10, and a USB port 136 for data communication with a peripheral device.

Figure 8:
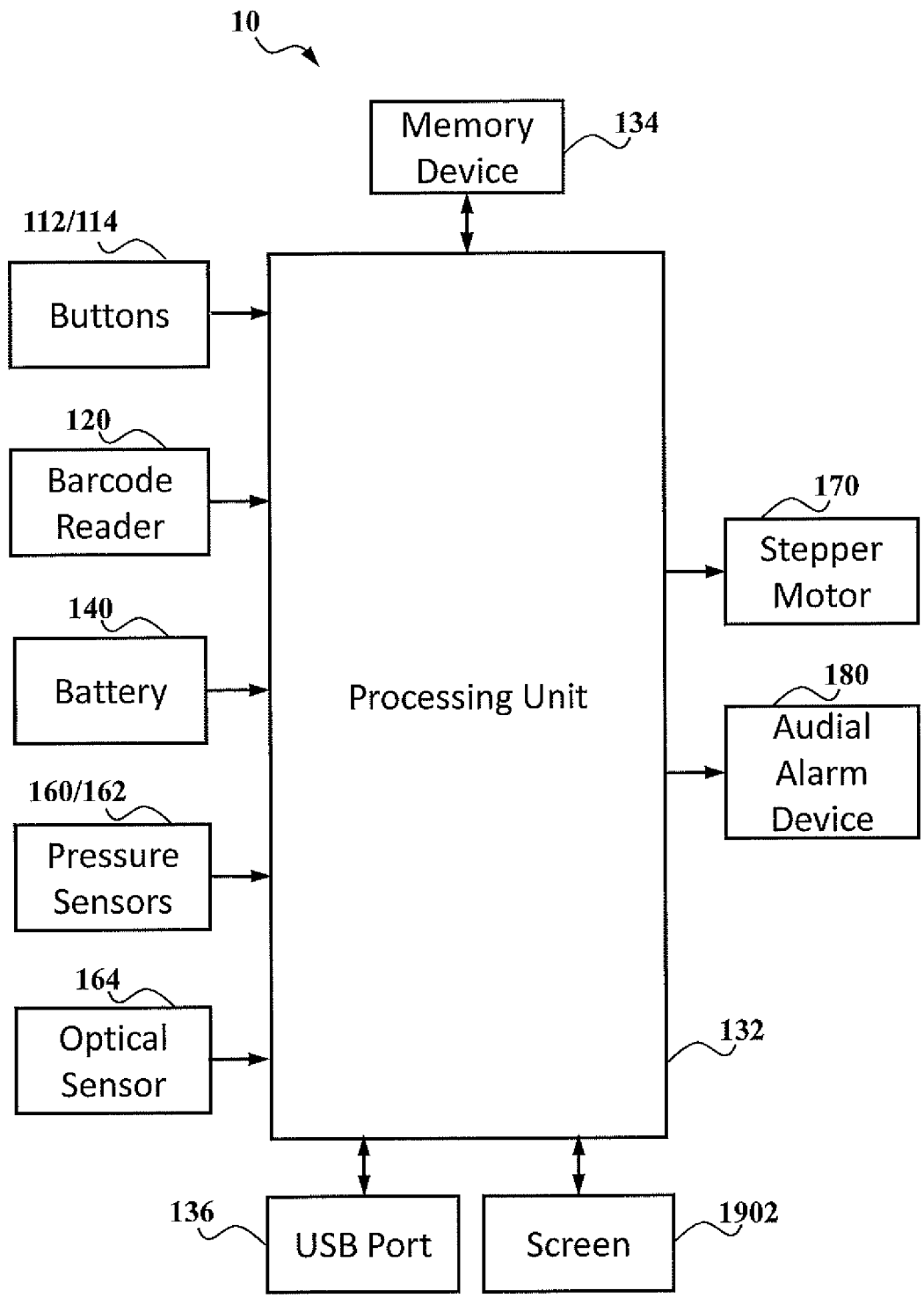
FIG. 8 is a block diagram showing functional modules of the infusion pump of FIG. 1.

As shown in FIG. 8, the processing unit 132 is coupled to and in data communication with the first button 112, the second button 114, the barcode reader 120, the memory device 134, the battery 140, the first and second pressure sensors 160, 162, the air in line sensor 164, the stepper motor 170, the audio alarm device 180, and the screen 1902.

The processing unit 132 and the memory device 134 are in data communication with each other. For example, the processing unit 132 is configured to receive program information from the memory device 134 for execution, for configurating and operating the infusion pump 10. The memory device 134 is configured to receive information such as initial system setup data from the processing unit 132 and to store the initial system setup data therein.

The processing unit 132 is configured to receive information from the first button 112 and the second button 114, the barcode reader 120, the battery 140, the first and second pressure sensors 160, 162, the at least one air in line sensor 164 and the screen 1902. In some operations, the screen 1902 is configured to be a touch screen keyboard or keypad, for receiving data or information input provided through the screen 1902.

As shown in FIGS. 15 to 27D, in use, and upon the infusion pump 10 being powered-on, the screen 1902 displays system information, messages, prompts and instructions in a first column 3912, a second column 3914 and a third column 3916, respectively. The first column 3912 is configured for displaying system information, instructions and alarm messages. The second column 3914 is configured for displaying one or more questions generated by the infusion pump, to which response is needed, or used for enabling data input, for the purpose of control the operations of the infusion pump 10. The third column 3916 is configured for indicating the functions of the first button 112 and the second button 114. The screen 1902 includes a status bar 3918 for indicating a system status during the control, configuration and operation process of the infusion pump 10.

Figure 9:
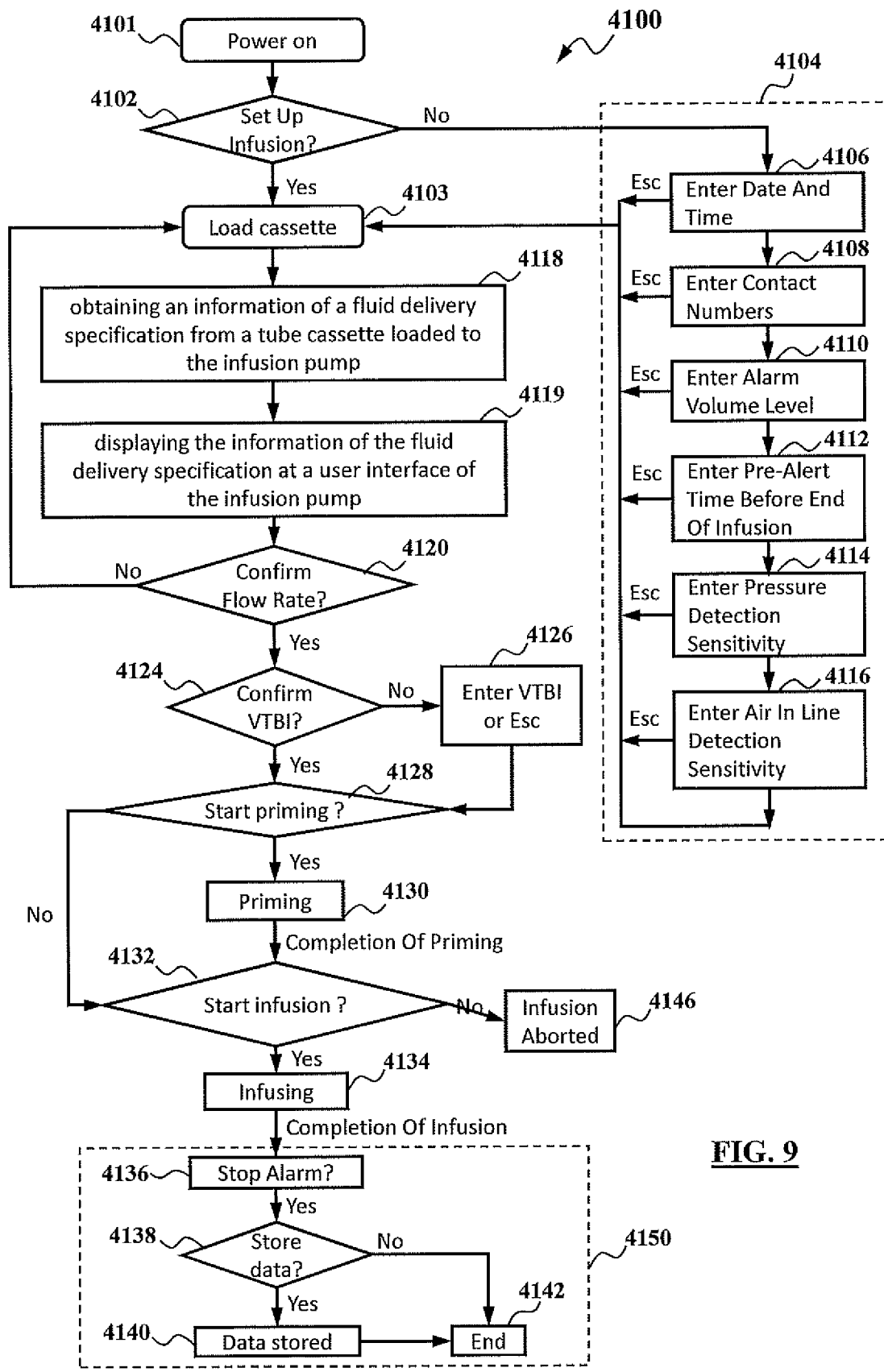
FIG. 9 is a flowchart showing a method of an infusion pump control according to one embodiment of the present invention.
Figure 10:
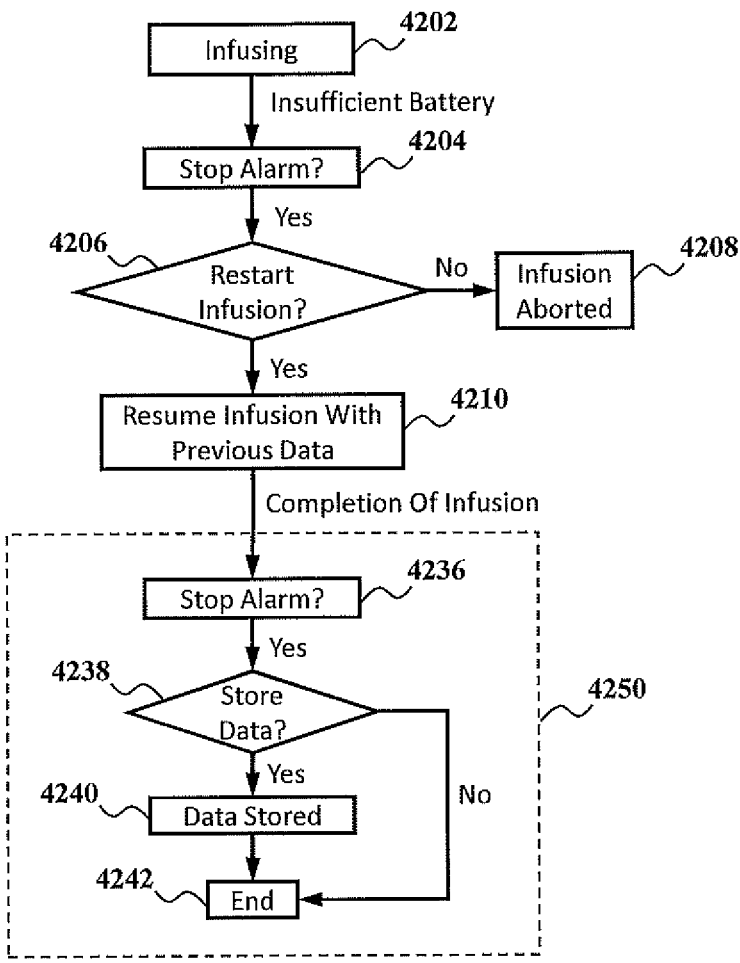
FIG. 10 is a flowchart illustrating a method of an infusion pump control when there is insufficient battery power during infusing.

As depicted in FIG. 9 and in conjunction with FIGS. 15 to 22B, a method 4100 for an infusion pump control includes, upon the infusion pump powered on at block 4101, displaying a first menu 3102 at block 4102, asking a user whether to set up infusion.

Figure 15:
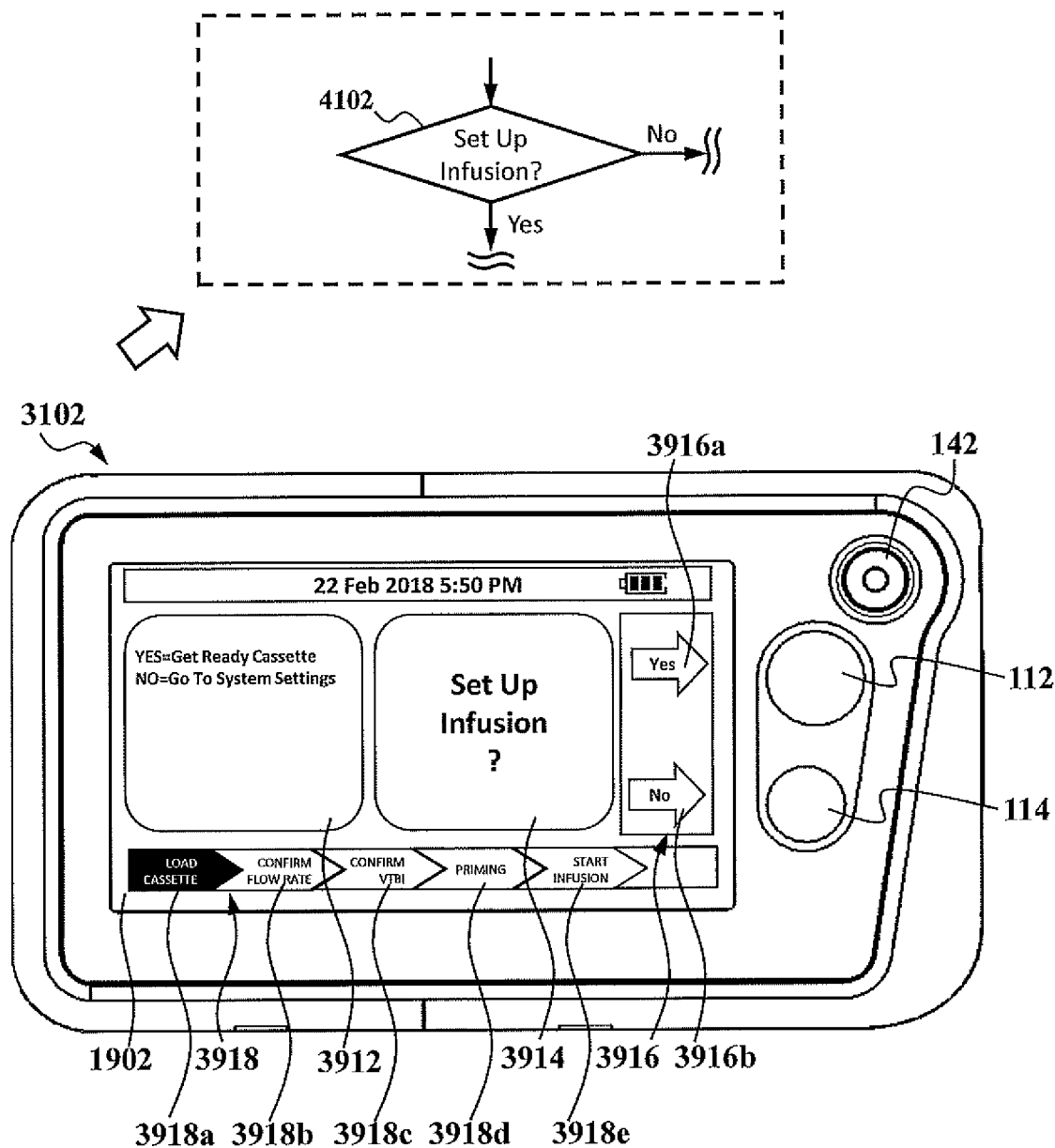
FIGS. 15 to 27D are schematic diagrams showing menus, corresponding method steps and relevant information displayed on a screen in the infusion pump of FIG. 1 during control, configuration and operation.

As shown in FIG. 15, in a first menu 3102 displayed on the screen 1902, a message "YES=Get Ready Cassette, No=Go To System Settings" is shown in the first column 3912 of the screen 1902; a message of "Set Up Infusion?" is shown in the second column 3914 of the screen 1902; a "Yes" indicator 3916a is shown at an upper part of the third column 3916 of the screen 1902 and pointing to the first (green) button 112; a "No" indicator 3916b is shown at a lower part of the third column 3916 of the screen 1902 and pointing to the second (red) button 114. The status is shown as "LOAD CASSETTE" in the status bar 3918 displayed on the screen 1902.

If the system setup is not necessary, a user presses the first (green) button 112 upon which, the infusion pump 10 skips the initial system setup steps 4104. After a tube cassette is loaded, as shown at block 4103, the infusion pump 10 proceeds to start the infusion setup at block 4118.

If the system setup is desirable, a user presses the second (red) button 114 upon which, the infusion pump 10 enters an initial system setup step procedure as indicated at block 4104.

Initial System Setup

In the initial system setup steps 4104 (FIG. 9), the infusion pump 10 displays a second menu 3106 (FIG. 16A), a third menu 3108 (FIG. 16B), a fourth menu 3110 (FIG. 16C), a fifth menu 3112 (FIG. 16D), a sixth menu 3114 (FIG. 16E) and a seventh menu 3116 (FIG. 16F), requesting input of initialization information and/or system setup information such as the system date/time, a contact number(s) of caregiver or a user, an audio alarm volume level, a pre-alert time before end of infusion, a pressure detection sensitivity, and an air-in-line detection sensitivity, etc.

Figure 16A:
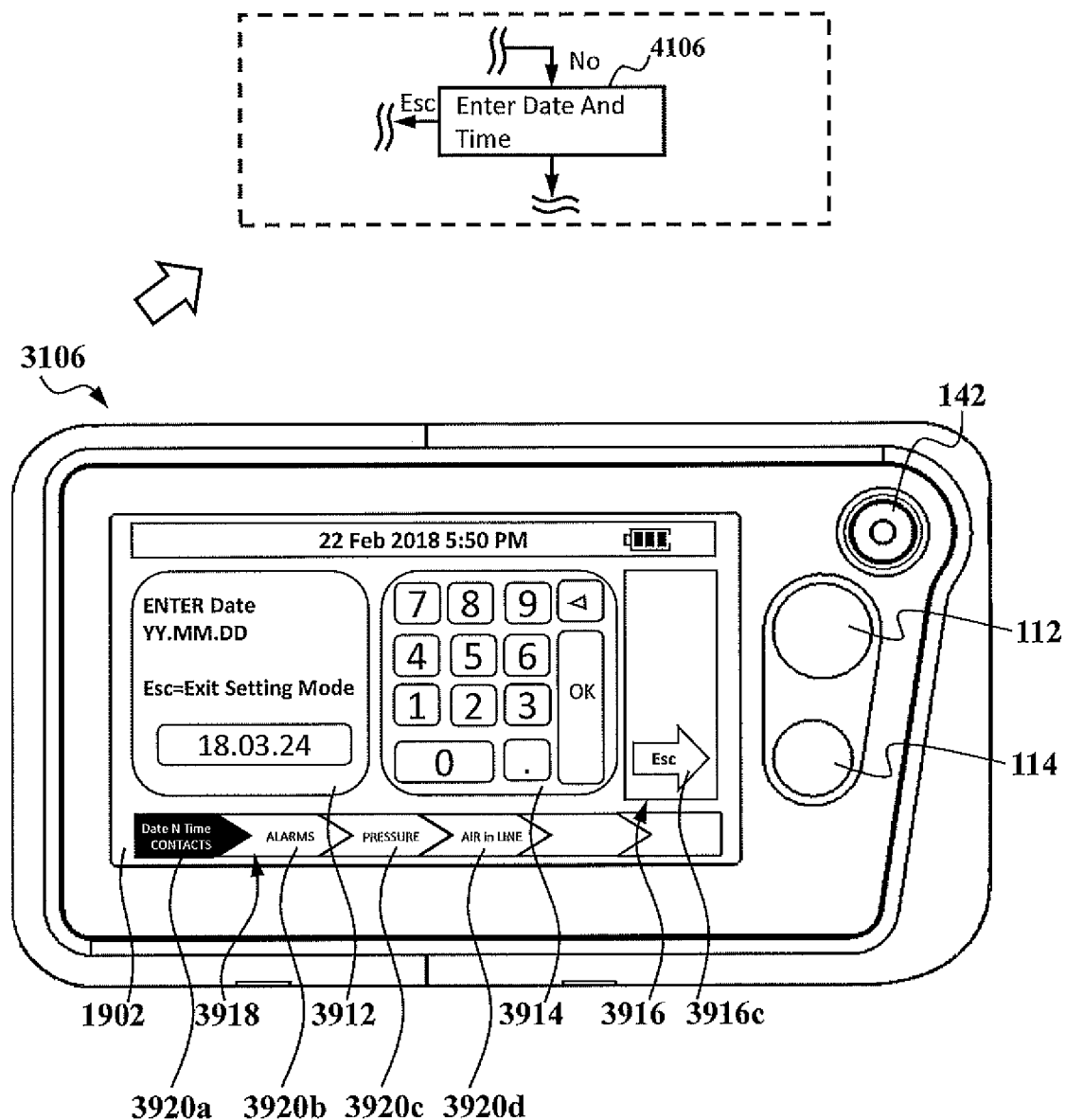

As shown in FIG. 16A, in the second menu 3106, a message of "ENTER Date YY.MM.DD, Esc=Exit Setting Mode" and a default or current date are shown in the first column 3912 of the screen 1902. The second column 3914 of the screen 1902 is configured as a touch screen keyboard for entering of date/time. An "Esc" indicator 3916c is shown at the lower portion of the third column 3916 of the screen 1902, pointing to the second (red) button 114. The status is shown as "Date N Time CONTACTS" in the status bar 3918 displayed on the screen 1902.

Upon a user entering the date/time and pressing "OK" through the touch screen keyboard in the second column 3914 of the screen 1902, the infusion pump 10 displays a third menu 3108 at block 4108, asking a user to enter contact numbers.

Figure 16B:
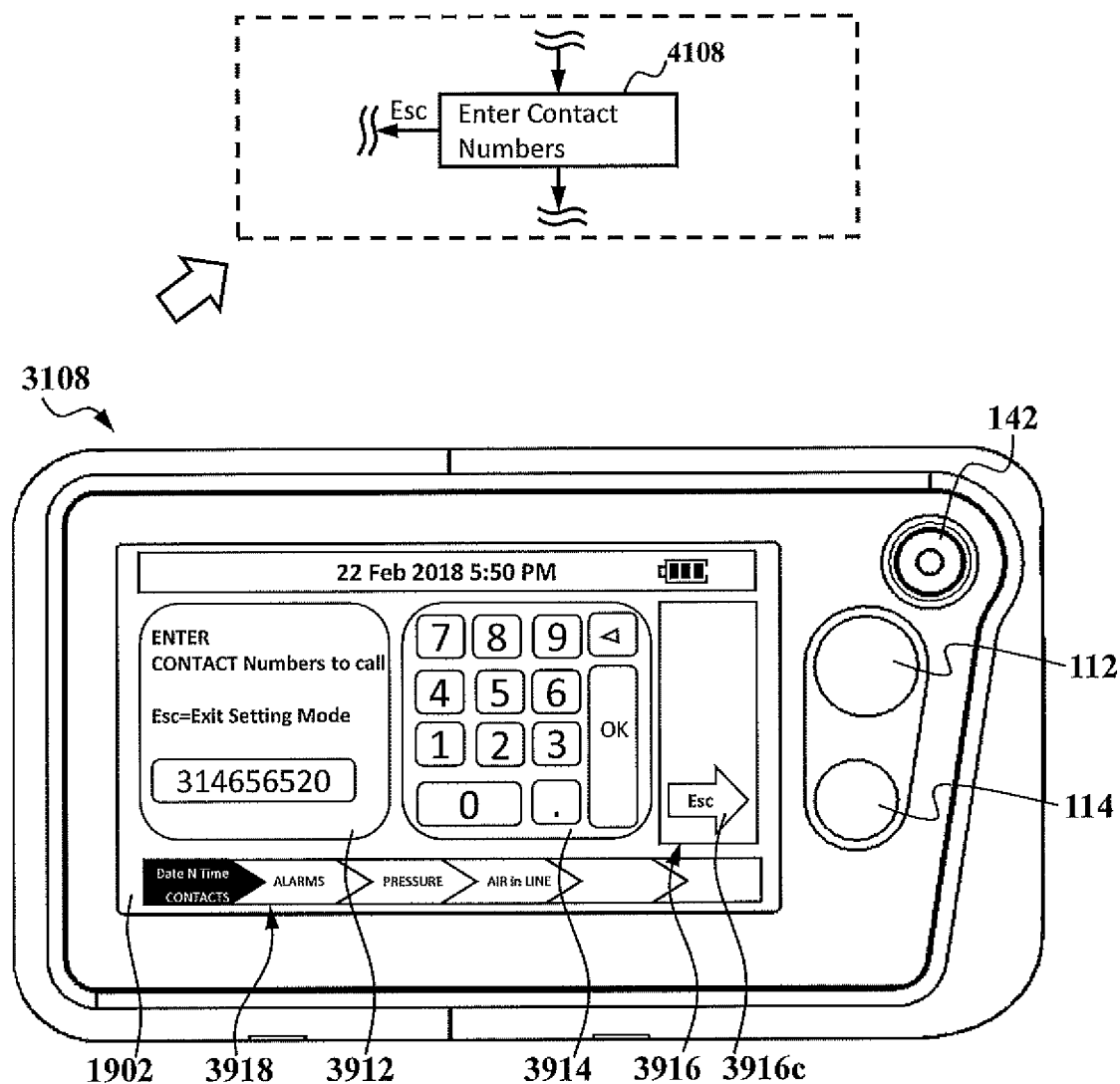

As shown in FIG. 16B, in the third menu 3108, a message of "ENTER Contact Numbers to call, Esc=Exit Setting Mode" and a default or previously entered contact number is shown in the first column 3912 of the screen 1902. The second column 3914 of the display screen is configured as a touch screen keyboard or keypad for entering of contact numbers. An "Esc" indicator 3916c is shown at the lower part of the third column 3916 of the screen 1902 and pointing to the second (red) button 114. The status is shown as "Date N Time CONTACTS" in the status bar 3918 displayed on the screen 1902.

Upon a user entering the contact number and pressing "OK" through the touch screen keyboard/keypad in the second column 3914 on the screen 1902, the infusion pump 10 displays a fourth menu 3110 at block 4110 asking a user to enter audio alarm volume level.

Figure 16C:
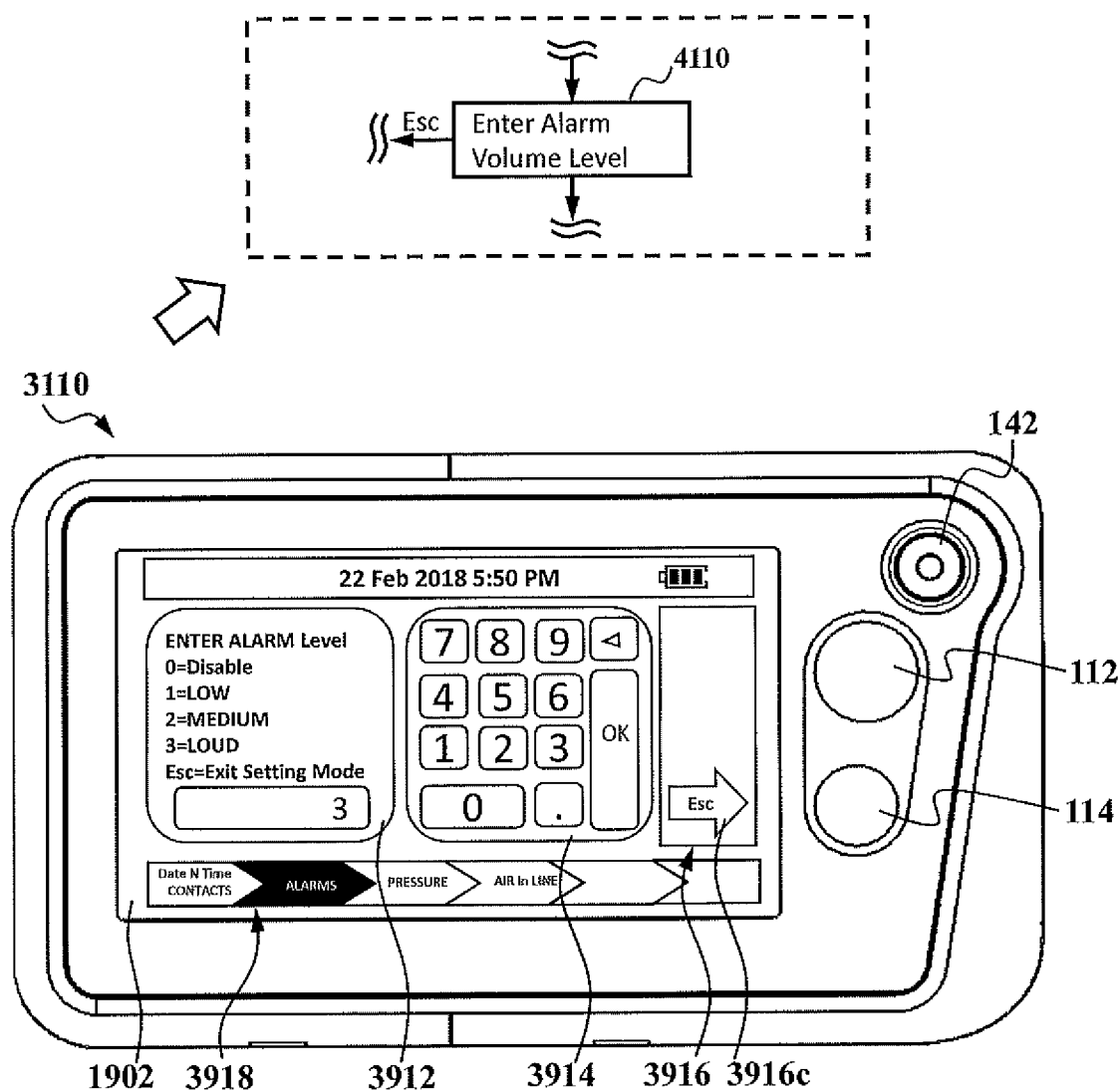

As shown in FIG. 16C, in the fourth menu 3110, a message of "ENTER Alarm Level 0=Disable, 1=LOW, 2=MEDIUM, 3=LOUD, Esc=Exit Setting Mode" and a default or a previously entered alarm level is shown in the first column 3912 of the screen 1902. The second column 3914 of the screen 1902 is configured as a touch screen keyboard for the alarm volume level entry. An "Esc" indicator 3916c is shown at the lower part of the third column 3916 of the screen 1902 and pointing to the second (red) button 114. The status is shown as "ALARMS" in the status bar 3918 displayed on the screen 1902.

Upon a user entering the desired audio alarm volume level and pressing "OK" through the touch screen keyboard/keypad in the second column 3914 of the screen 1902, the infusion pump 10 displays a fifth menu 3112 at block 4112, asking a user to enter prior alert time before end of infusion.

Figure 16D:
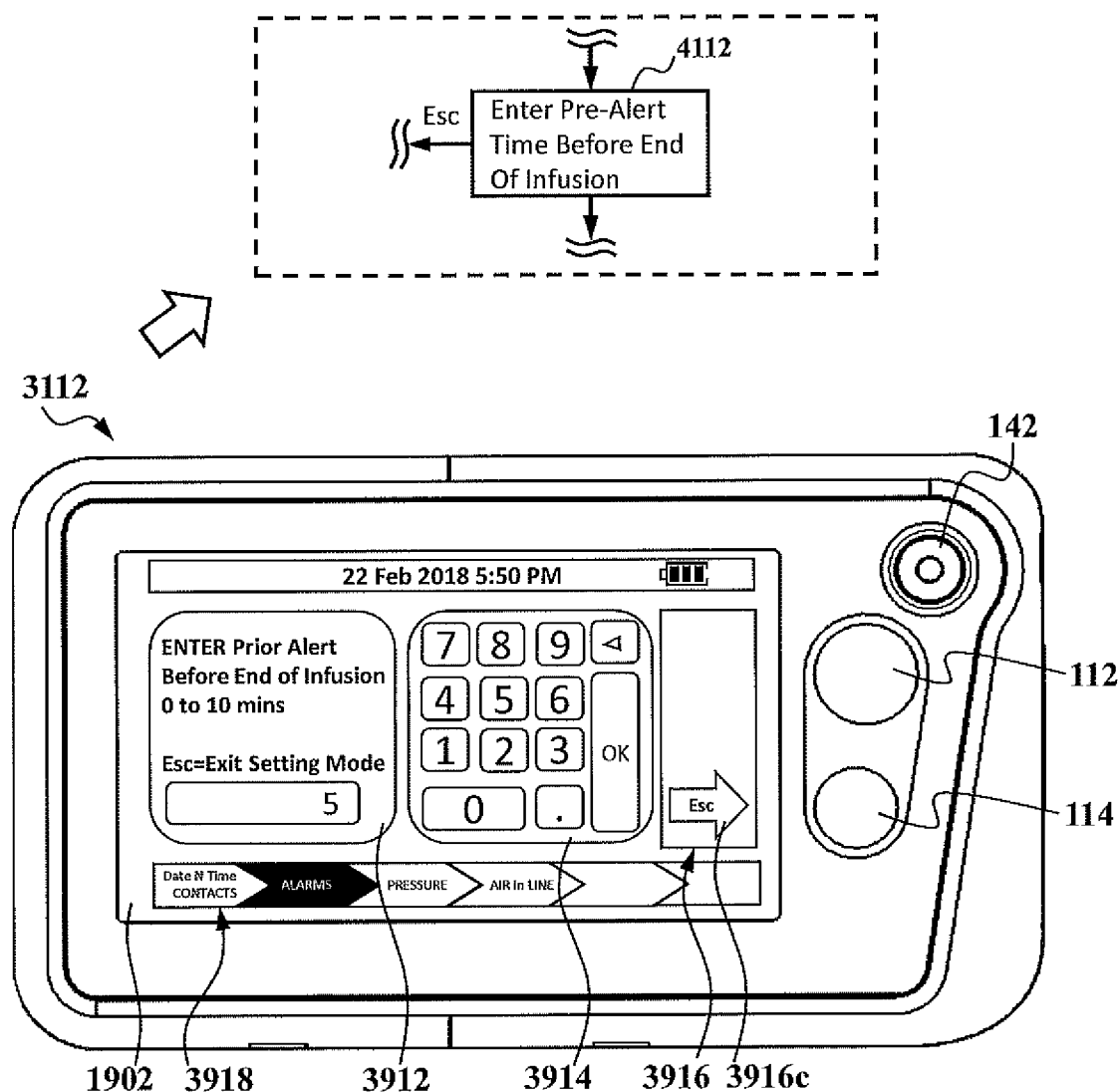

As shown in FIG. 16D, in the fifth menu 3112, a message of "ENTER Prior Alert Before End Of Infusion 0 to 10 mins, Esc=Exit Setting Mode" and a default or previously entered prior alert time before end of infusion is shown in the first column 3912 of the screen 1902. The second column 3914 of the screen 1902 is configured as a touch screen keyboard for prior-alert time entry. An "Esc" indicator 3916c is shown at the lower part of the third column 3916 of the screen 1902 and pointing to the second (red) button 114. The status is shown as "ALARMS" in the status bar 3918 displayed on the screen 1902.

Upon a user entering the prior alert time before end of infusion and pressing "OK" through the touch screen keyboard in the second column 3914 of the screen 1902, the infusion pump 10 displays a sixth menu 3114 at block 4114 asking a user to enter pressure detection sensitivity.

Figure 16E:
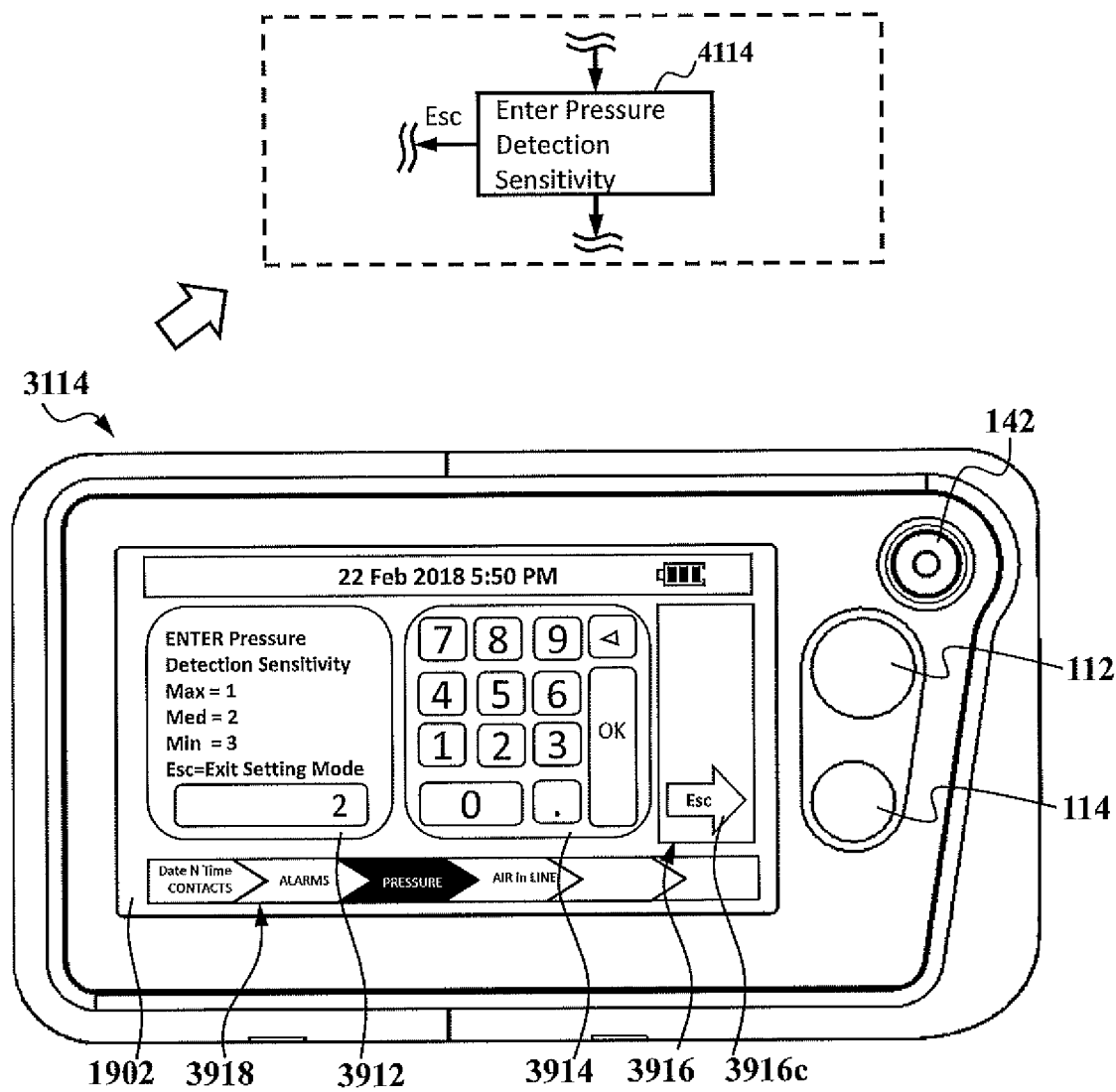

As shown in FIG. 16E, in the sixth menu 3114, a message of "ENTER Pressure Detection Sensitivity Max=1, Med=2, Min=3, Esc=Exit Setting Mode" and a default or previously entered pressure detection sensitivity is shown in the first column 3912 of the screen 1902. The second column 3914 of the screen 1902 is configured as a touch screen keyboard for pressure detection sensitivity entry. An "Esc" indicator 3916c is shown at the lower part of the third column 3916 of the screen 1902 and pointing to the second (red) button 114. The status is shown as "PRESSURE" in the status bar 3918 displayed on the screen 1902.

Upon a user entering the pressure detection sensitivity and pressing "OK" through the touch screen keyboard in the second column 3914 of the screen 1902, the infusion pump 10 displays a seventh menu 3116 at block 4116 asking a user to enter "air in line" detection sensitivity.

Figure 16F:
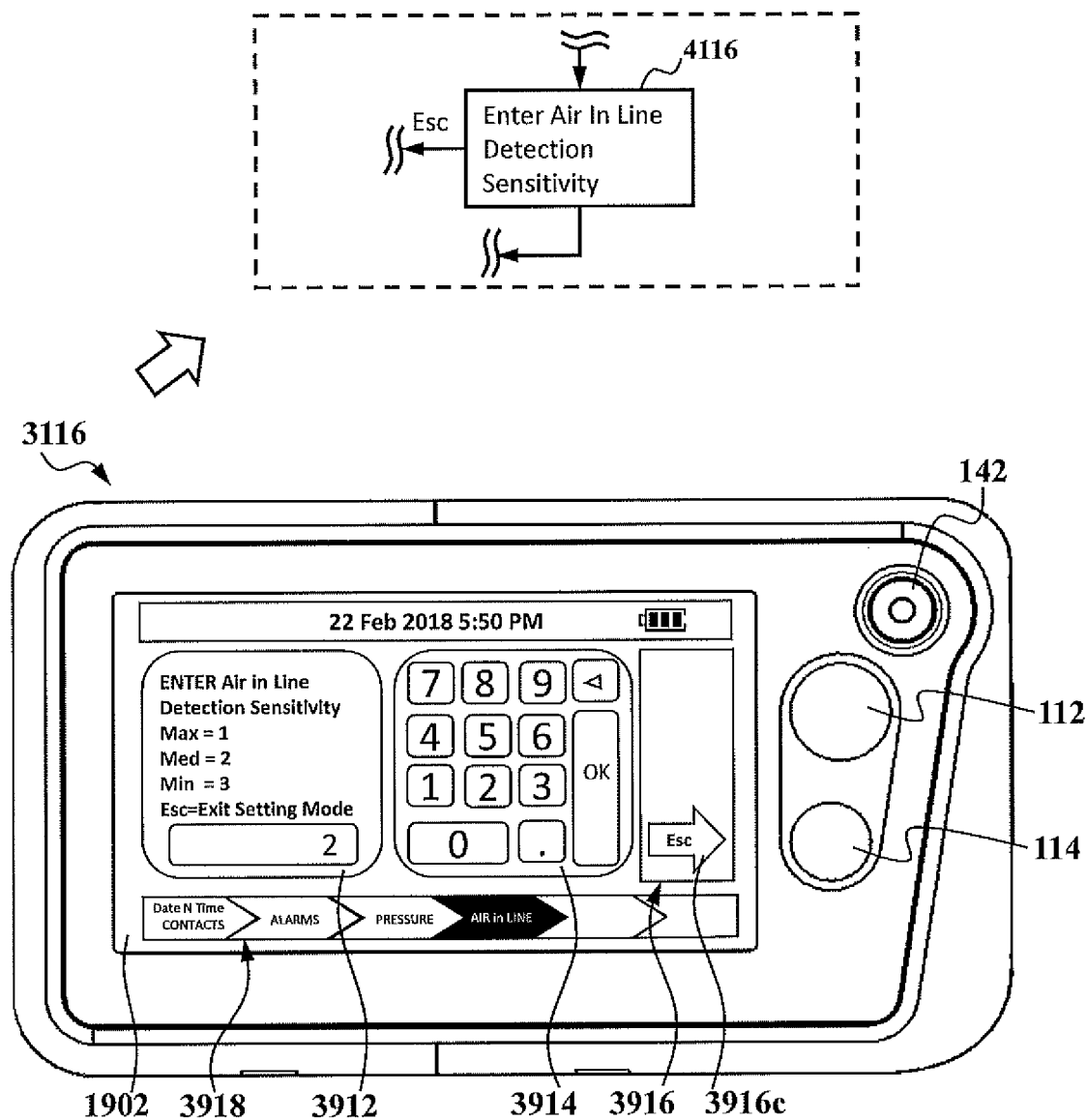

As shown in FIG. 16F, in the seventh menu 3116, a message of "ENTER Air in Line Detection Sensitivity Max=1, Med=2, Min=3, Esc=Exit Setting Mode" and a default or previously entered "air in line" detection sensitivity is shown in the first column 3912 of the screen 1902. The second column 3914 of the screen 1902 is configured as a touch screen keyboard for "air in line" detection sensitivity entry. An "Esc" indicator 3916c is shown at the lower part of the third column 3916 of the screen 1902 and pointing to the second (red) button 114. The status is shown as "AIR in LINE" in the status bar 3918 displayed on the screen 1902.

Upon a user entering the "air in line" detection sensitivity data and pressing "OK" through the touch screen keyboard/keypad in the second column 3914 of the screen 1902, the infusion pump 10 completes the initial system setup steps 4104. Upon a tube cassette being loaded into the cassette compartment as shown at block 4103, the infusion pump 10 proceeds to infusion setup at block 4118.

If a user presses the second (red) button 114 corresponding to the "Esc" indicator 3916c in any of the second menu 3106 to seventh menu 3116 of the screen 1902, the method 4100 skips the initial system setup steps 4104 and proceed to tube cassette loading at block 4103 and start infusion setup at block 4118.

Infusion Setup

At block 4118, the infusion pump obtains an information of a fluid delivery specification from a tube cassette loaded to the infusion pump by, e.g. an optical label reader e.g. barcode reader of the infusion pump automatically reading a barcode borne on a tube cassette loaded into the cassette compartment, and sends the barcode information to the processing unit of the infusion pump. The processing unit extracts fluid delivery specification including a flow rate data/information and a Volume-To-Be Infused (VTBI) information from the barcode and sends the flow rate data/information to display on the screen 1902. In another embodiment, the information of a barcode on a tube cassette could be encoded and formatted in such a manner that programming of the therapy specifications into the barcode could be carried out by the care facility. An infusion pump may have a predetermined set of infusion parameters pre-programmed therein, by a data transmission via the USB port of the infusion pump, a WIFI connection, internet connection, mobile network connection or internet-of-things (IoT) network connection, according to a prescription dedicated to a target care receiver, e.g. a flow rate, VTBI, date and time for the infusion, and a sequence ID under each of which an infusion to be carried out. Upon a tube cassette being loaded to an infusion pump, the fluid delivery specification retrieved from the data label on the tube cassette will be checked against the pre-programmed predetermined set of infusion parameters in the infusion pump. If the fluid delivery specification matches the predetermined set of infusion parameters, the tube cassette will be recognized as a correct tube cassette, which allows fluid delivery to be carried out. If the fluid delivery specification mismatches the predetermined set of infusion parameters, the tube cassette will not be recognized as a correct tube cassette, which result in the tube cassette being rejected and no fluid delivery will be carried out.

Accordingly, manual setup of infusion specification is neither necessary nor possible by a care receiver. Supervision by a caregiver during the process of infusion is not required. This method of pump control provides new possibilities in determining the infusion including and not limited to flow rates, volume to be infusion, time and day during which such therapy should take place, etc. In yet another embodiment, predetermined therapy modes could be programmed, for example in certain therapy the pump may be controlled to infuse for a certain duration, remain idle for a certain phase and resume to infuse thereafter, such cycles could be repeated for an intended overall period of infusion. Within the realm of new possibilities offered by such a control means, a patient receiving home therapy could be prescribed with several tube cassettes with different infusion specifications and time and date for such infusions so that risks in incorrect medication sequence is avoided.

The infusion pump displays at block 4119 the information of the fluid delivery specification at a user interface of the infusion pump, e.g. a flow rate under which an infusion is to be carried out, and displays an eighth menu 3120 at block 4120, asking for confirmation whether a correct tube cassette has been loaded (i.e. whether the displayed flow rate is correct).

Figure 17:
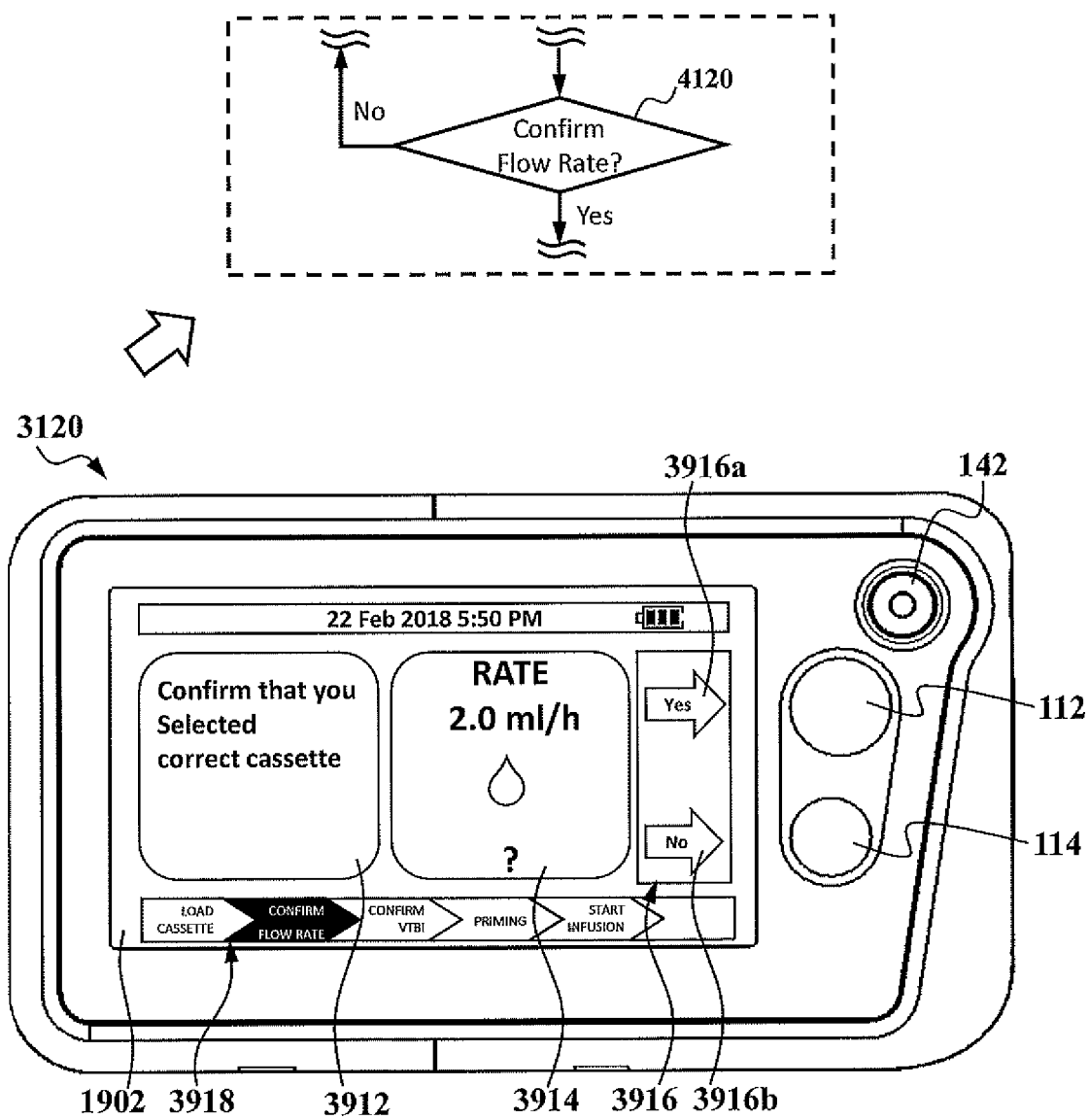

As shown in FIG. 17, in the eighth menu 3120, a message of "confirm that you selected correct cassette" is shown in the first column 3912 of the screen 1902. The flow rate to be confirmed (e.g. a message of "RATE 2.0 ml/h?") is shown in the second column 3914 of the screen 1902. A "Yes" indicator 3916a is shown at the upper part of the third column 3916 of the screen 1902 and pointing to the first (green) button 112. A "No" indicator 3916b is shown at the lower part of the third column 3916 of the screen 1902 and pointing to the second (red) button 114. The status is shown as "CONFIRM FLOW RATE" in the status bar 3918 displayed on the screen 1902, prompting the user that the infusion pump is waiting for confirmation of the flow rate to proceed further.

Upon checking that a correct tube cassette has been loaded (i.e., the displayed flow rate is correct according to an infusion requirement), the user presses the first (green) button corresponding to the "Yes" indicator 3916a in the eighth menu 3120, to send a first response signal i.e. an affirmative indication of accepting the flow rate/confirmation information to, the infusion pump 10 and configure a fluid delivery under the flow rate accepted.

If the displayed flow rate is incorrect, the user presses the second (red) button corresponding to the "No" indicator 3916b in the eighth menu 3120 to send a first response signal i.e. a negative indication of rejecting the flow rate and awaiting the tube cassette to be replaced and loaded. A notice of replacing the tube cassette is displayed on the screen 1902, and the method is directed back to block 4103 for tube cassette replacement. After a new tube cassette is loaded, the method repeats the operations from steps shown at block 4118, until a response is received confirming that a correct tube cassette is loaded.

Each tube cassette is provided with a barcode label with a specific flow rate information included therein. The method only provides options for a user to press the respective button for answering "Yes" or "No", corresponding to whether the displayed flow rate is correct, i.e. to accept a tube cassette of correct flow rate, or to reject a tube cassette of an incorrect flow rate. Manual entry of flow rate is disabled by the infusion pump. An infusion operation is allowed to proceed only upon confirmation of a tube cassette with a correct flow rate is loaded i.e. upon a green button pressed. In an event that a tube cassette with an incorrect flow rate is loaded, the only remaining process is that the infusion pump receives a red button entry by which no infusion will be carried out. As such, a risk of infusion under an incorrect flow rate is prevented.

Upon a user confirming that a correct tube cassette is loaded, by pressing the first (green) button 112 corresponding to the "Yes" indicator 3916a, the infusion pump displays a ninth menu 3124 at block 4124 asking a user to confirm the Volume To Be Infused (VTBI).

Figure 18A:
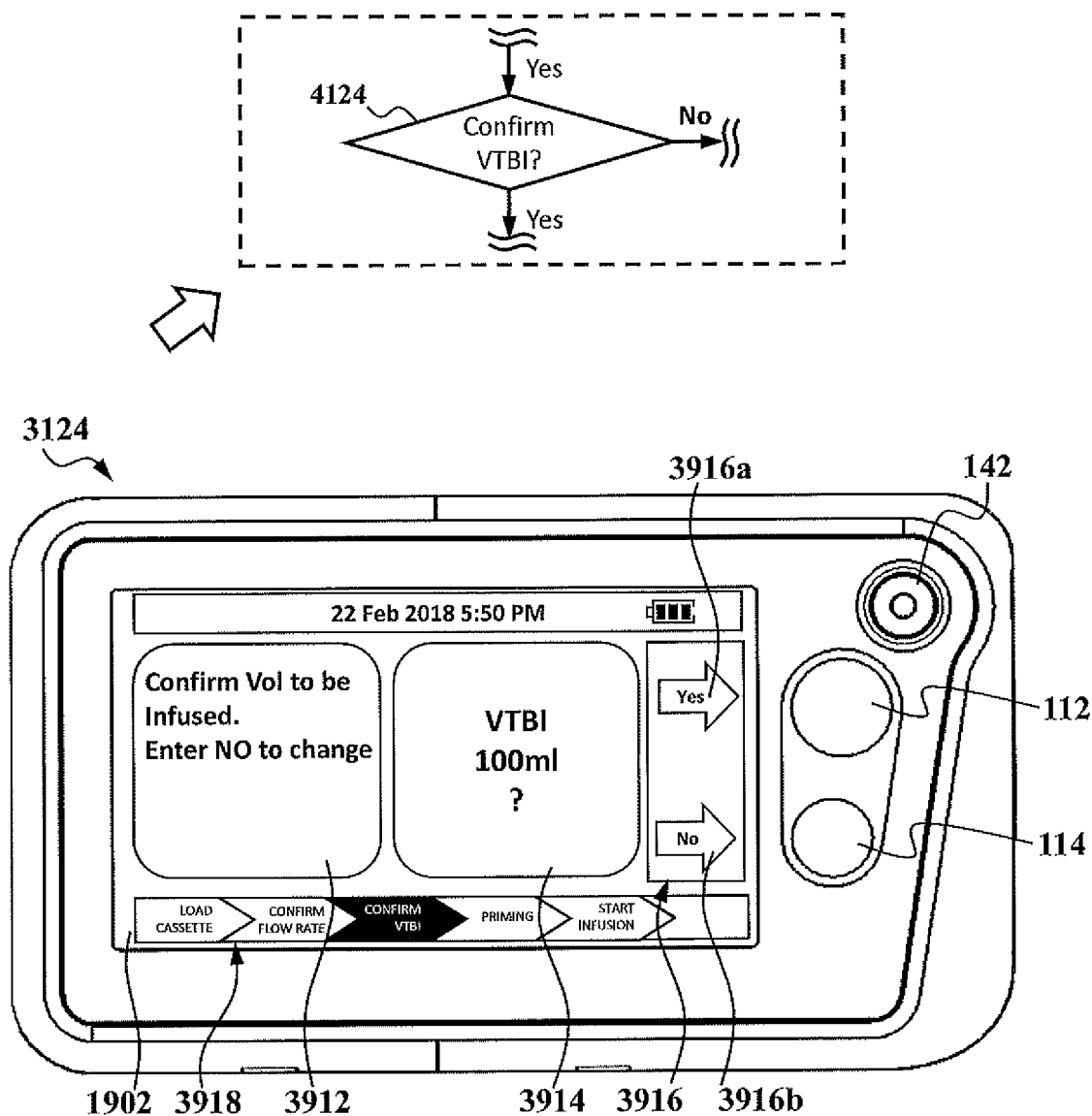

As shown in FIG. 18A, in the ninth menu 3124, a message of "confirm Vol to be Infused. Enter No to change" is shown in the first column 3912 of the screen 1902. A message of "VTBI 100 ml?" is shown in the second column 3914 of the screen 1902 (the default value of VTBI is 100 ml, the message is changed in accordance with the default value of VTBI). A "Yes" indicator 3916a is shown at the upper part of the third column 3916 of the screen 1902 and pointing to the first (green) button 112. A "No" indicator 3916b is shown at the lower part of the third column 3916 of the screen 1902 and pointing to the second (red) button 114. The status is shown as "CONFIRM VTBI" in the status bar 3918 displayed on the screen 1902.

If the default value of VTBI is to be used, the user presses the first (green) button 112 corresponding to the "Yes" indicator 3916*a*, informing the infusion pump to accept the default value of VTBI. The method determines that the default value of VTBI is accepted and displays an eleventh menu 3128 at block 4128 asking a user to confirm whether to start priming.

If a different VTBI is to be used for infusion, the user presses the second (red) button 114 corresponding to the "No" indicator 3916*b*. The infusion pump displays a tenth menu 3126 at block 4126 asking a user to revise the default VTBI value and manually enter a new VTBI value.

Figure 18B:
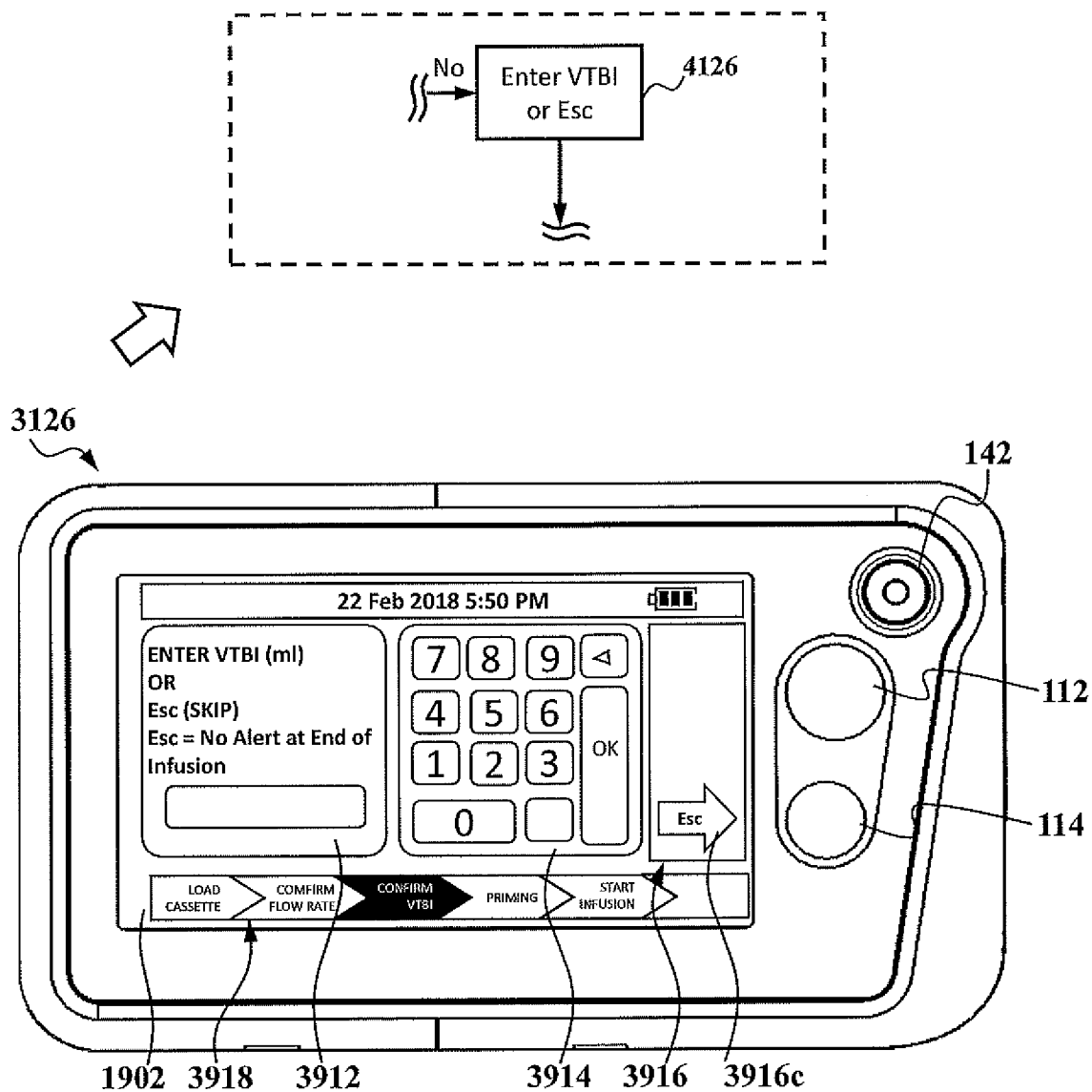

As shown in FIG. 18B in the tenth menu 3126, a message of "ENTER VTBI (ml) OR Esc (SKIP), Esc=No Alert at End of Infusion" and a default or previously entered VTBI value is shown in the first column 3912 of the screen 1902. The second column 3914 of the screen 1902 is configured as a touch screen keyboard for VTBI value entry. An "Esc" indicator 3916*c* is shown at the lower part of the third column 3916 of the screen 1902 and pointing to the second (red) button 114. The status is shown as "CONFIRM VTBI" in the status bar 3918 displayed on the screen 1902.

Upon a VTBI value entered and the "OK" button pressed through the touch screen keyboard in the second column 3914 of the screen 1902, the infusion pump 10 displays an eleventh menu 3128 at block 4128, with a request asking a user to confirm whether to start priming, and the infusion pump 10 receives a second response signal via the control panel 110 for the request.

If a priming operation is not necessary, the infusion pump 10 receives a negative indication upon a user pressing the second (red) button 114, corresponding to the "Esc" indicator 3916*c* and accordingly, the method skips the priming process and proceed to display the twelfth menu 3132 on the infusion pump at block 4132, asking a user whether to start infusion.

Figure 19:
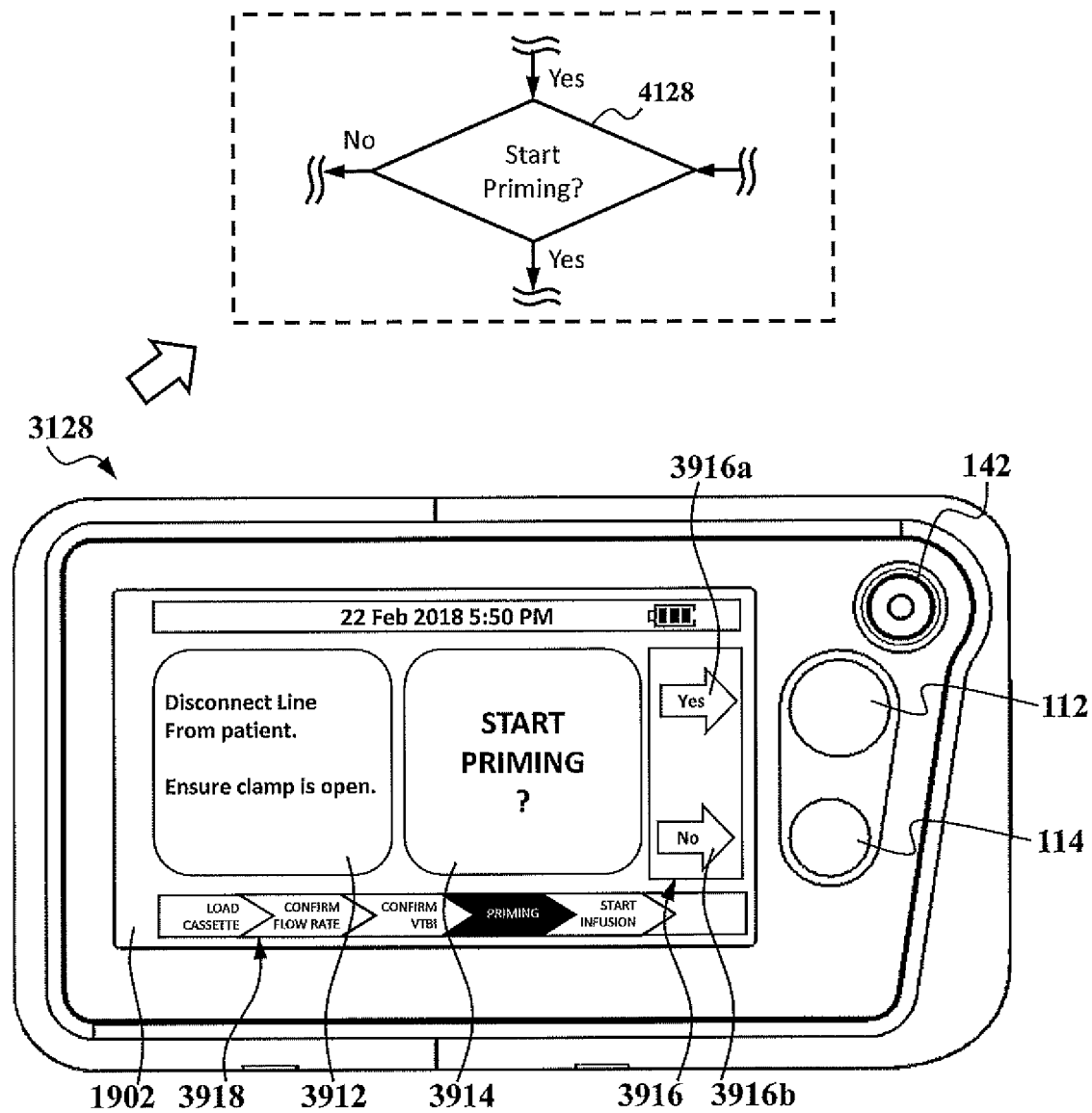

If priming is to be carried out, the infusion pump 10 receives an affirmative indication upon the user pressing the first (green) button 112 by which the infusion pump starts the priming process at block 4130. As shown in FIG. 19, in the eleventh menu 3128, a message of "Disconnect Line From patient. Ensure clamp is open." is shown in the first column 3912 of the screen 1902. A message of "START PRIMING?" is shown in the second column 3914 of the screen 1902. A "Yes" indicator 3916*a* is shown at the upper part of the third column 3916 of the screen 1902 and pointing to the first (green) button 112. A "No" indicator 3916*b* is shown at the lower part of the third column 3916 of the screen 1902 and pointing to the second (red) button 114. The status is shown as "PRIMING" in the status bar 3918 displayed on the screen 1902.

The user is reminded to disconnect line from patient and ensure that the clamp is open before the start of priming, by a message shown in the first column 3912 of the eleventh menu 3128.

The completion of priming (or duration of priming) is determined by the system setting, i.e. default duration of priming. Upon completion of priming, the infusion pump displays a twelfth menu 3132 at block 4132, asking a user to confirm whether to start infusion.

Figure 20:
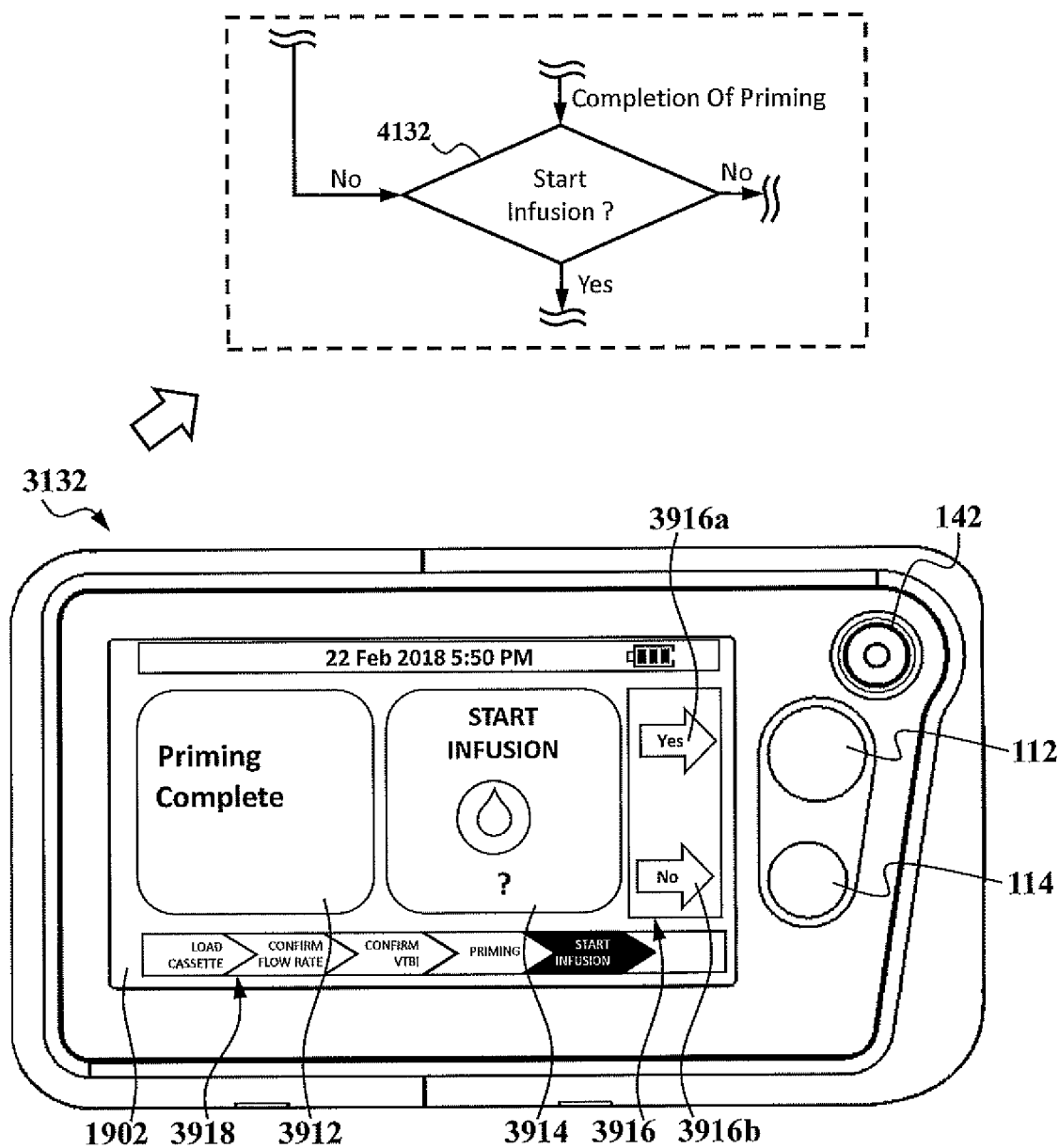

As shown in FIG. 20, in the twelfth menu 3132, a message of "Priming Complete" is shown in the first column 3912 of the screen 1902; a message of "START INFUSION?" is shown in the second column 3914 of the screen 1902; a "Yes" indicator 3916*a* is shown at the upper part of the third column 3916 of the screen 1902 and pointing to the first (green) button 112; a "No" indicator 3916*b* is shown at the lower part of the third column 3916 of the screen 1902 and pointing to the second (red) button 114. The status is shown as "START INFUSION" in the status bar 3918 displayed on the screen 1902.

If infusion is not to be processed, the user presses the second (red) button 114 corresponding to the "No" indicator 3916*b* in the twelfth menu 3132. In response, the infusion pump aborts infusion at block 4146.

Infusion

To confirm to start infusion, the user presses the first (green) button 112 corresponding to the "Yes" indicator 3916*a* in the twelfth menu 3132. The infusion pump starts infusion accordingly, and displays a thirteenth menu 3134 showing infusion information, and disables the first and second buttons at block 4134.

Figure 21:
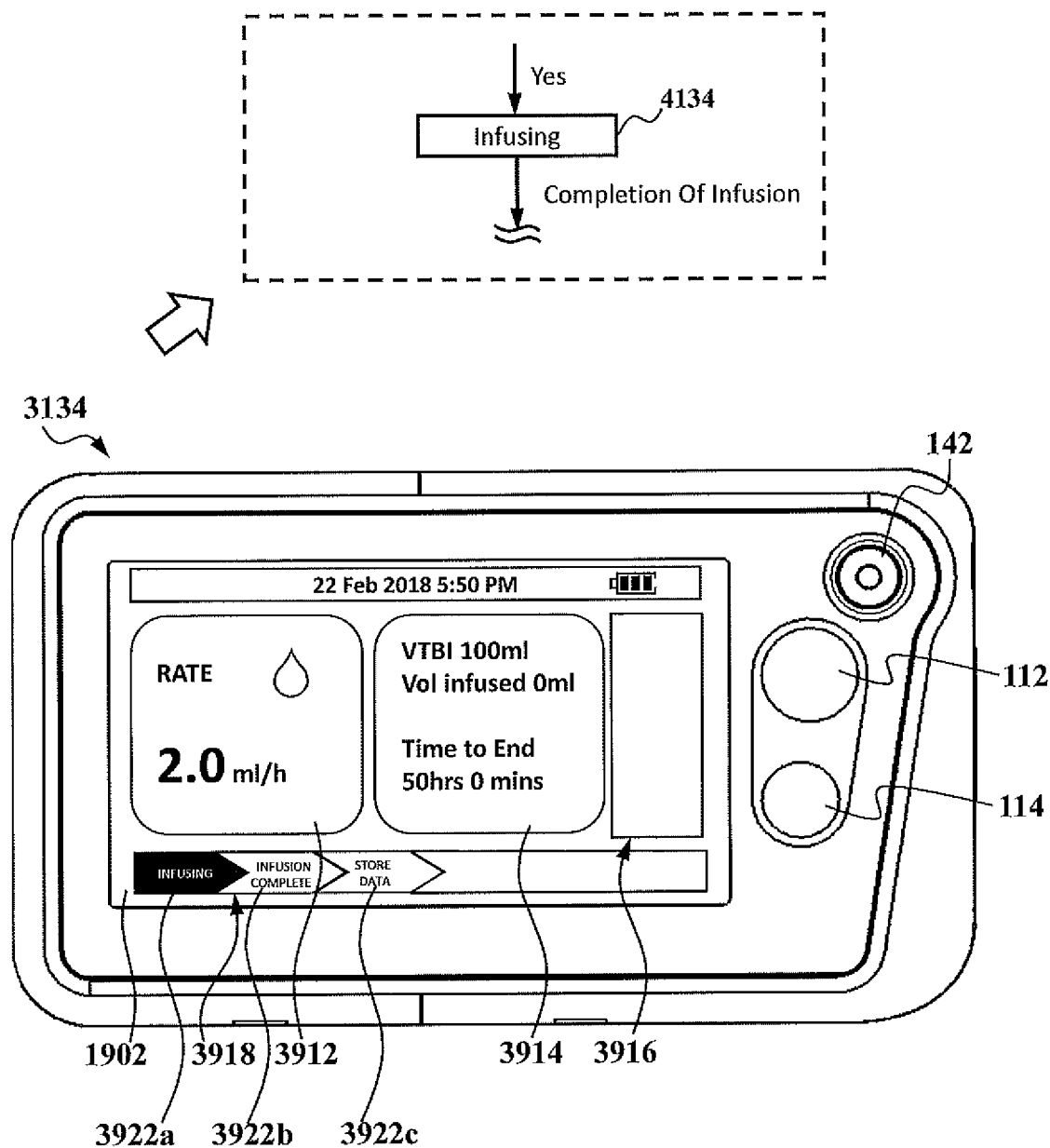

As shown in FIG. 21, in the thirteenth menu 3134, the infusion flow rate (e.g. a message of "RATE 2.0 ml/h") is shown in the first column 3912 of the screen 1902; the volume to be infused (VTBI), volume infused, and remaining time to end of infusion (e.g. a message of "VTBI 100 ml, Vol Infused 0 ml, Time to End 50 hrs 0 mins") are shown in the second column 3914 of the screen 1902. The third column 3916 of the screen 1902 is left blank as during infusion, the functions of the first button and the second button are disabled to prevent any data entry to the infusion pump. The status is shown as "INFUSING" in the status bar 3918 displayed on the screen 1902.

Completion of Infusion and Data Storing

Upon completion of the infusion, the infusion pump proceeds with steps at block 4150 under which, firstly, the infusion pump stops the infusion, enables the first and second buttons 112 and 114, triggers the alarm, and displays a fourteenth menu 3136 at block 4136, asking a user whether to stop alarm. The completion of infusion (or duration of infusion) is determined by the volume to be infused set at step 4124 or step 4126 and the flow rate retrieved from the barcode on the tube cassette.

Figure 22A:
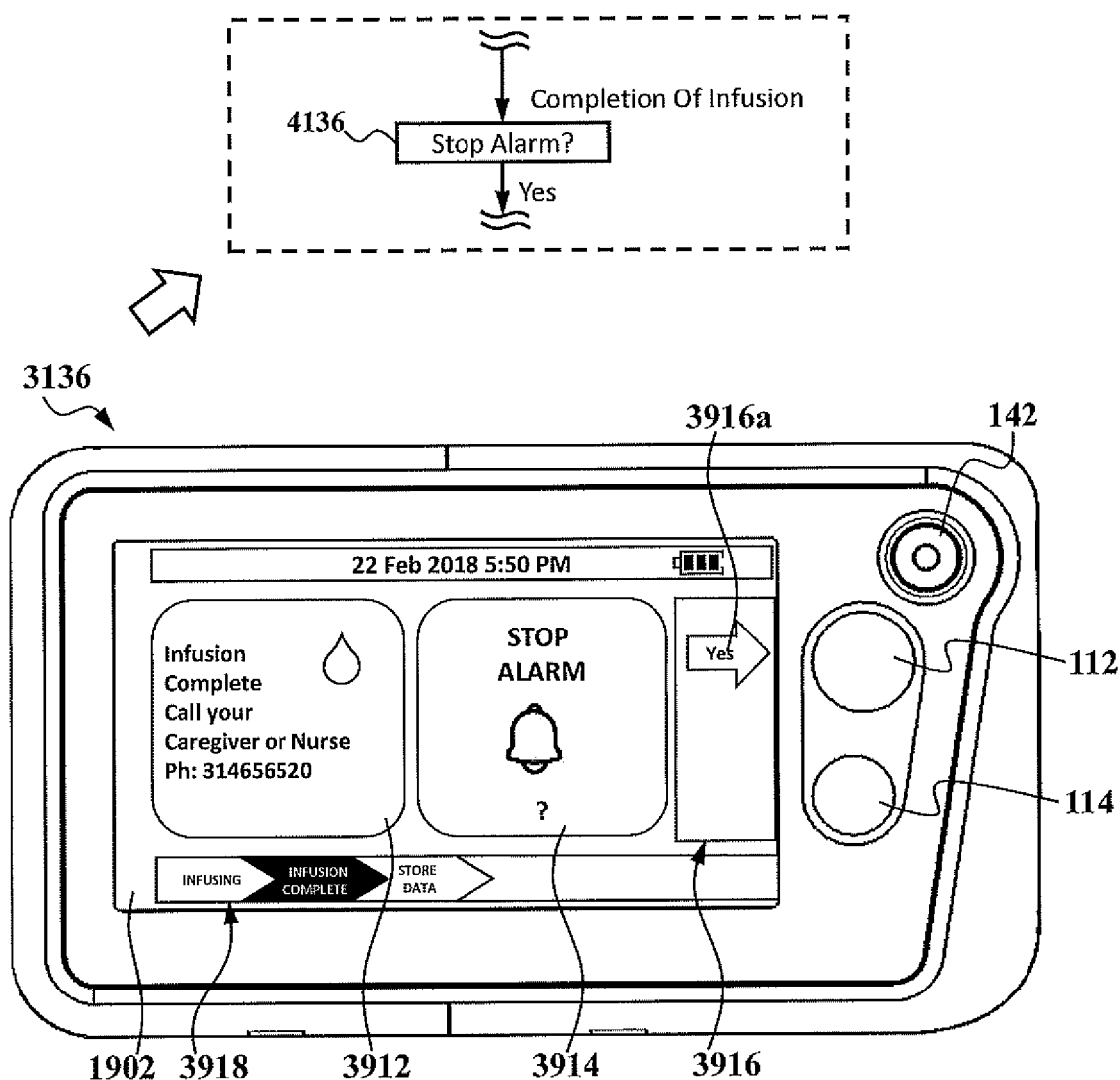

As shown in FIG. 22A, in the fourteenth menu 3136, a message of "Infusion Complete, Call your Caregiver or Nurse" and the contact number entered (e.g. a message of "Ph: 314656520") is shown in the first column 3912 of the screen 1902; a message of "STOP ALARM?" is shown in the second column 3914 of the screen 1902; a "Yes" indicator 3916*a* is shown at the upper part of the third column 3916 of the screen 1902 and pointing to the first (green) button 112. The status is shown as "INFUSION COMPLETE" in the status bar 3918 displayed on the screen 1902.

Upon a user pressing the first (green) button 112 corresponding to the "Yes" indicator 3916*a* in the fourteenth menu 3136, the infusion pump 10 stops the alarm and displays a fifteenth menu 3138 at block 4138 asking a user whether to store infusion data.

Figure 22B:
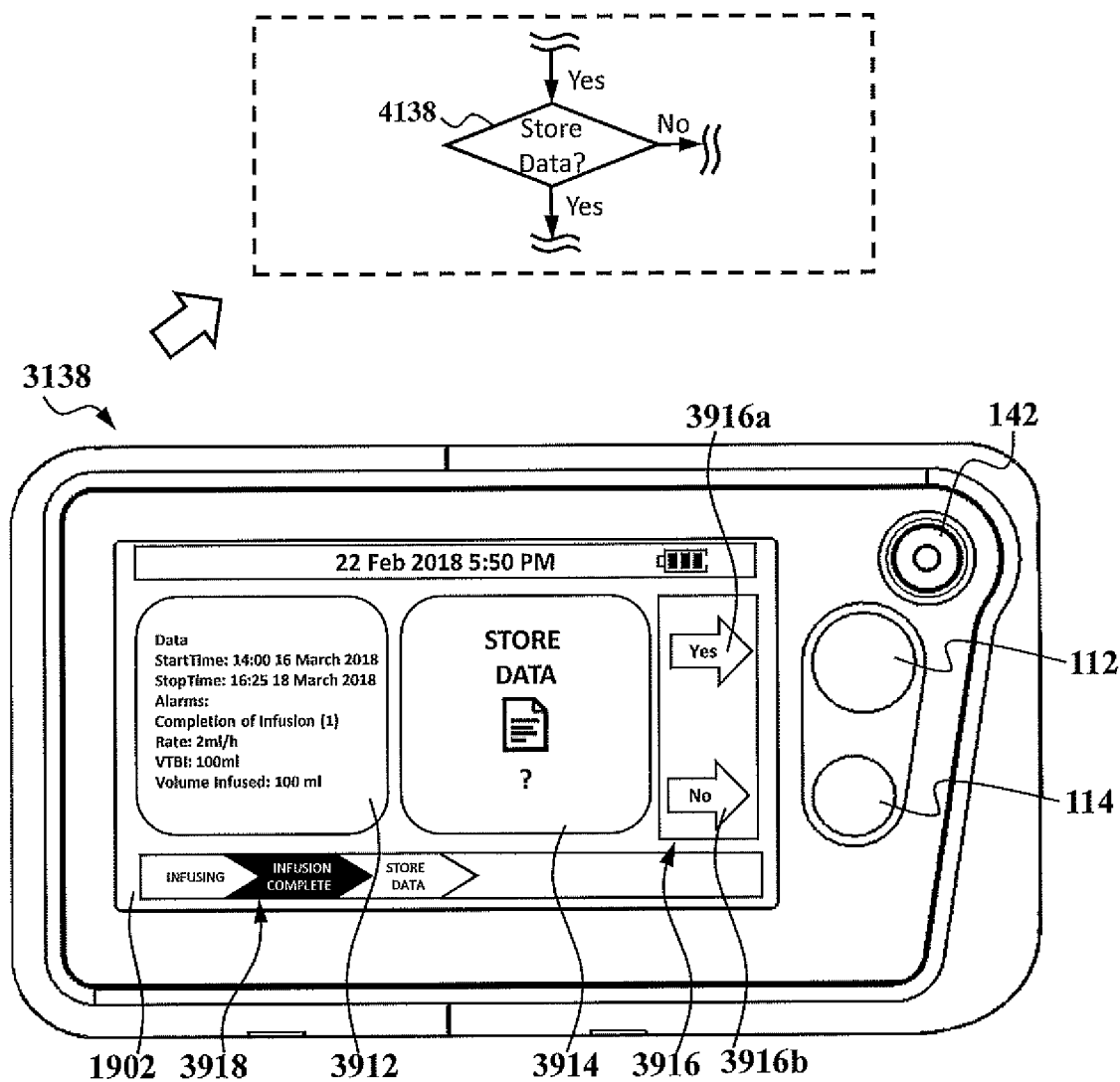

As shown in FIG. 22B, in the fifteenth menu 3138, the infusion data including start time, stop time, time of alarm due to completion of infusion, flow rate, volume to be infused (VTBI), and volume infused (e.g. a message of "Start Time: 14:00 16 Mar. 2018, Stop Time: 16:25 18 Mar. 2018, Alarms: End of Infusion (1), Rate: 2 ml/h, VTBI: 100 ml, Volume Infused: 100 ml"), are shown in the first column 3912 of the screen 1902. A message "STORE DATA?" is shown in the second column 3914 of the screen 1902. A "Yes" indicator 3916*a* is shown at the upper part of the third column 3916 of the screen 1902 and pointing to the first (green) button 112; a "No" indicator 3916b is shown at the lower part of the third column 3916 of the screen 1902 and pointing to the second (red) button 114. The status is shown as "INFUSION COMPLETE" in the status bar 3918 displayed on the screen 1902.

To confirm storing the infusion data, the user presses the first (green) button 112 corresponding to the "Yes" indicator 3916a in the fifteenth menu 3138 upon which, the infusion pump stores the infusion data at block 4140. Upon completion of data storing, the infusion pump ends the infusion process at block 4142.

If no storage of the infusion data is required, the user presses the second (red) button 114 corresponding to the "No" indicator 3916b in the fifteenth menu 3138 upon which, the infusion pump ends process at block 4142 without storing the infusion data.

Insufficient Battery During Cassette Loading

When there is insufficient battery power during process steps such as tube cassette-loading, the infusion pump displays a sixteenth menu 3200 advising/reminding a user to connect to power mains or load a new battery, and followed by removing and reloading the tube cassette.

Figure 23:
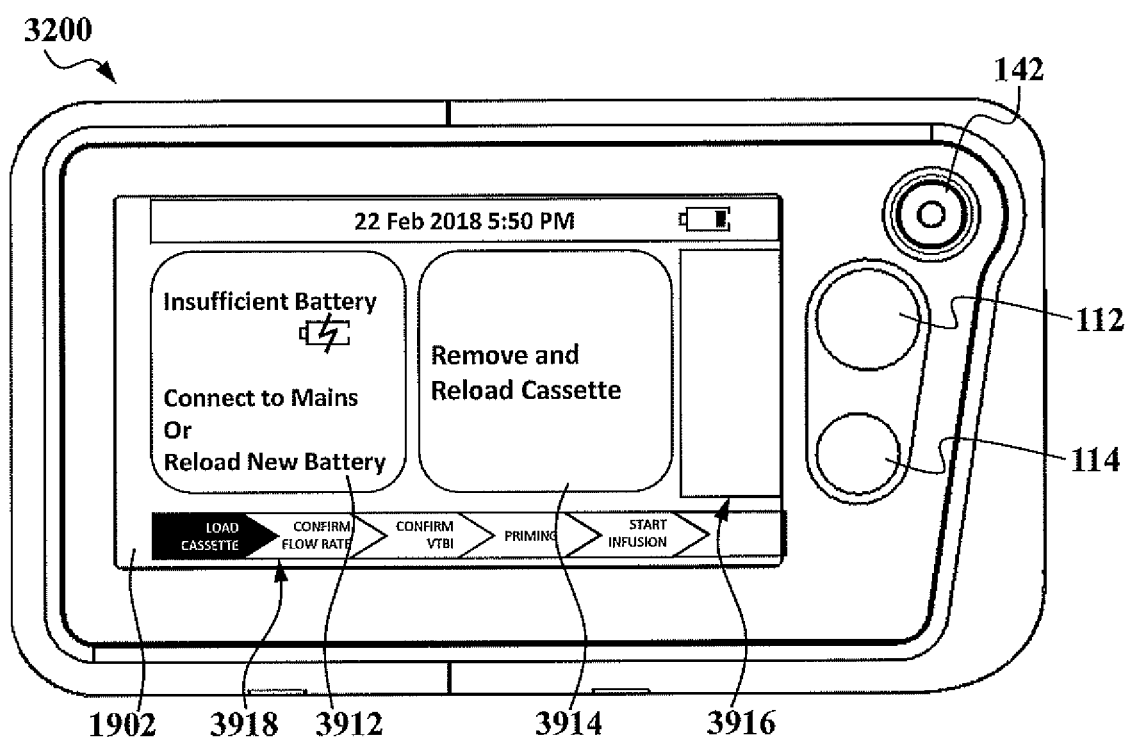

As shown in FIG. 23, in the sixteenth menu 3200, a message of "Insufficient Battery, Connect to Mains Or Reload New Battery" is shown in the first column 3912 of the screen 1902; a message of "Remove and Reload Cassette" is shown in the second column 3914 of the screen 1902; no indicator is shown in the third column 3916 of the screen 1902; the status is shown as "LOAD CASSETTE" in the status bar 3918 displayed on the screen 1902.

Insufficient Battery Power During Infusion

When there is insufficient battery power during the infusing process as indicated at block 4202, the infusion pump triggers the alarm and displays a seventeenth menu 3204 at block 4204, advising/reminding a user to connect to power mains within short period of time, e.g. in 10 minutes, and asking a user whether to stop alarm.

Figure 24A:
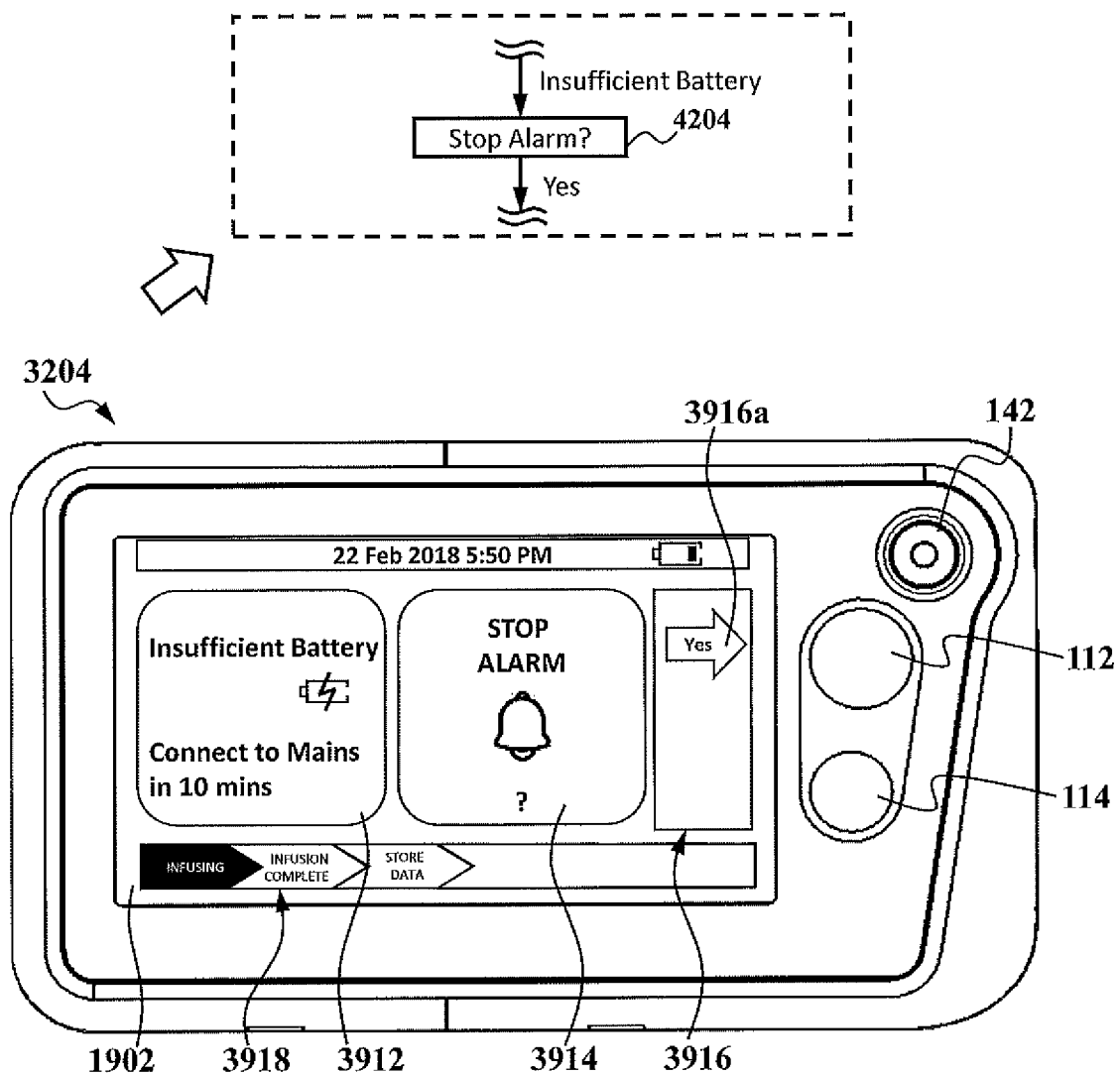

As shown in FIG. 24A, in the seventeenth menu 3204, a message of "Insufficient Battery, Connect to Mains in 10 mins" is shown in the first column 3912 of the screen 1902; a message of "STOP ALARM?" is shown in the second column 3914 of the screen 1902; a "Yes" indicator 3916a is shown at the upper part of the third column 3916 of the screen 1902 and pointing to the first (green) button 112. The status is shown as "INFUSING" in the status bar 3918 displayed on the screen 1902.

Upon the infusion pump being connected to the power mains and alarm stopped by a user pressing the first (green) button 112 corresponding to the "Yes" indicator 3916a in the seventeenth menu 3204, the infusion pump stops the alarm and displays an eighteenth menu 3206 at block 4206, showing a message that a new battery has been connected and asking a user whether to resume the infusion with previous infusion setup data.

Figure 24B:
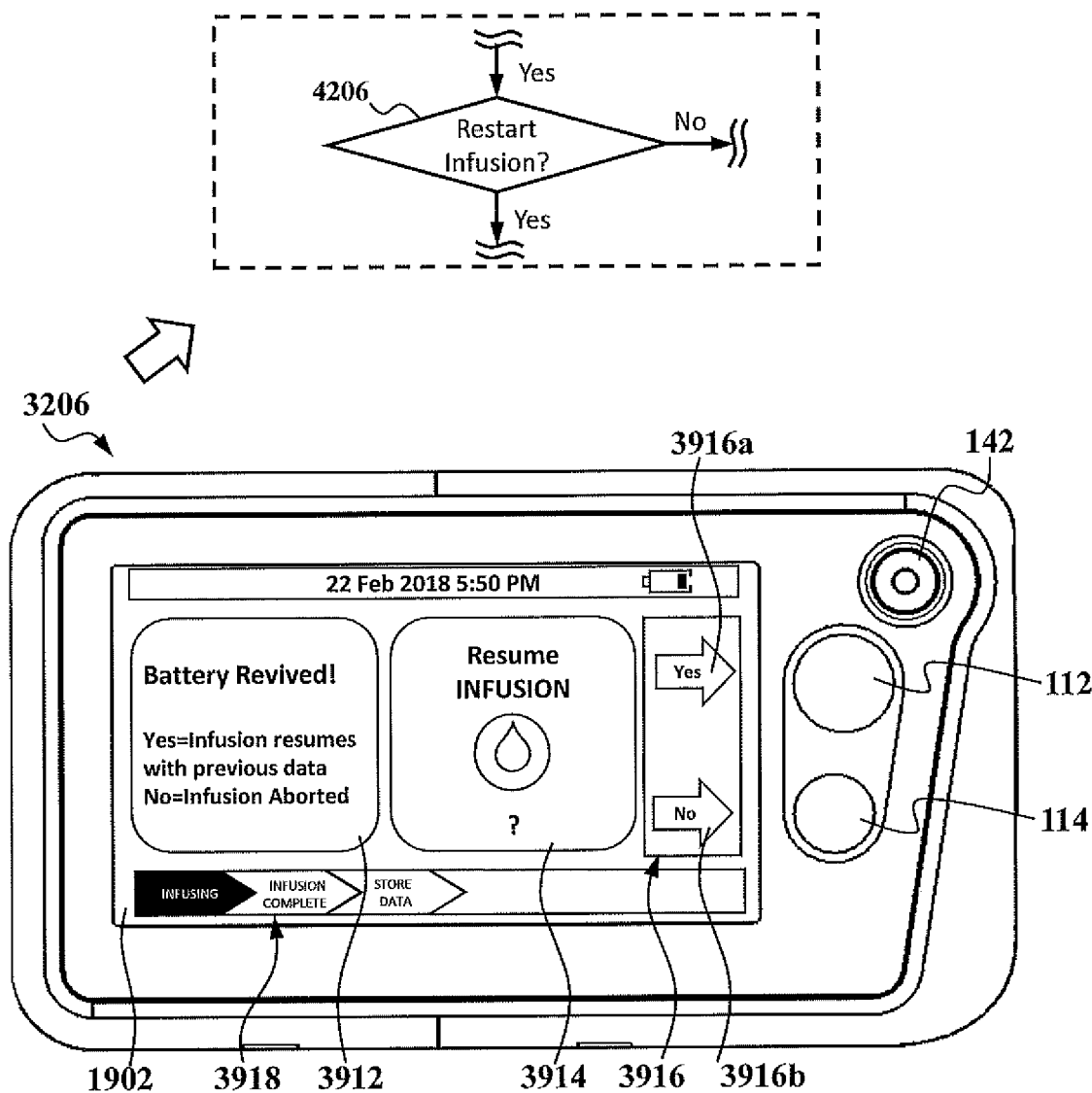

As shown in FIG. 24B, in the eighteenth menu 3206, a message of "Battery Received! Yes=Infusion resumes with previous data, No=Infusion Aborted" is shown in the first column 3912 of the screen 1902; a message of "Resume INFUSION?" is shown in the second column 3914 of the screen 1902; a "Yes" indicator 3916a is shown at the upper part of the third column 3916 of the screen 1902 and pointing to the first (green) button 112; and a "No" indicator 3916b is shown at the lower part of the third column 3916 of the screen 1902 and pointing to the second (red) button 114. The status is shown as "INFUSING" in the status bar 3918 displayed on the screen 1902.

If the infusion needs not be resumed, the user presses the second (red) button 114 corresponding to the "No" indicator 3916b in the eighteenth menu 3206, the infusion pump aborts infusion at block 4208.

If the infusion is to be resumed, the user presses the first (green) button 112 corresponding to the "Yes" indicator 3916a in the eighteenth menu 3206, the infusion pump 10 resumes the infusion with the previous infusion data at block 4210.

Upon completion of the infusion, the infusion pump proceeds with steps at block 4250 with respect to the completion of the infusion and the data storing. The steps at block 4250 are the same as the steps at block 4150.

Air in Line Detected During Priming

Figure 11:
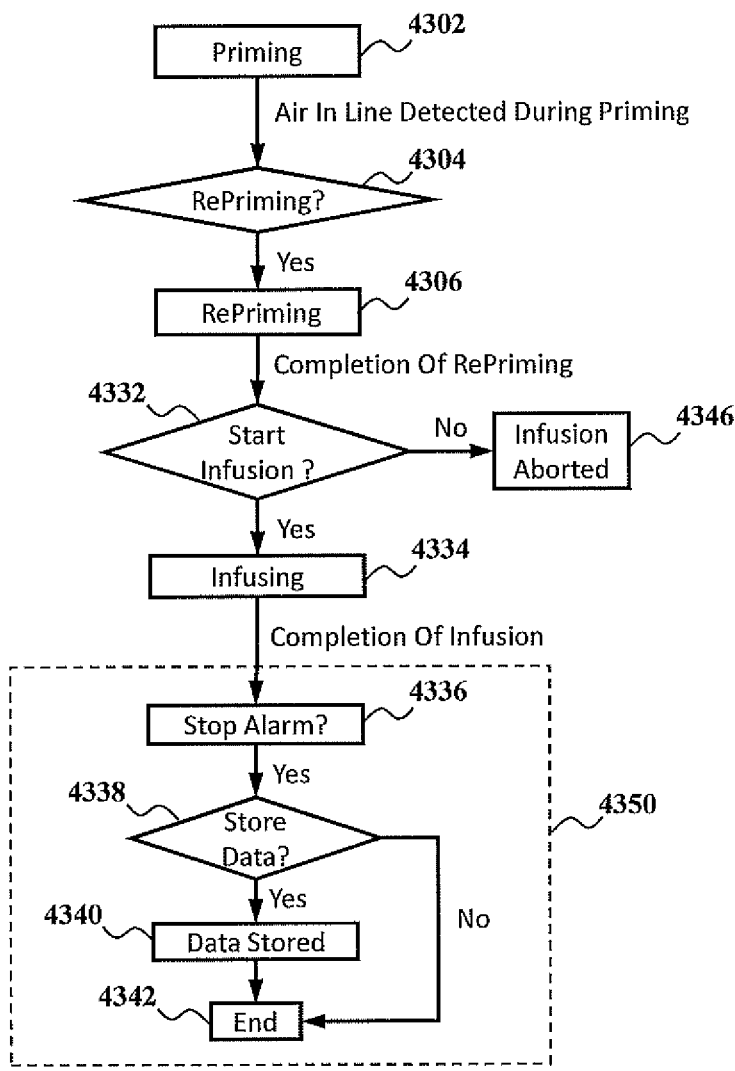
FIGS. 11 to 14 are flowcharts showing some of the detailed steps the method illustrated in FIG. 10.

As shown in FIG. 11, when "air in line" is detected during priming, as shown at block 4302, the infusion pump displays a nineteenth menu 3304 at block 4304 informing a user the "air in line" situation, reminding the user to disconnect patient from line before re-priming, and asking the user to confirm whether to start re-priming.

Figure 25:
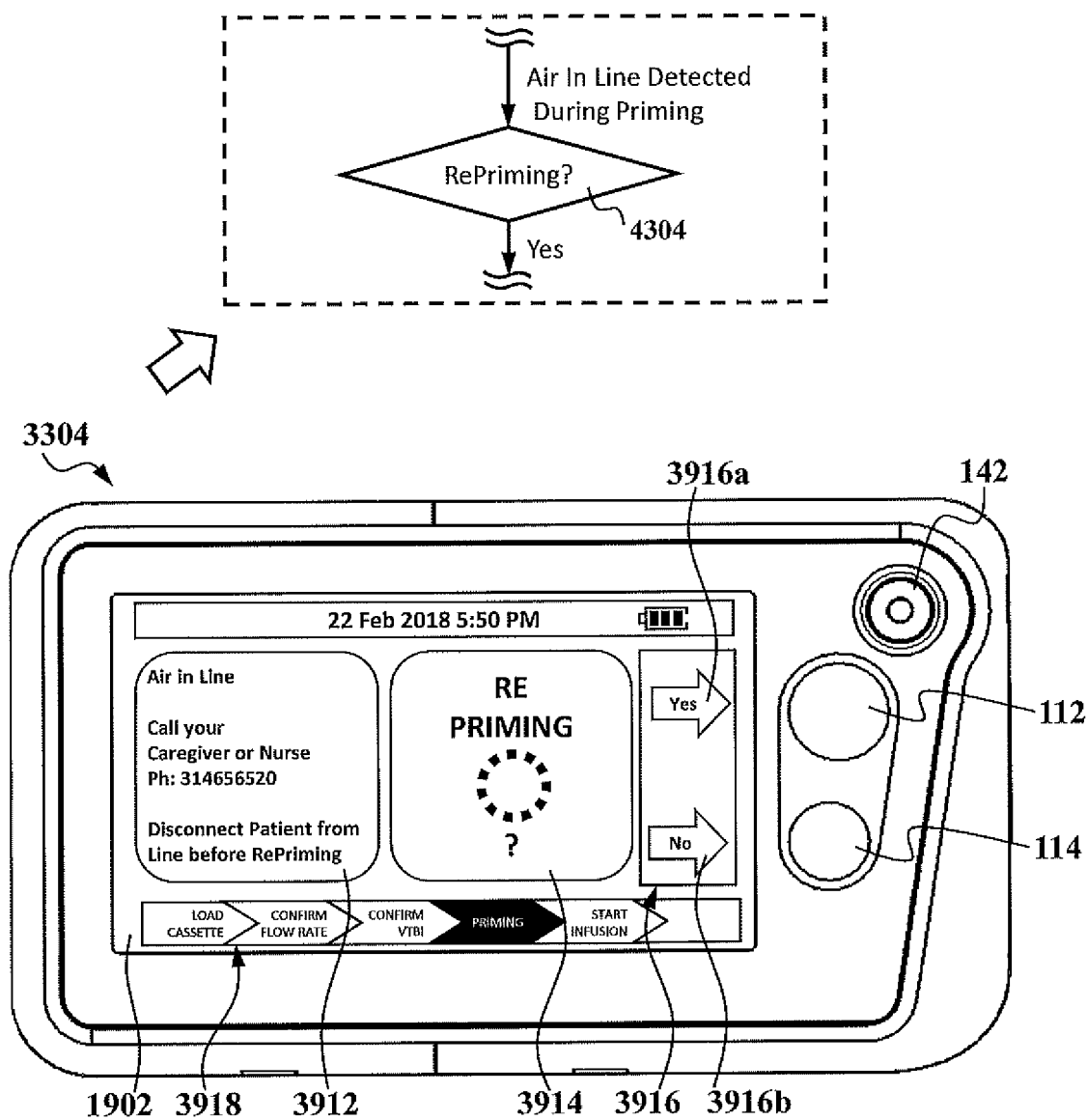

As shown in FIG. 25, in the nineteenth menu 3304, a message "Air in Line, Call your Caregiver or Nurse", the contact number entered (e.g. a message of "Ph: 314656520"), Disconnect Patient from Line before RePriming" is shown in the first column 3912 of the screen 1902. A message "REPRIMING?" is shown in the second column 3914 of the screen 1902; a "Yes" indicator 3916a is shown at the upper part of the third column 3916 of the screen 1902 and pointing to the first (green) button 112; a "No" indicator 3916b is shown at the lower part of the third column 3916 of the screen 1902 and pointing to the second (red) button 114. The status is shown as "PRIMING" in the status bar 3918 displayed on the screen 1902.

Upon a user pressing the first (green) button 112, the infusion pump starts repriming.

Upon completion of repriming, the infusion pump displays the twelfth menu 3132 at block 4332, asking a user to confirm whether to start infusion (the twelfth menu 3132 is as shown in FIG. 20).

Upon a user pressing the first (green) button, the infusion pump starts infusion, and displays the thirteenth menu 3134 for showing the infusion information. In the meantime, the first and second buttons are disabled, as shown at block 4334 (the thirteenth menu 3134 is as shown in FIG. 21)., to prevent data input into the infusion pump.

Upon completion of infusion, the infusion pump proceeds with steps at block 4350 with respect to the completion of the infusion and data storing. The steps at block 4350 are the same as the steps at block 4150.

Air in Line Detected During Infusing

Figure 12:
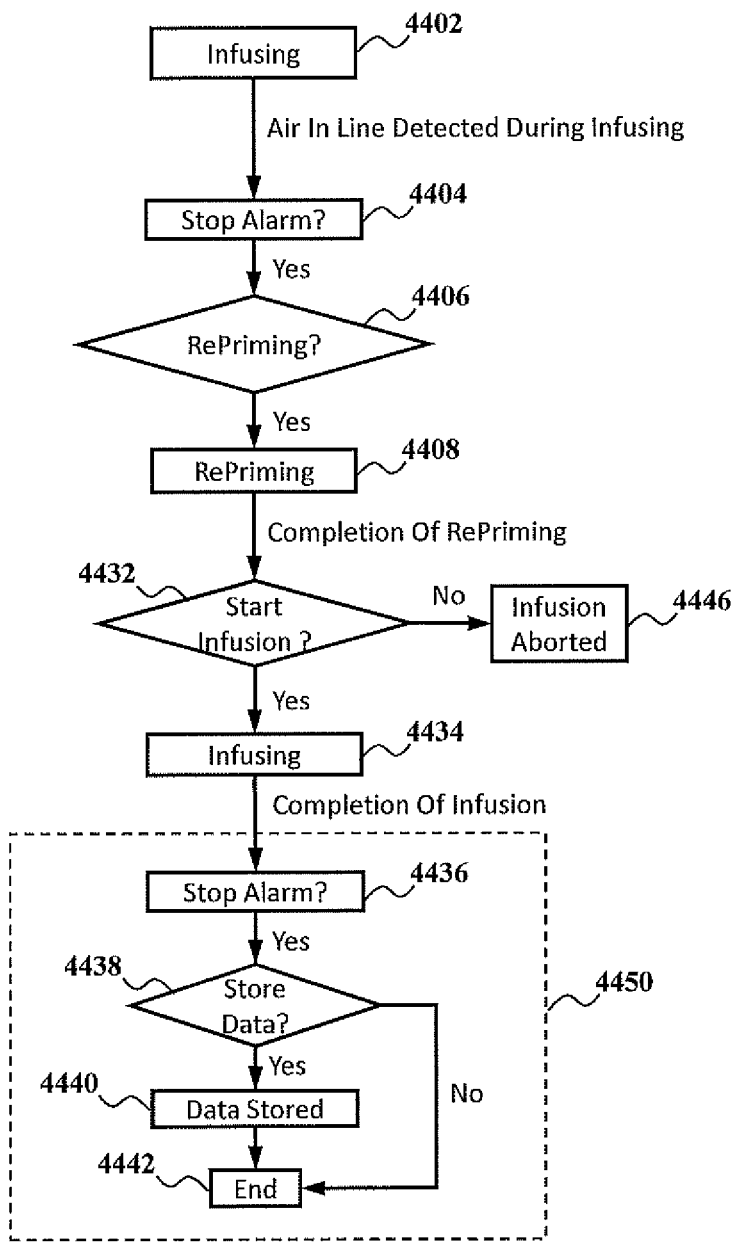

As shown in FIG. 12, when air in line is detected during infusion as shown at block 4402, the infusion pump stops the infusion, enables the first and second buttons, triggers the alarm and displays a twentieth menu 3404 at block 4404, informing that air in line has been detected during infusion, and asking the user whether to stop alarm.

Figure 26A:
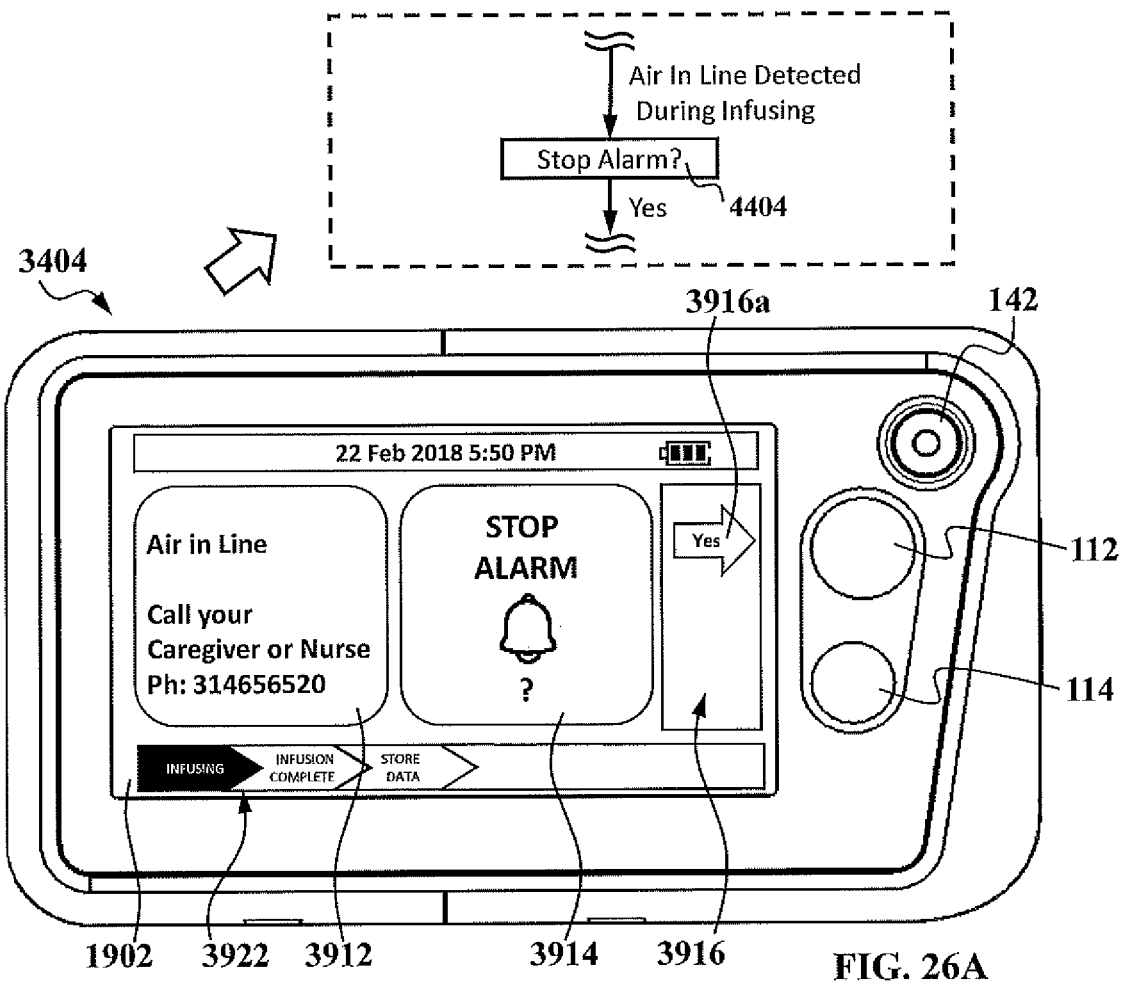

As shown in FIG. 26A, in the twentieth menu 3404, a message "Air in Line, Call your Caregiver or Nurse" together with the contact number entered (e.g. a message of "Ph: 314656520")" is shown in the first column 3912 of the screen 1902; a message "STOP ALARM?" is shown in the second column 3914 of the screen 1902; a "Yes" indicator 3916a is shown at the upper part of the third column 3916 of the screen 1902 and pointing to the first (green) button 112; the status is shown as "INFUSING" in the status bar 3918 displayed on the screen 1902.

Upon a user pressing the first (green) button 112, the infusion pump stops the alarm and displays a twenty-first menu 3406 at block 4406 informing that air in line has been detected during infusion, asking a user to confirm whether to start repriming, and reminding a user to disconnect the patient from line before the repriming.

Figure 26B:
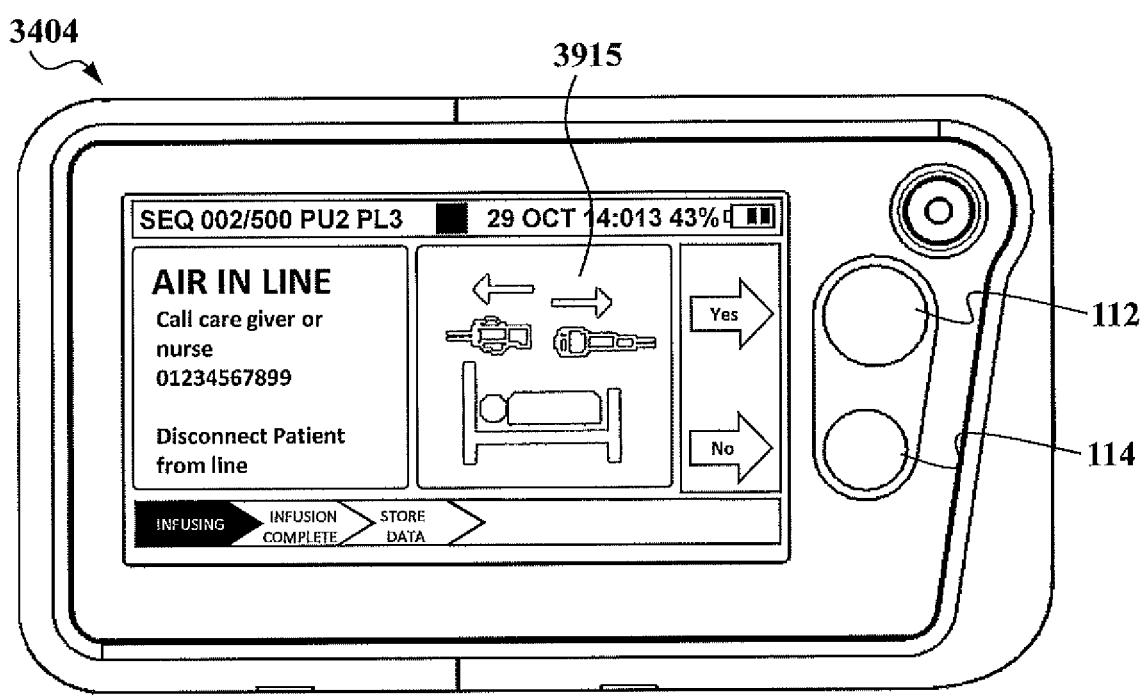
Figure 26C:
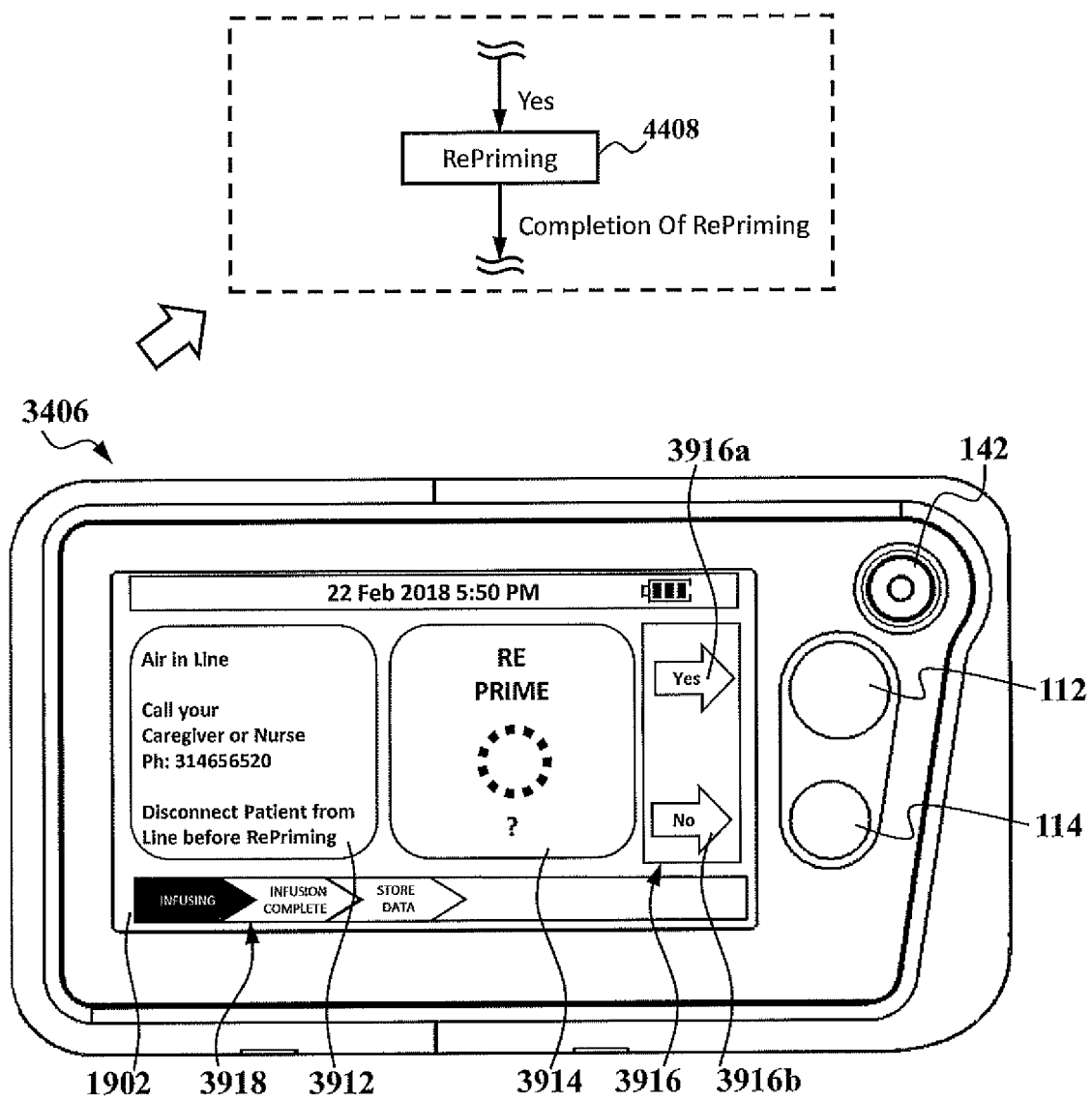

As shown in FIG. 26B, in the twenty-first menu 3406, a message of "Air in Line, Call your Caregiver or Nurse" and the contact number entered (e.g. a message of "Ph: 314656520"), Disconnect Patient from Line before RePriming" is shown in the first column 3912 of the screen 1902; a message of "REPRIME?" is shown in the second column 3914 of the screen 1902; a "Yes" indicator 3916a is shown at the upper part of the third column 3916 of the screen 1902 and pointing to the first (green) button 112; a "No" indicator 3916b is shown at the lower part of the third column 3916 of the screen 1902 and pointing to the second (red) button 114. The status is shown as "INFUSING" in the status bar 3918 displayed on the screen 1902.

Upon a user pressing the first (green) button 112, the infusion pump starts repriming at block 4408.

Upon completion of repriming, the infusion pump displays a twelfth menu 3132 at block 4432 asking the user to confirm whether to start infusion (the twelfth menu 3132 is as shown in FIG. 20).

If a user presses the second (red) button 114 corresponding to the "No" indicator 3916b in the twelfth menu 3132, the infusion pump aborts the infusion process at block 4446.

If a user presses the first (green) button 112 corresponding to the "Yes" indicator 3916a in the twelfth menu 3132, the infusion pump starts infusion, displays a thirteenth menu 3134 showing the infusion information, and disables the first and second buttons at block 4434 (the thirteenth menu 3134 is as shown in FIG. 21).

Upon completion of infusion, the infusion pump proceeds with steps at block 4450 with respect to the completion of the infusion and the data storing. The steps at block 4450 are the same as the steps at block 4150.

Occlusion at Upper Tube Detected during Infusion

Figure 13:
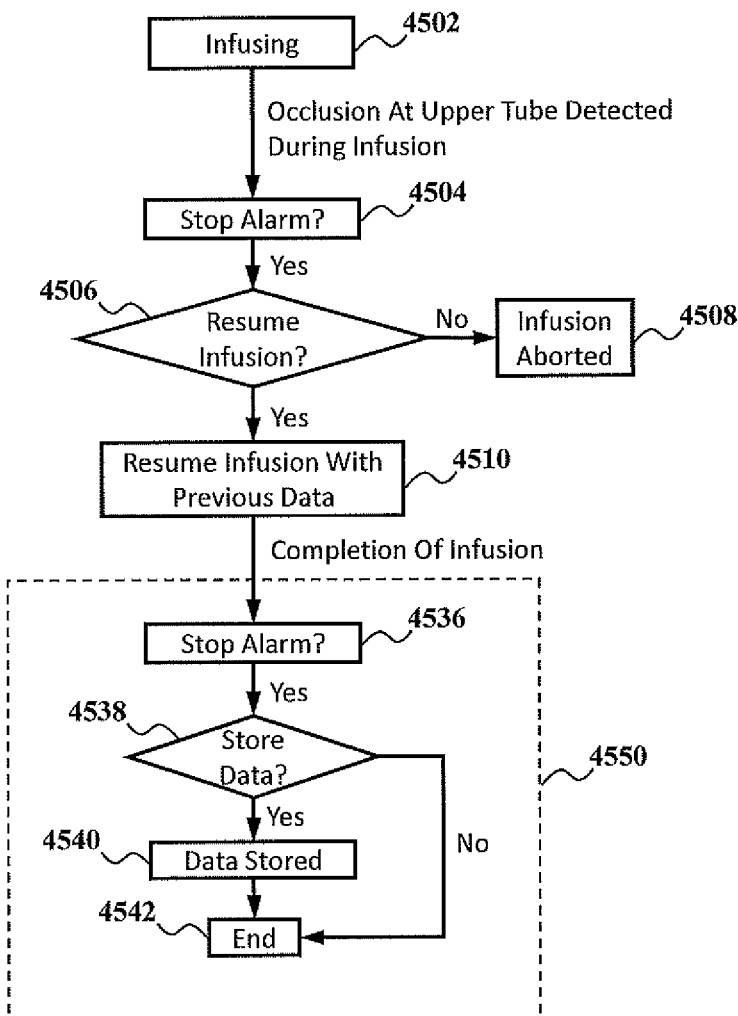

As shown in FIG. 13, if an occlusion at an upper tube segment of the tube cassette is detected during infusion, as indicated at block 4502, the infusion pump stops the infusion, enables the first and second buttons, triggers the alarm and displays a twenty-second menu 3504 at block 4504 informing that occlusion at the upper tube has been detected during infusion, and asking a user whether to stop alarm.

Figure 27A:
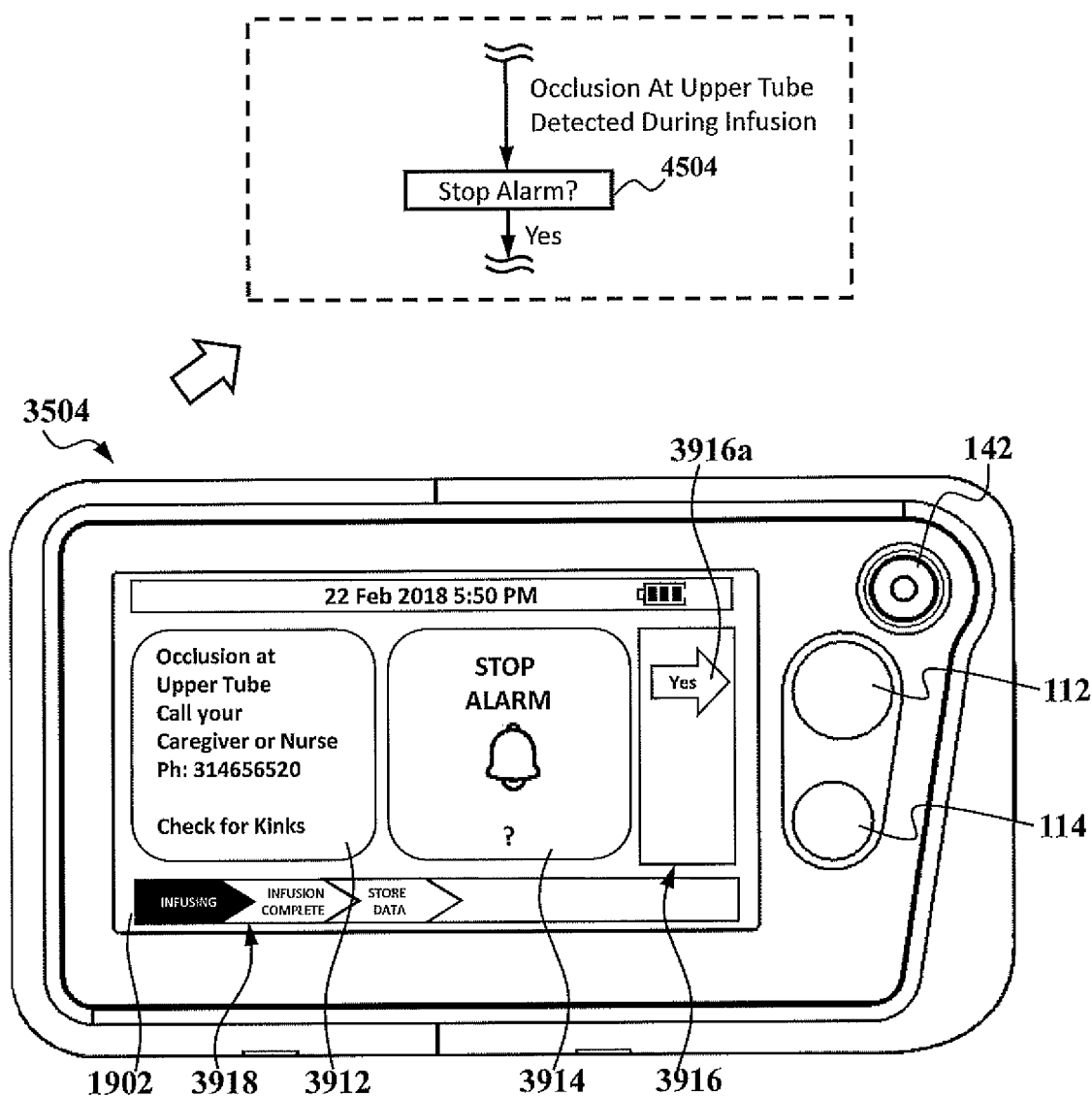

As shown in FIG. 27A, in the twenty-second menu 3504, a message of "Occlusion at Upper Tube, Call your Caregiver or Nurse" and the contact number entered (e.g. a message of "Ph: 314656520"), Check for Kinks" is shown in the first column 3912 of the screen 1902; a message of "STOP ALARM?" is shown in the second column 3914 of the screen 1902; a "Yes" indicator 3916a is shown at the upper part of the third column 3916 of the screen 1902 and pointing to the first (green) button 112. The status is shown as "INFUSING" in the status bar 3918 displayed on the screen 1902.

Upon a user pressing the first (green) button 112 corresponding to the "Yes" indicator 3916a in the twenty-second menu 3504, the infusion pump stops the alarm and displays a twenty-third menu 3506 at block 4506 informing that occlusion at the upper tube has been detected during infusion, reminding a user to check for kinks and request confirmation whether to resume infusion with previous data.

Figure 27B:
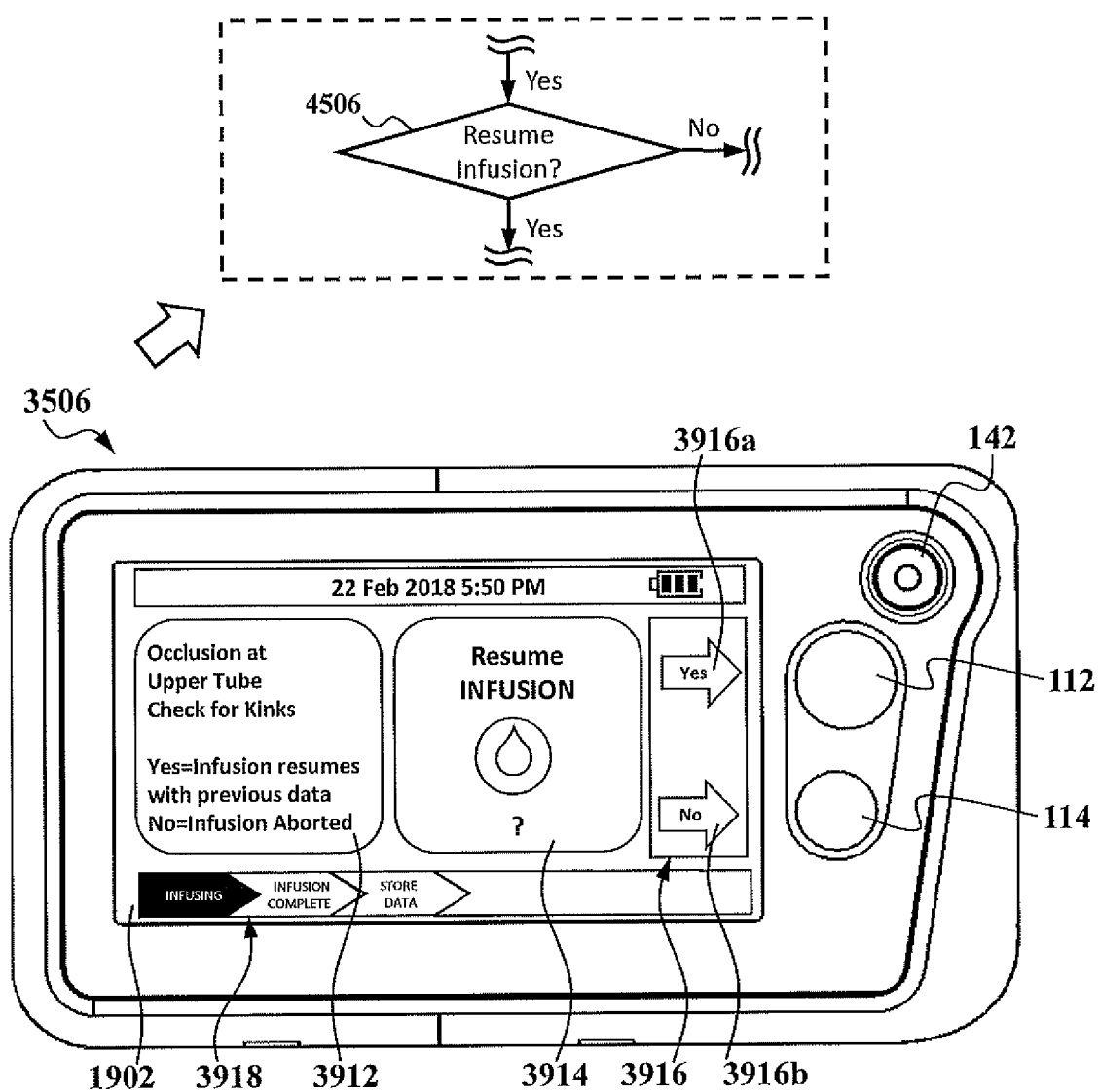

As shown in FIG. 27B, in the twenty-third menu 3506, a message of "Occlusion at Upper Tube, Check for Kinks, Yes=Infusion resumes with previous data, No=Infusion Aborted" is shown in the first column 3912 of the screen 1902; a message of "Resume INFUSION?" is shown in the second column 3914 of the screen 1902; a "Yes" indicator 3916a is shown at the upper part of the third column 3916 of the screen 1902 and pointing to the first (green) button 112; a "No" indicator 3916b is shown at the lower part of the third column 3916 of the screen 1902 and pointing to the second (red) button 114. The status is shown as "INFUSING" in the status bar 3918 displayed on the screen 1902.

If the infusion is not to be resumed, a user presses the second (red) button 114 corresponding to the "No" indicator 3916b in the twenty-third menu 3506. The infusion pump then aborts the infusion at block 4508.

If the infusion is to be resumed, a user presses the first (green) button 112 corresponding to the "Yes" indicator 3916a in the twenty-third menu 3506. The infusion pump resumes the infusion with the previous data at block 4510.

Upon completion of the infusion, the infusion pump proceeds with steps at block 4550 with respect to the completion of infusion and the data storing. The steps at block 4550 are the same as the steps at block 4150.

Occlusion at Lower Tube Detected During Infusion

Figure 14:
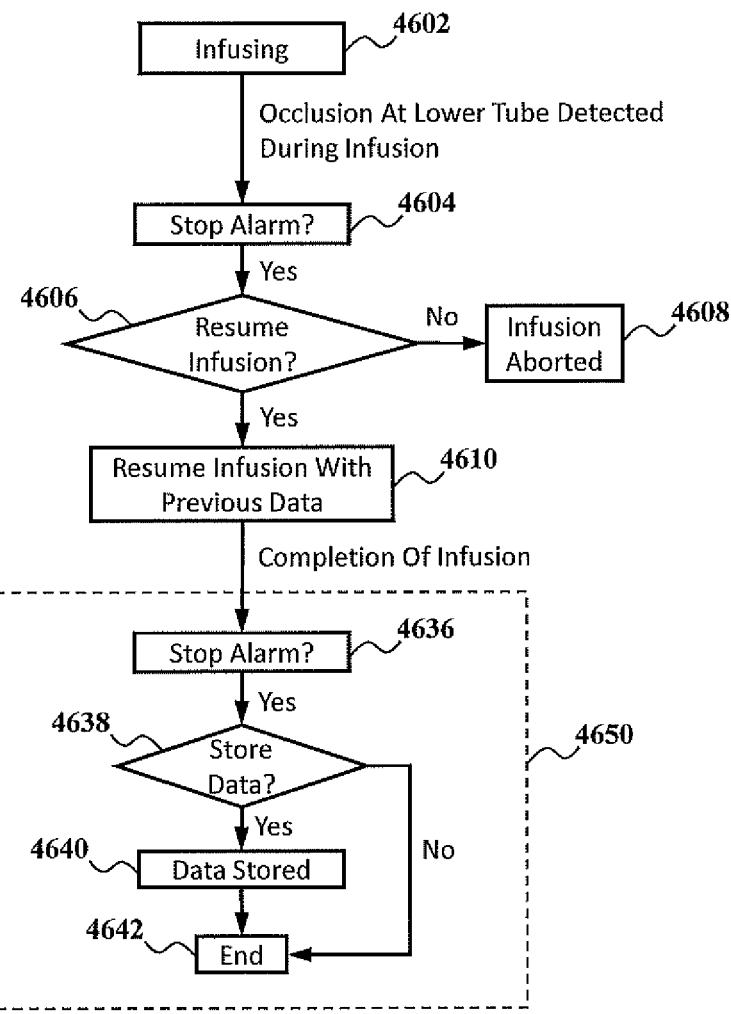

As shown in FIG. 14, if an occlusion at a lower tube segment of the tube cassette is detected during infusion at block 4602, the infusion pump stops the infusion, enables the first and second buttons, triggers the alarm and displays a twenty-fourth menu 3604 at block 4604 informing that the occlusion at the lower tube has been detected during the infusing, and asking a user whether to stop alarm.

Figure 27C:
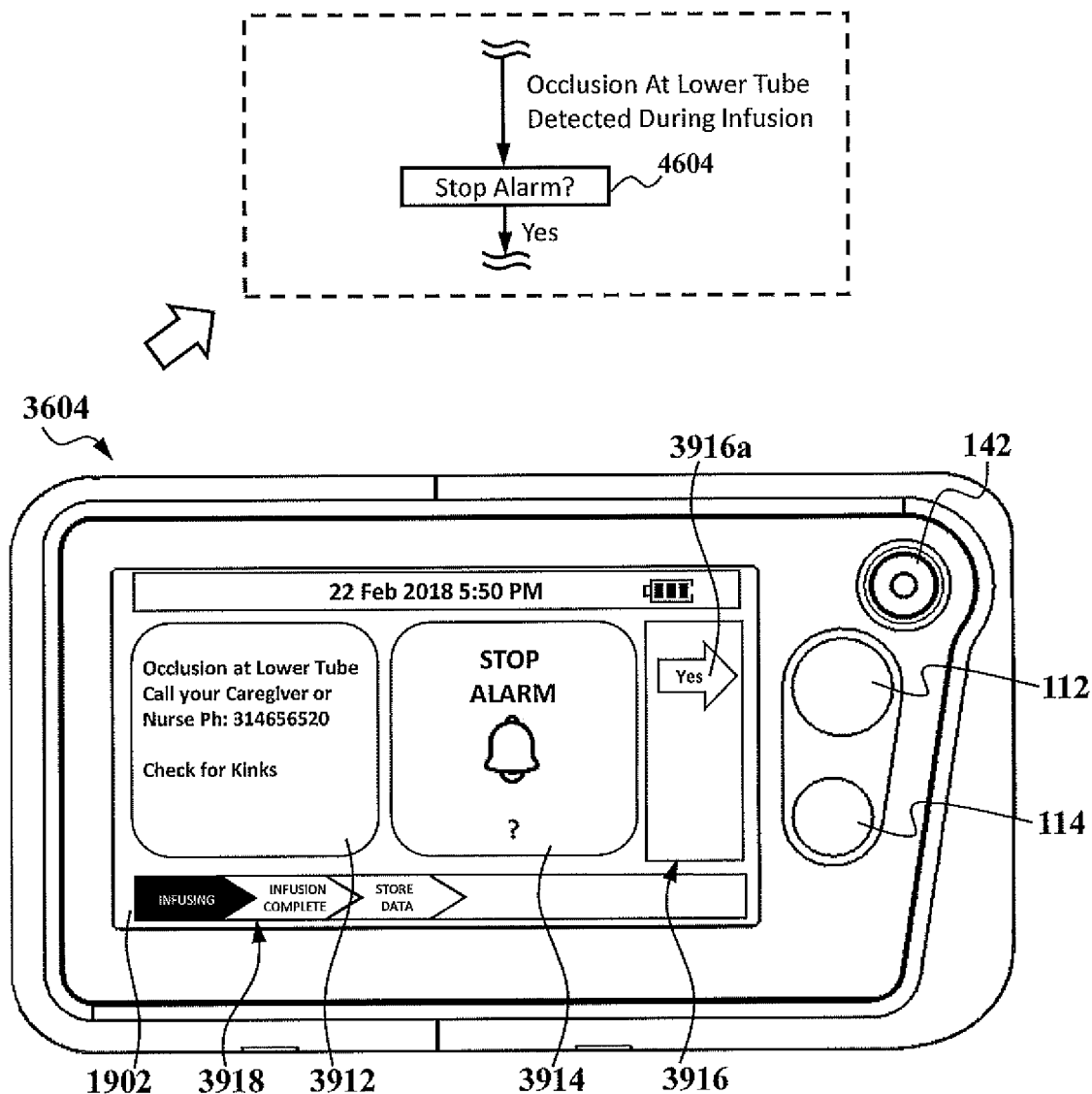

As shown in FIG. 27C, in the twenty-fourth menu 3604, a message "Occlusion at Lower Tube, Call your Caregiver or Nurse" and the contact number entered (e.g. a message of "Ph: 314656520"), Check for Kinks" is shown in the first column 3912 of the screen 1902; a message of "STOP ALARM?" is shown in the second column 3914 of the screen 1902; a "Yes" indicator 3916a is shown at the lower part of the third column 3916 of the screen 1902 and pointing to the first (green) button 112. The status is shown as "INFUSING" in the status bar 3918 displayed on the screen 1902.

Upon a user pressing the first (green) button 112 corresponding to the "Yes" indicator 3916a in the twenty-fourth menu 3604, the infusion pump stops the alarm and displays a twenty-fifth menu 3606 at block 4606 informing that the occlusion at the lower tube segment of the tube cassette has been detected during the infusion process, reminding a user to check for kinks and asking a user to confirm resuming the infusion with previous data.

Figure 27D:
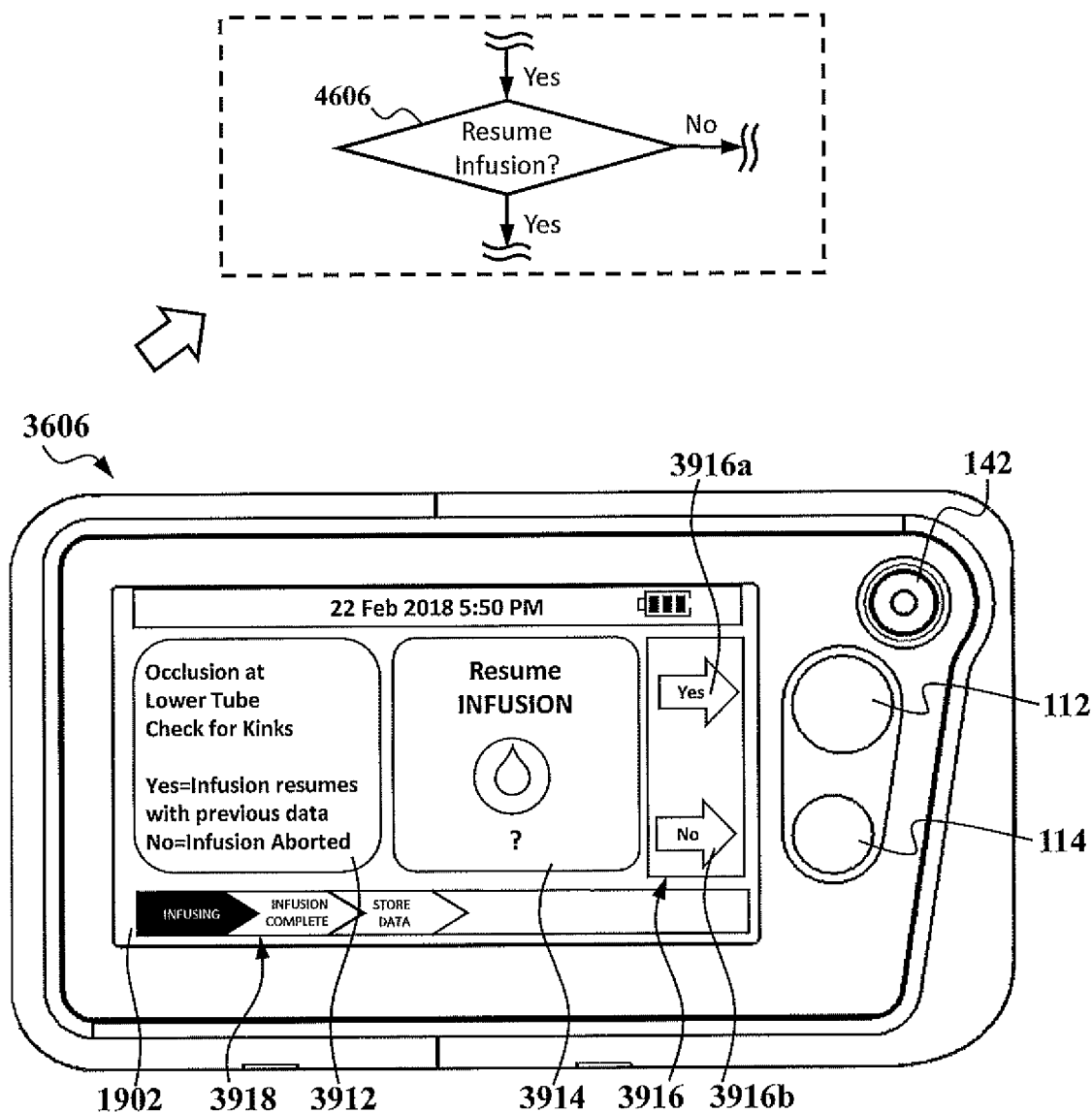
Figure 28:
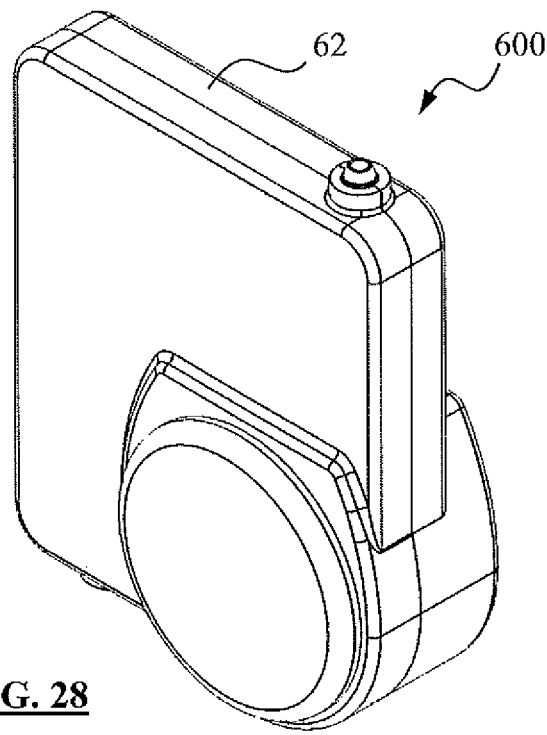
FIG. 28 is a perspective view showing a tube cassette for use in an infusion pump according to one embodiment of the present invention.
Figure 29:
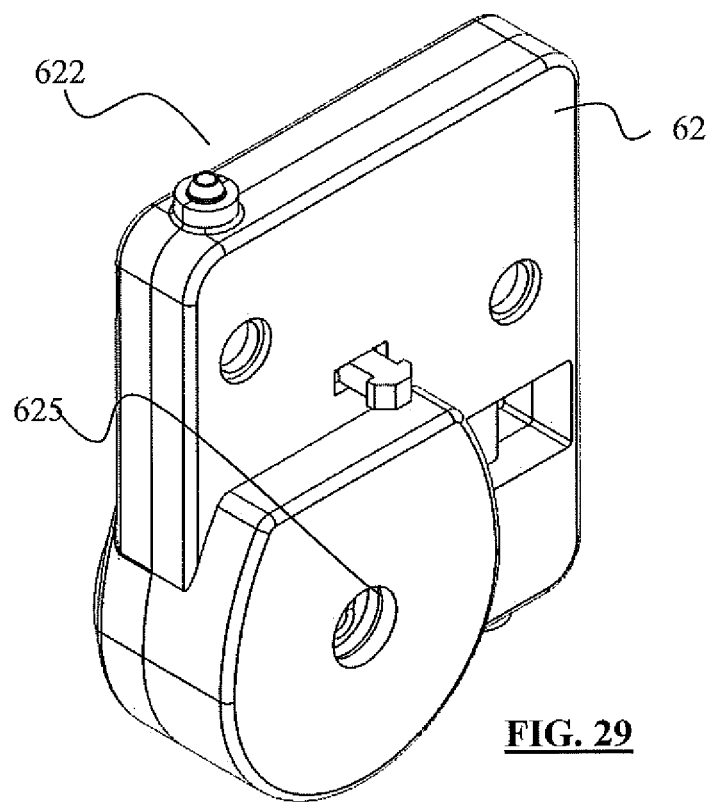
FIG. 29 is a perspective back view of the tube cassette shown in FIG. 28.
Figure 30:
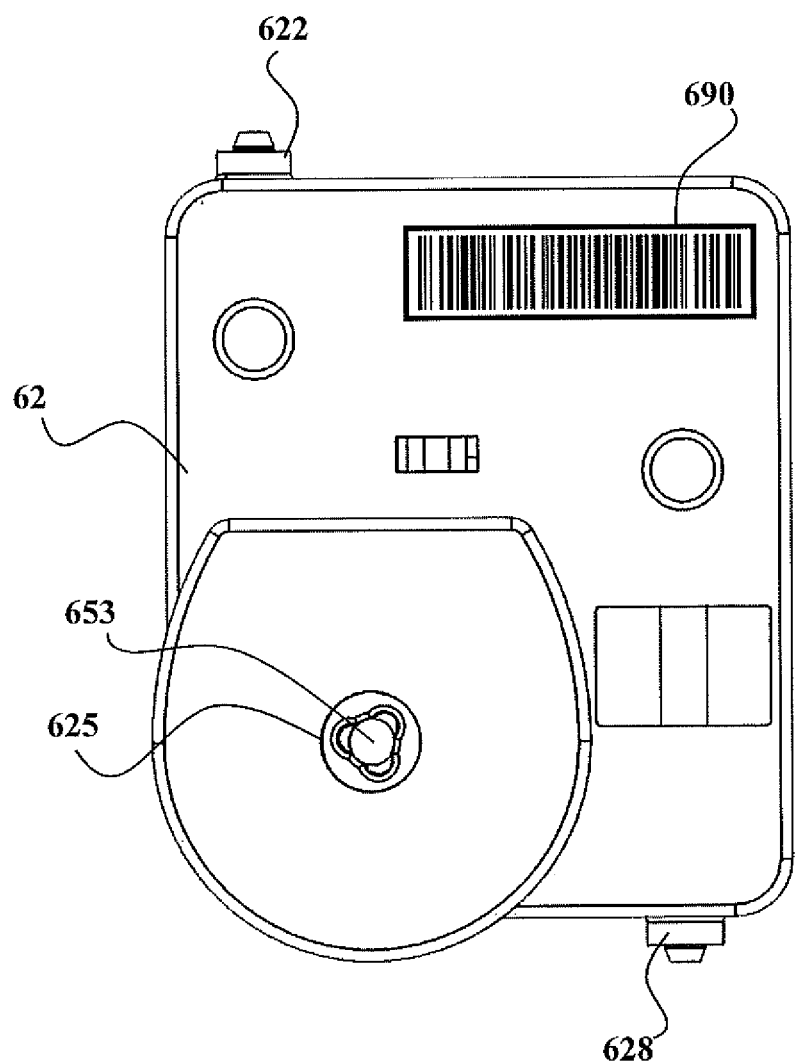
FIG. 30 is a back view of FIG. 28.
Figure 31:
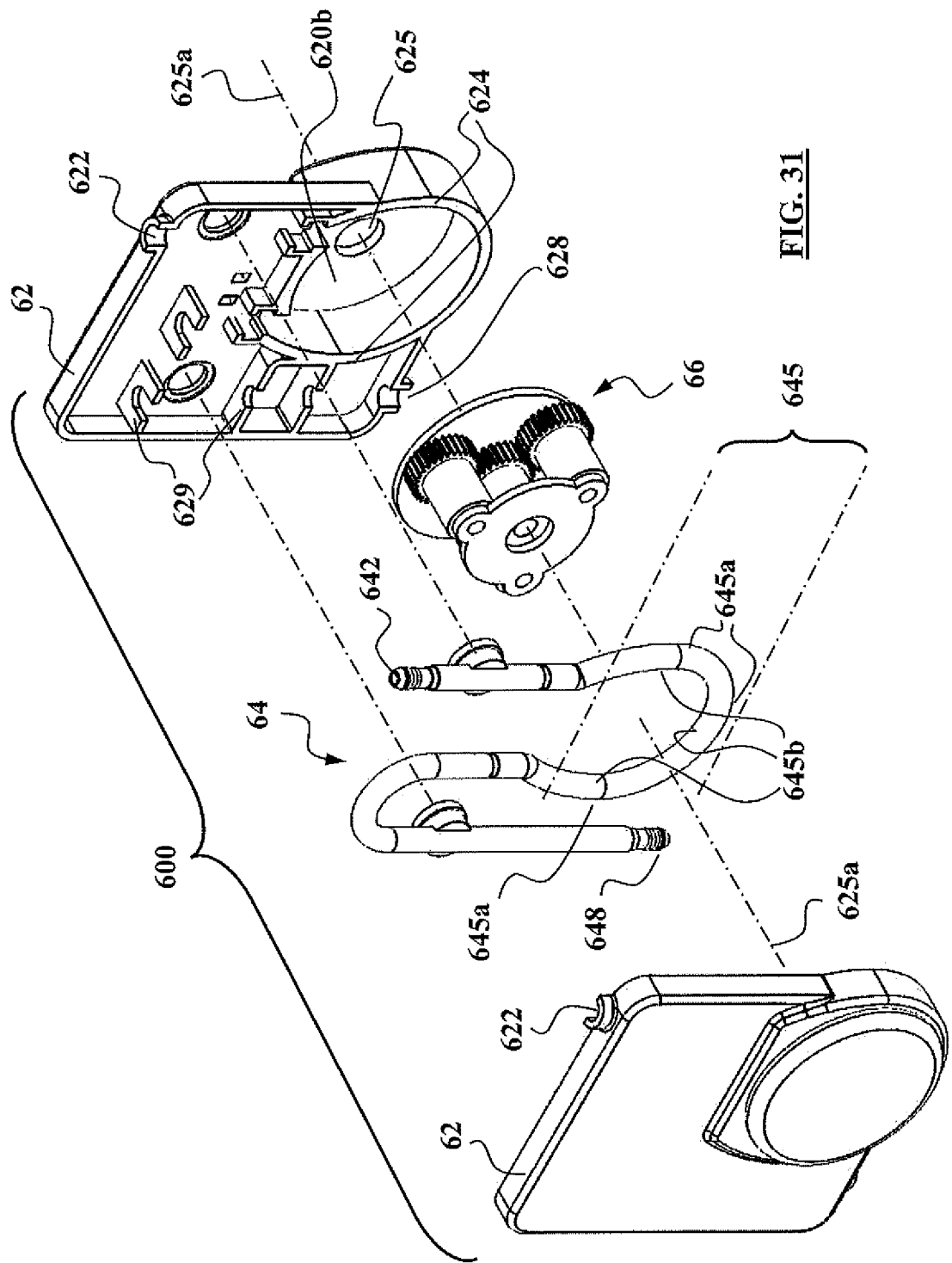
FIG. 31 is an exploded view of FIG. 28.
Figure 32:
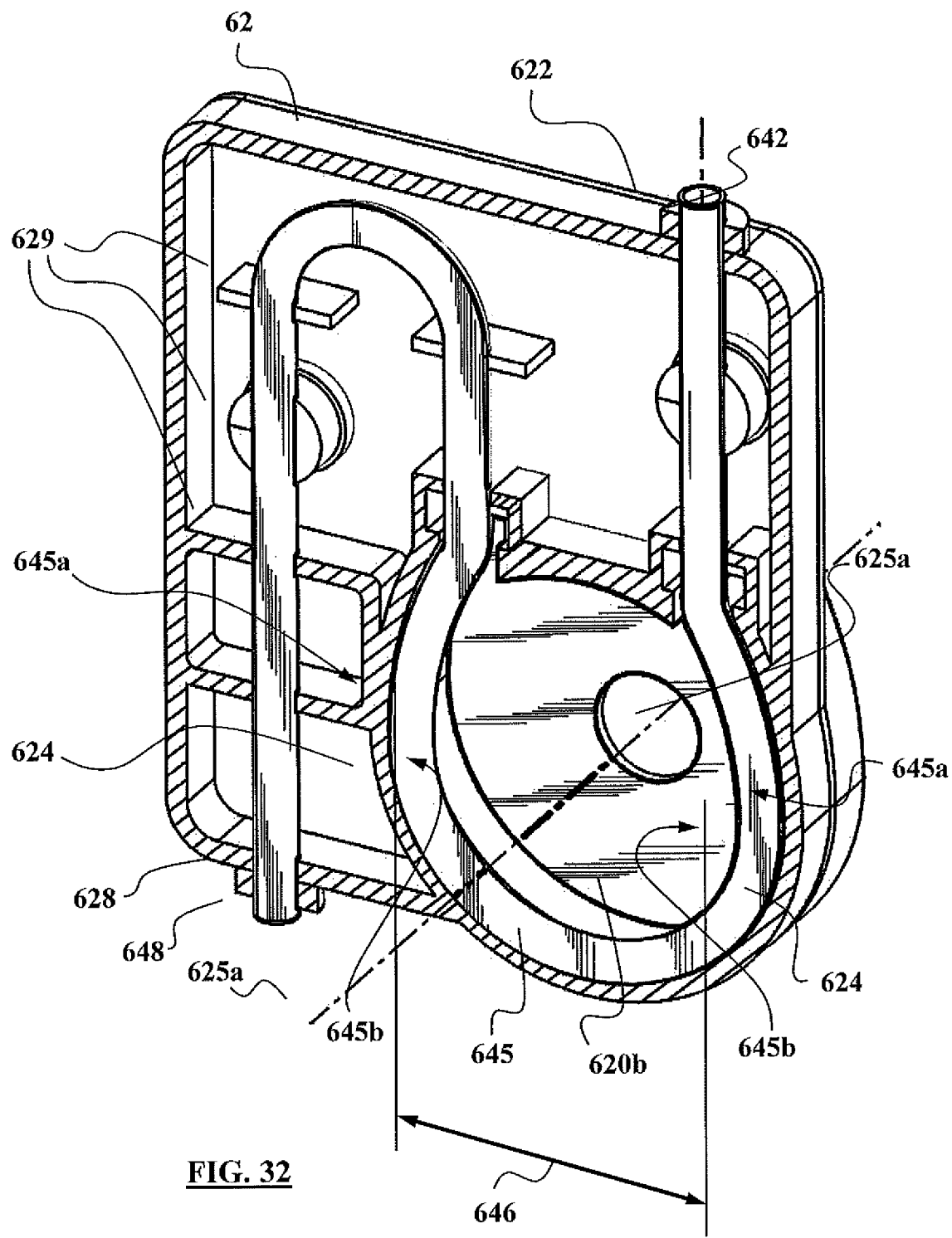
FIG. 32 is a perspective view showing a housing and a tube of the tube cassette shown in FIG. 28.
Figure 33:
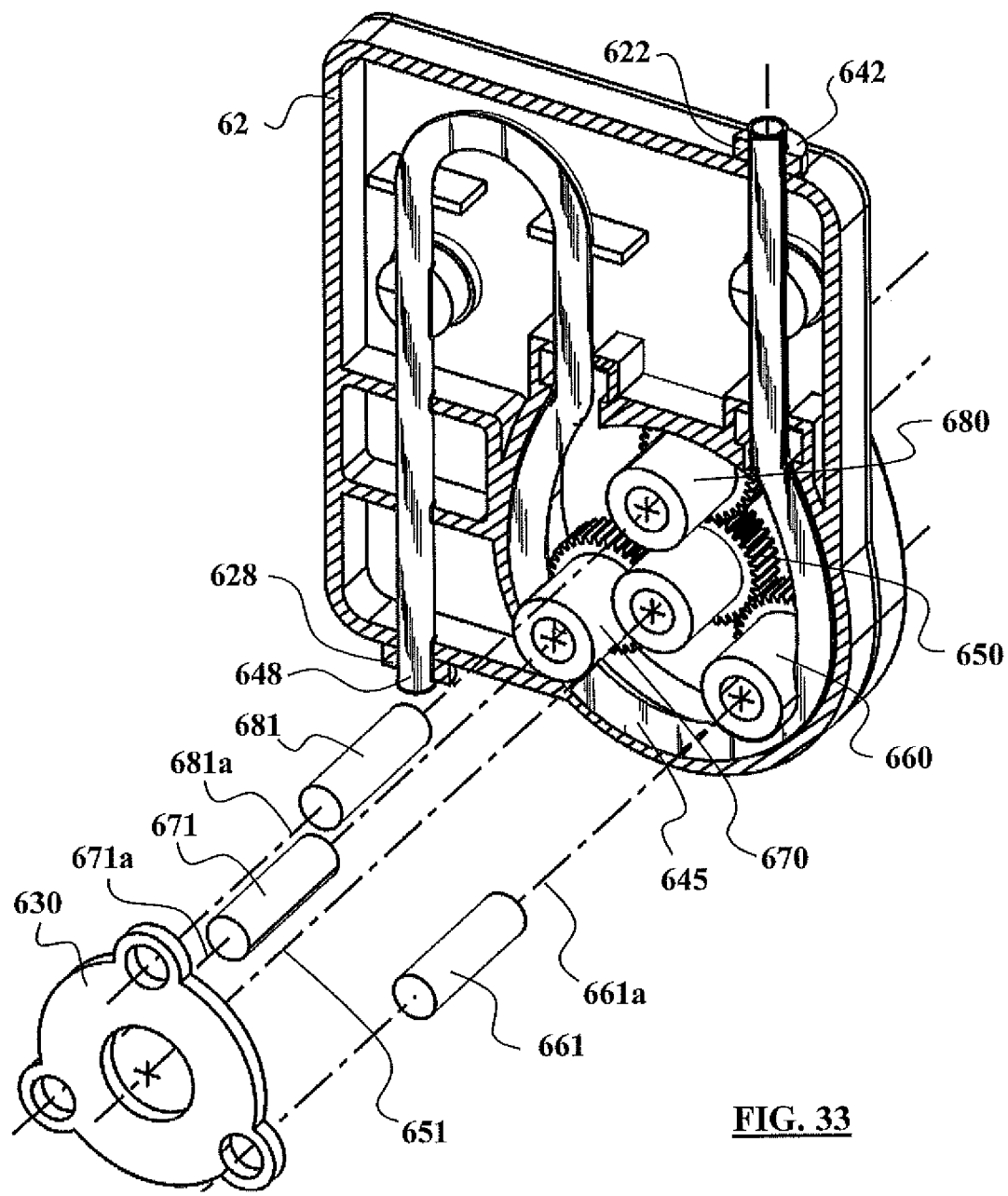
FIG. 33 is an exploded perspective view showing a housing, a tube and an actuator of the tube cassette shown in FIG. 28
Figure 34:
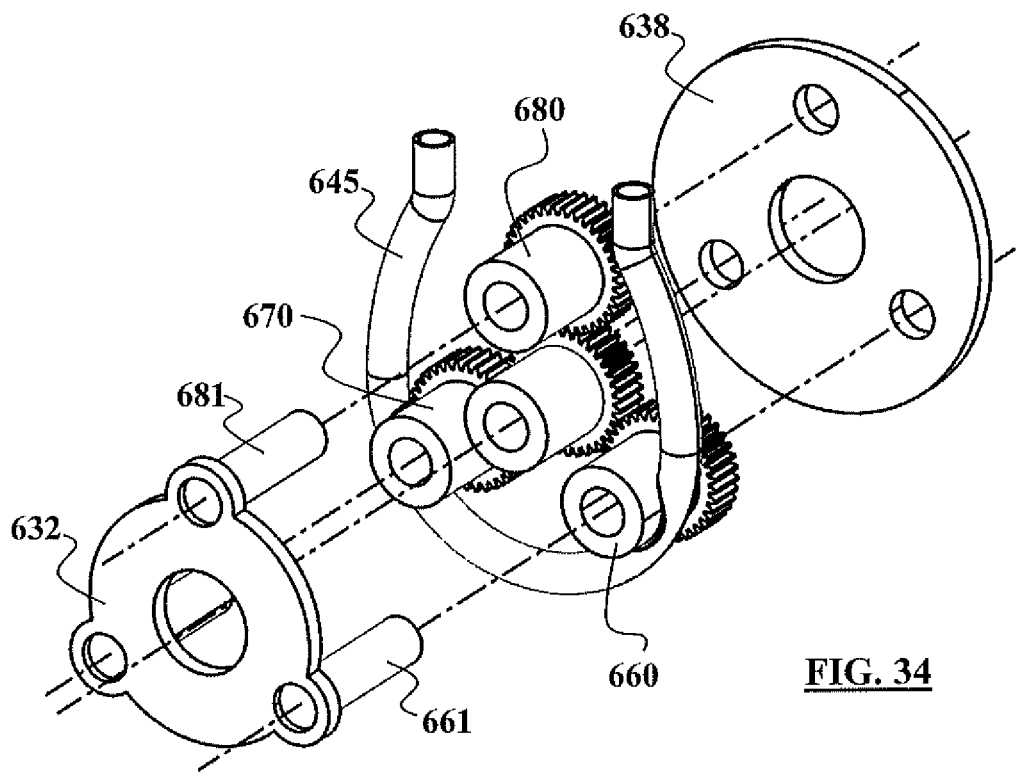
FIG. 34 is a perspective view of FIG. 33 omitting the housing.
Figure 35:
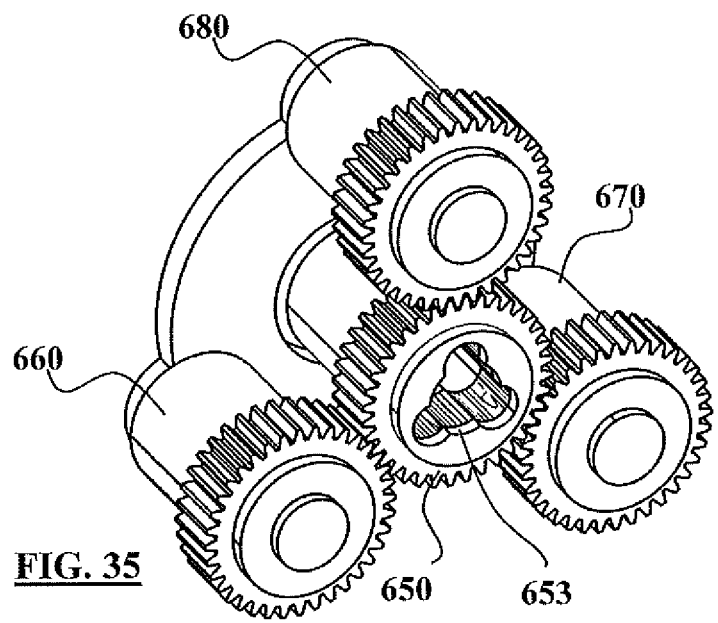
FIG. 35 is a perspective back view of the actuator shown in FIG. 33.

As shown in FIG. 27D, in the twenty-fifth menu 3606, a message of "Occlusion at Lower Tube, Check for Kinks, Yes=Infusion resumes with previous data, No=Infusion Aborted" is shown in the first column 3912 of the screen 1902; a message of "Resume INFUSION?" is shown in the second column 3914 of the screen 1902; a "Yes" indicator 3916a is shown at the lower part of the third column 3916 of the screen 1902 and pointing to the first (green) button 112; a "No" indicator 3916b is shown at the lower part of the third column 3916 of the screen 1902 and pointing to the second (red) button 114. The status is shown as "INFUSING" in the status bar 3918 displayed on the screen 1902.

If a user confirms not to resume infusion, the user presses the second (red) button 114 corresponding to the "No" indicator 3916b in the twenty-fifth menu 3606, the infusion pump aborts the infusion at block 4608.

If a user confirms to resume infusion, the user presses the first (green) button 112 corresponding to the "Yes" indicator 3916a in the twenty-fifth menu 3606, the infusion pump resumes the infusion with the previous data at block 4610.

Upon completion of infusion, the infusion pump proceeds with steps at block 4650 with respect to the completion of the infusion and the data storing. The steps at block 4650 are the same as the steps at block 4150.

According to a further aspect, the present invention provides a tube cassette for use with an infusion pump illustrated above, for fluid medicine infusion.

As shown in the drawings, FIGS. 28 to 43, in one embodiment, a tube cassette 600 comprises a housing 62, a fluid channel e.g. a tube 64 disposed in the housing 62, and an actuator 66 disposed in the housing 62 and engaged to the tube 64. The housing 62 has a first opening 622, a second opening 628, and a third opening 625 formed thereon. The first opening 622 may be formed at a top portion of the housing 62, the second opening 628 may be formed at a bottom portion of the housing 62, and the third opening 625 may be formed at a back wall 620b of the housing 62. The housing 62 defines an operation axis 625a passing through the third opening 625 and perpendicular to the back wall 620b. The housing 62 has a support wall 624 extending perpendicularly from the back wall 620b, positioned in the housing 62 and surrounding the third opening 625.

A barcode label 690 (FIG. 30) is attached to a back side of the housing 62. The barcode label 690 maybe embedded therein information of fluid delivery specification dedicated to the tube cassette. The fluid delivery specification may include a flow rate, a Volume-To-Be Infused (VTBI), a date, a time and a sequence ID under each of which the fluid delivery is to be carried out. The fluid delivery specification maybe programmed and encoded into the barcode label by a caregiver according to the prescription issued to a care receiver. A tube cassette with a barcode label attached thereto is prepared at the care giver's facilities, and sent to a care receiver. Upon the tuba cassette being loaded to an infusion pump at the care receiver's facilities, without the presence or supervision of the care giver, the infusion pump scans the barcode label to retrieve the fluid delivery specification from the barcode. The fluid delivery specification is then compared with the predetermined set of infusion parameters programmed and stored in the infusion pump and if matching, the infusion is allowed to be carried out. If unmatching, the infusion is prevented and the infusion pump prompts that an incorrect tube cassette loaded, and asking the care receiver to replace the tube cassette loaded, or to contact the care giver for advice.

The tube 64 has an inlet 642, an outlet 648 and a main body portion 645 between the inlet 642 and the outlet 648. The tube 64 is disposed in and attached to the housing 62 via supporting elements 629 such as support ribs, brackets or pucks, etc. formed integral to or coupled to the housing 62. The inlet 642 is attached to the housing 62 and passing through the first opening 622. The outlet 648 is attached to the housing 62 and passing through the second opening 628. The main body portion 645 is arranged surrounding the third opening 625 of the housing 62. The main body portion 645 has an outer edge 645a resting against the support wall 624, and an inner edge 645b forming an accommodating space 646 therebetween.

The actuator 66 includes three rollers 660, 670 and 680 movably coupled to the housing 62, three roller shafts 661, 671 and 681 each passing through a respective roller 660, 670 and 680, a driving member 650 rotatably engaged to the rollers 660, 670 and 680, a carrier 632 rotatably coupled to a front side of the rollers 660, 670 and 680 through the roller shafts 661, 671 and 681, respectively, and a back plate 638 coupled to a back side of the roller shafts 661, 671 and 681. The driving member 650 is rotatable relative to the housing 62 about a driving axis 651 passing through a geometric center of the driving member 650. The driving member 650 has a coupling hole 653 formed at the geometric center along the driving axis 651. The carrier 632 is rotatable relative to the housing 62 about the driving axis 651 and independent from the rotation of the driving member 650.

Figure 36:
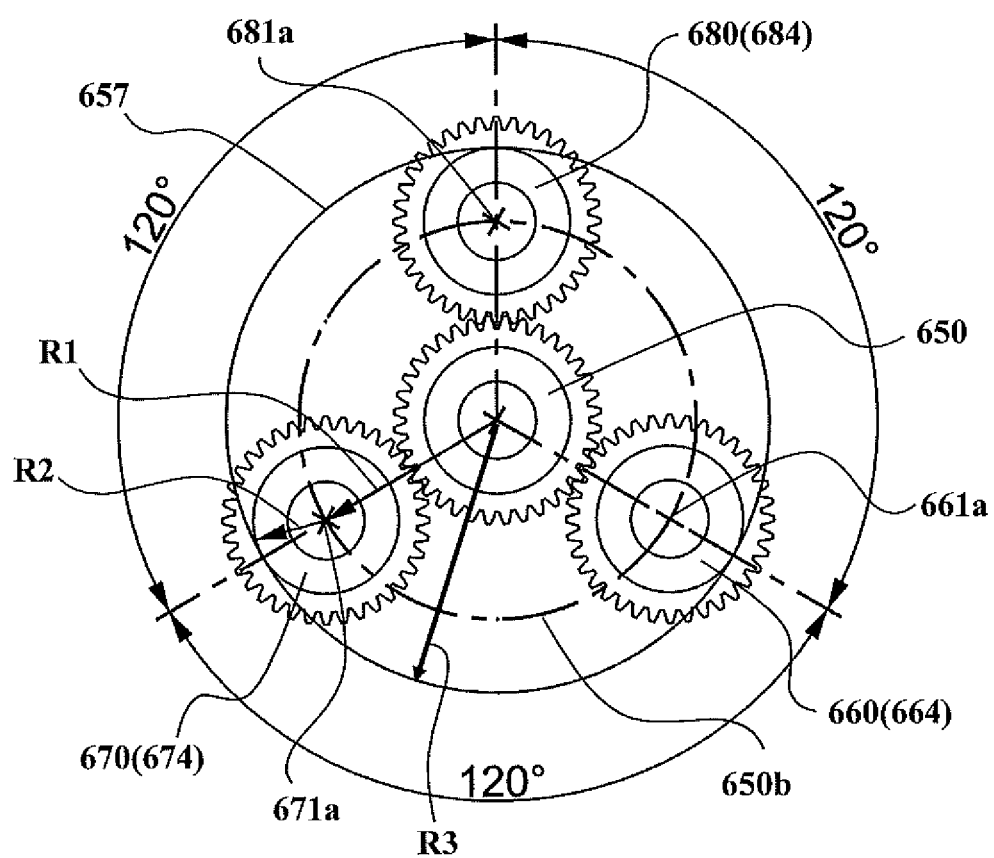
FIG. 36 is a schematic front view of FIG. 35.

The roller shafts 661, 671 and 681 are arranged parallel to the driving axis 651. Roller shafts 661, 671 and 681 each has a respective shaft axis 661a, 671a, 681a positioned offset with a first distance R1 along a radial direction from the driving axis 651. With a center located on the driving axis 651, R1 as the radius and oriented perpendicular to the driving axis 651 there is defined a distribution circle 6678 on which the shaft axle 661a, 671a and 681a are positioned and evenly arranged with the same angular pitch, i.e. a 120° angle therebetween (FIG. 36).

Rollers 660, 670 and 680 each has a cylinder 664, 674 and 684, and a follower gear 666, 676 and 686 coaxially integrated to the cylinder 664, 674 and 684, respectively. The cylinders 664, 674 and 684 are of the same shape and a same radius R2. The driving member 650 has a driving gear 656 meshed to the follower gears 666, 676 and 686, such that rotation of the driving member 650 about the center axis 651 causes the rollers 660, 670 and 680 to rotate about the respective roller axis 661a, 671a and 681a.

Figure 37:
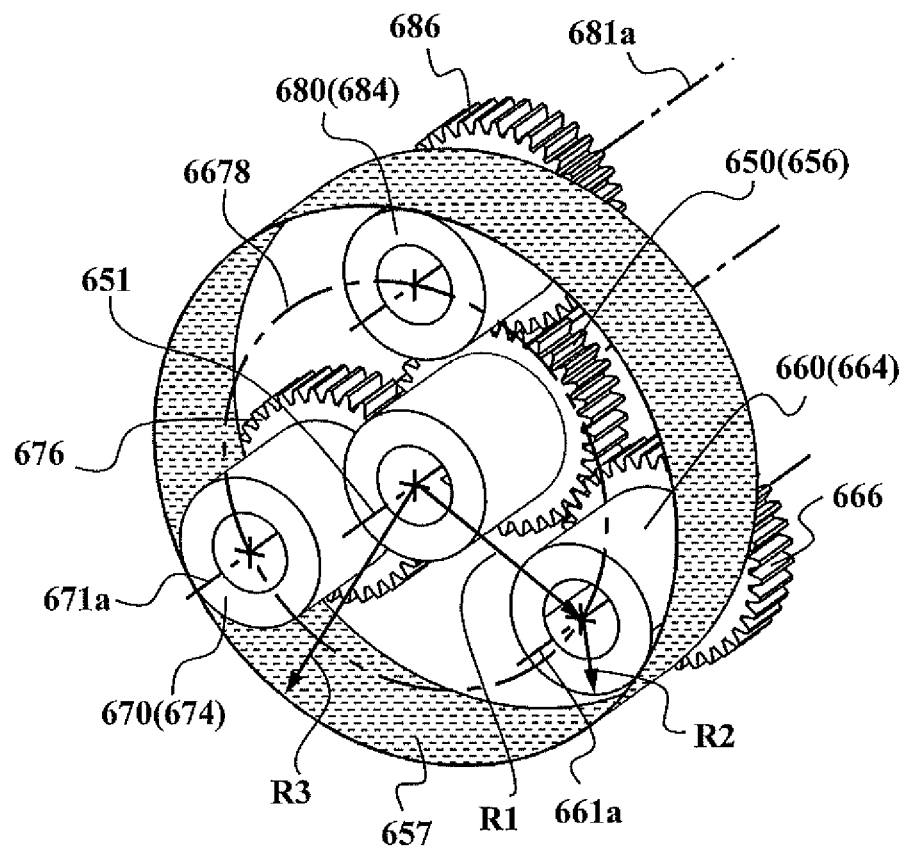
FIG. 37 is a perspective front view of FIG. 35 showing an envelope surface of the rollers.
Figure 38:
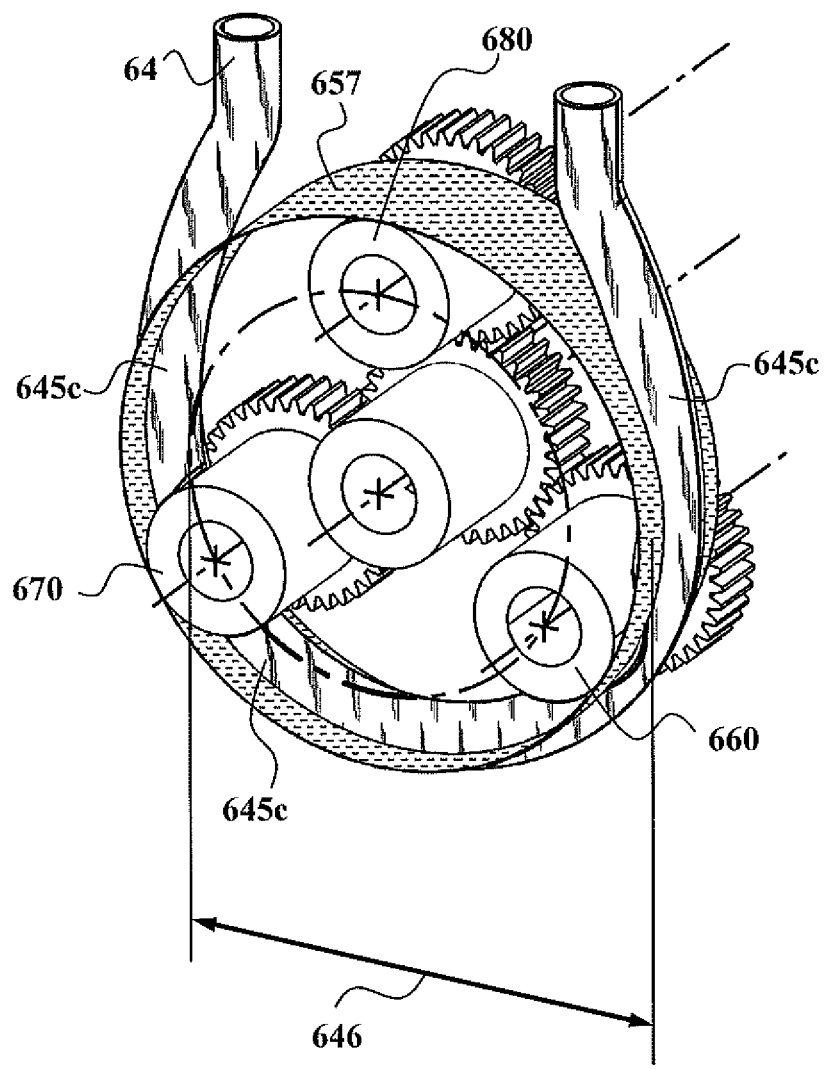
FIG. 38 is a perspective front view of FIG. 37 and a tube coupled to the actuator.

The carrier 632 is rotatably coupled to the housing 62, and rotatable relative to the housing 62 about the driving axis 651. The roller shafts 661, 671 and 681 are rotatable relative to the housing 62, by following the rotation of the carrier 632 about the driving axis 651. Additionally or independently, the rollers 660, 670 and 680 are rotatable relative to the carrier 632 about the respective roller shaft 661, 671 and 681. Accordingly, the rollers 660, 670 and 680 are movable within an envelope surface 657 tangential to the side surfaces of the cylinders 664, 674 and 684. The envelope surface 657 has a radius R3 which is the sum of the radius R1 of the distribution circle 6678 and the radius R2 of the roller 660, 670, 680, i.e. R3=R1+R2 (FIG. 37).

Figure 39:
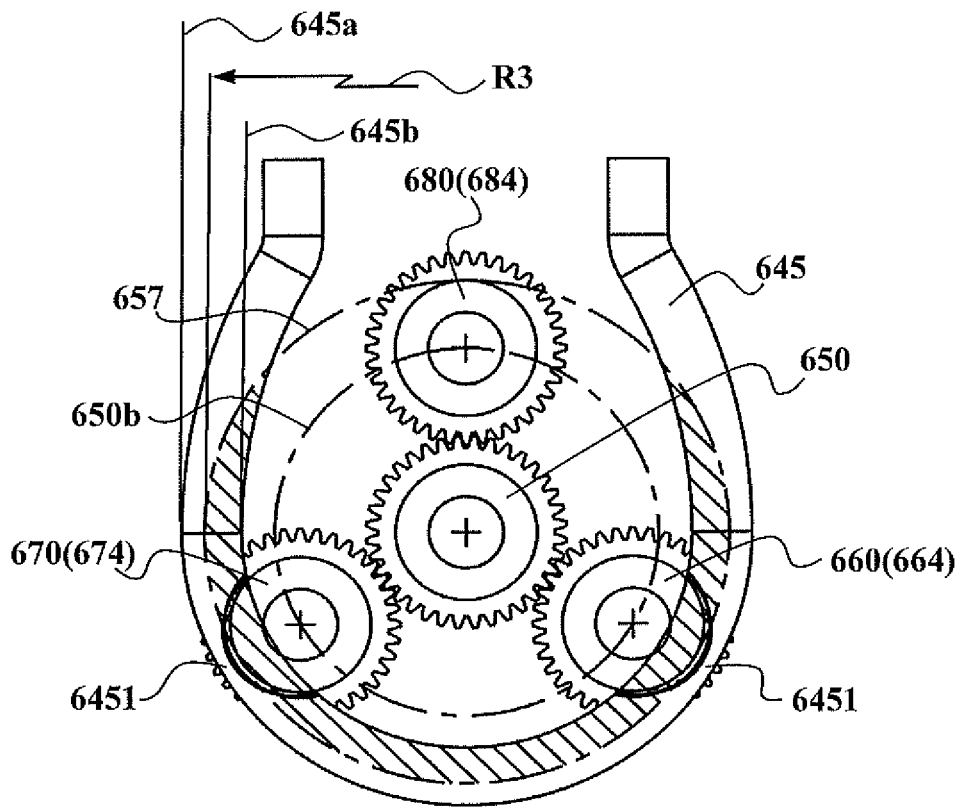
FIG. 39 is a schematic front view of FIG. 38.
Figure 40:
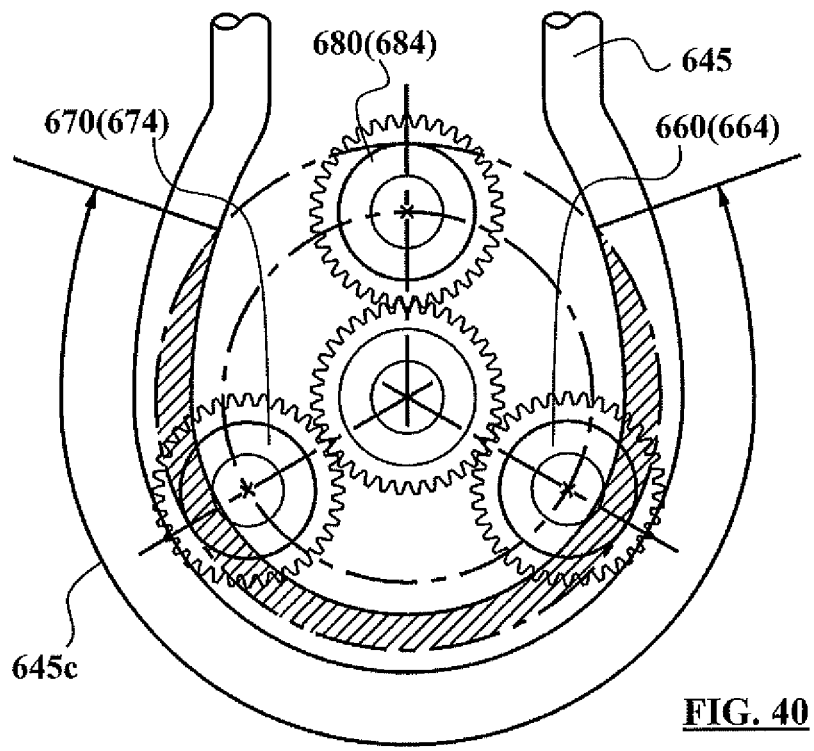
FIG. 40 is a schematic front view of FIG. 38 with further details indicated.

Upon the driving member 650 and the rollers 660, 670 and 680 being received in the accommodating space 646 (FIG. 38), the driving axis 651 is positioned concentric with the center axis 625a. The shapes and dimensions of the rollers 660, 670 and 680, the driving member 650 and the carrier 632 are so configured such that the envelope surface 657 is positioned between the outer edge 645a and the inner edge 645b of the main body portion 645 of the tube 64, i.e. R3 falls between the outer edge 645a and the inner edge 645b (FIG. 39). Accordingly, there is determined along the tube 64 an executing segment 645c to which the rollers 660, 670 and 680 maybe brought into engagement (FIG. 40).

Preferably, the main body portion 645 is arranged to have the executing segment 645c overlapping at least ⅔ of the full circular movement path of the rollers 660, 670 and 680. As such, at least two of the rollers 660, 670 and 680 may be brought into engagement with the executing segment 645c simultaneously at any instance during the circular movement of the rollers 660, 670 and 680.

Figure 41:
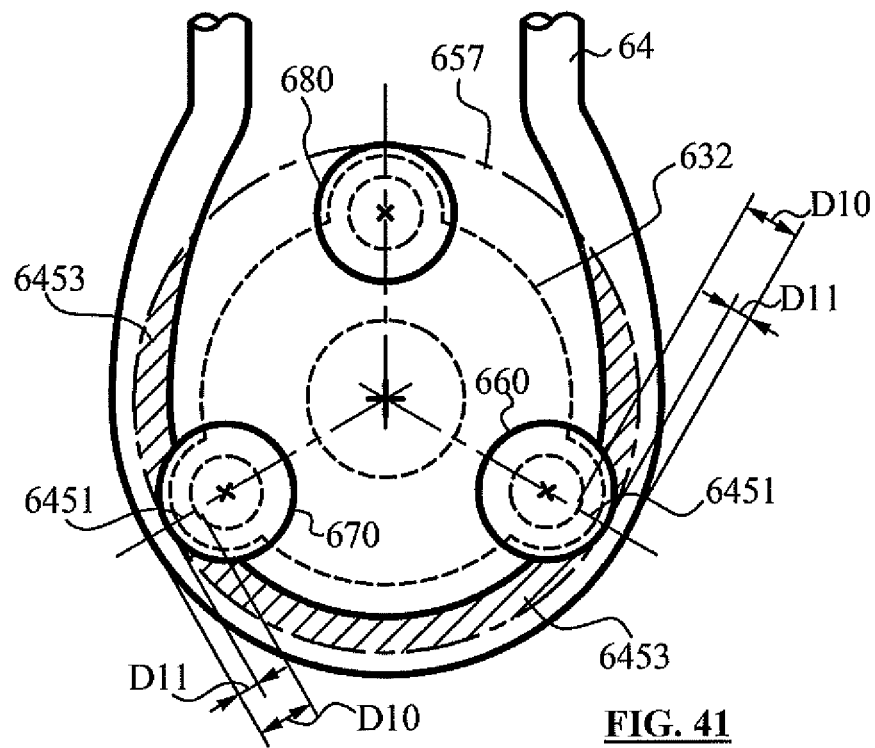
FIG. 41 is a schematic front view of FIG. 38 showing positions of the rollers at a first instance during an infusion process
Figure 42:
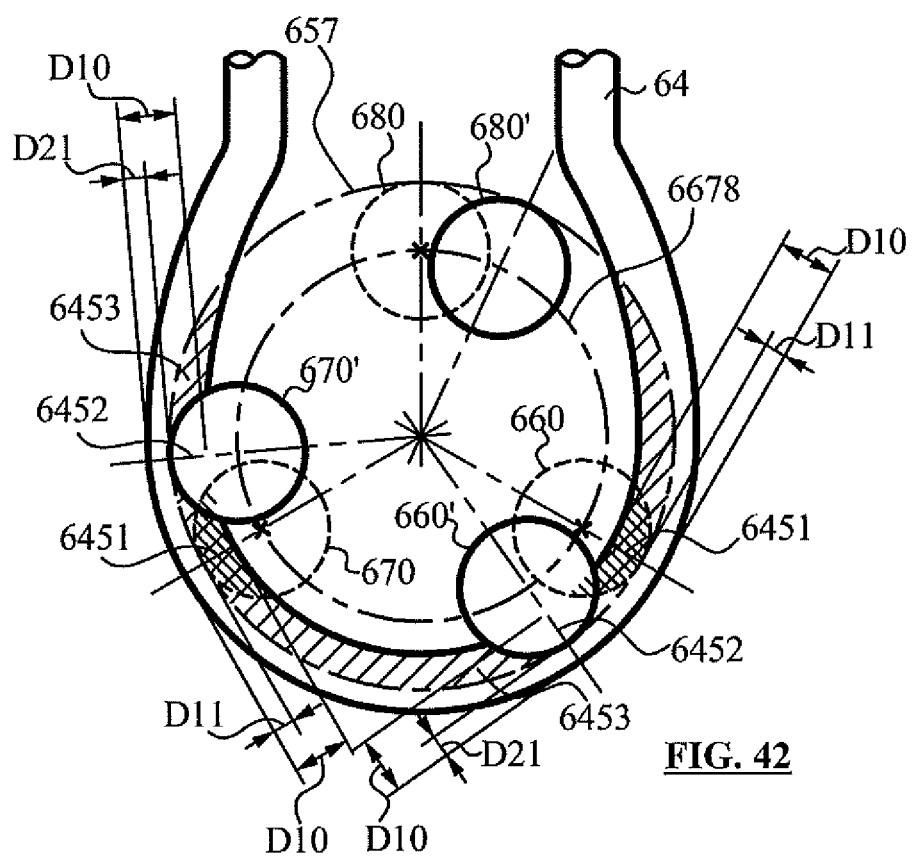
FIG. 42 is a schematic front view of FIG. 38 showing positions of the rollers at a second instance during an infusion process.
Figure 43:
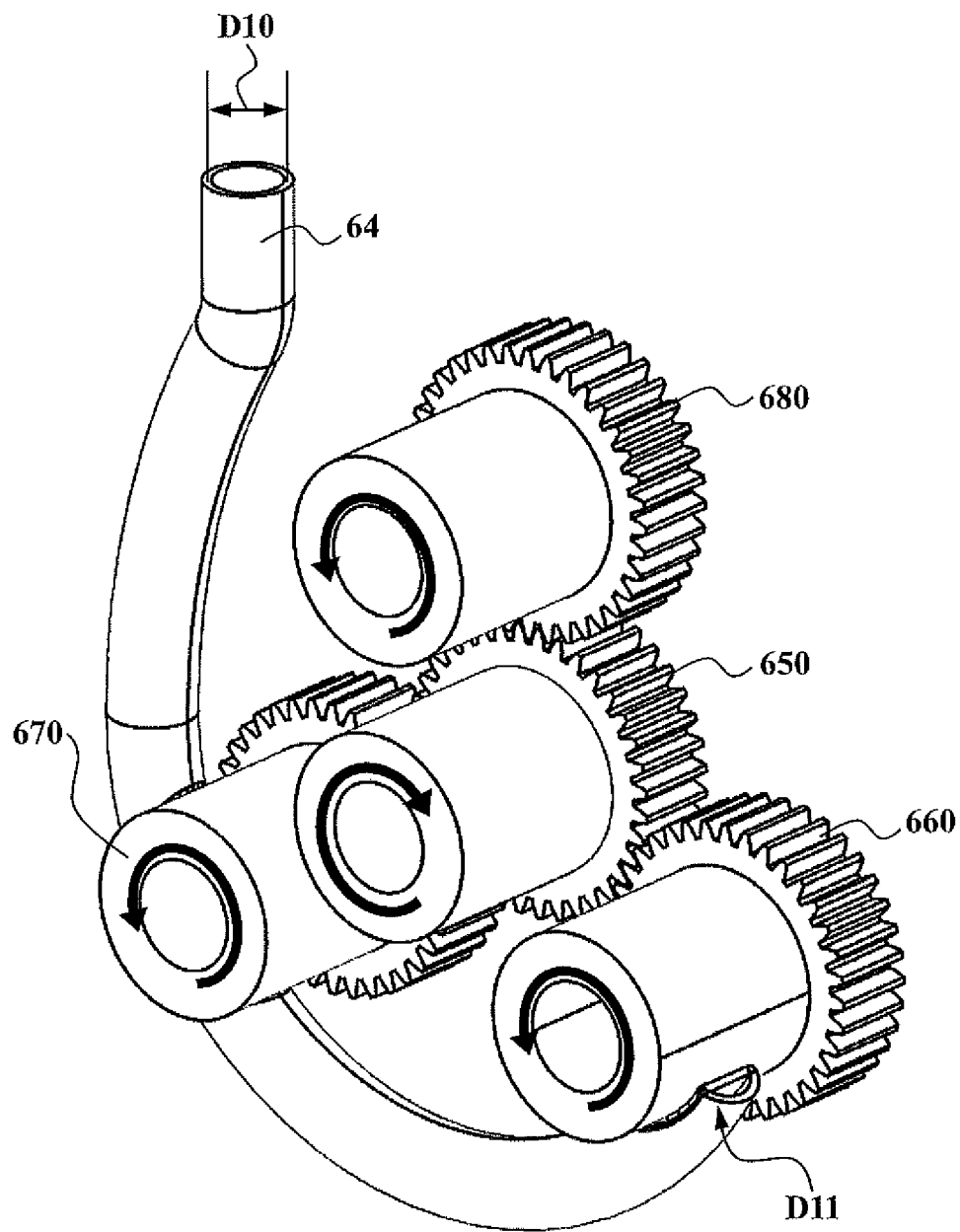
FIG. 43 is perspective partial view of FIG. 38.
Figure 44:
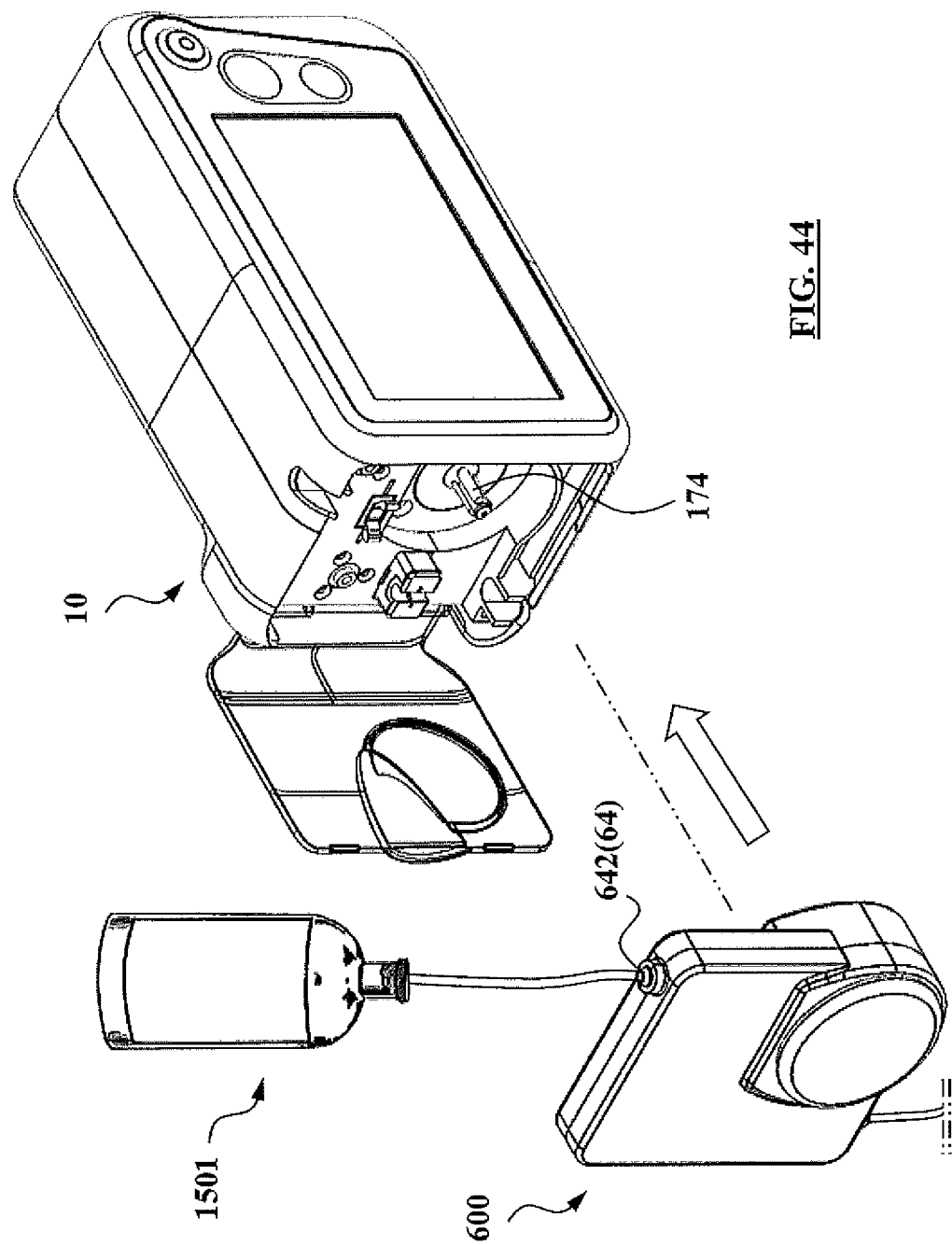
FIG. 44 is a partial exploded view showing a tube cassette of FIG. 28 to be loaded to an infusion pump.
Figure 45:
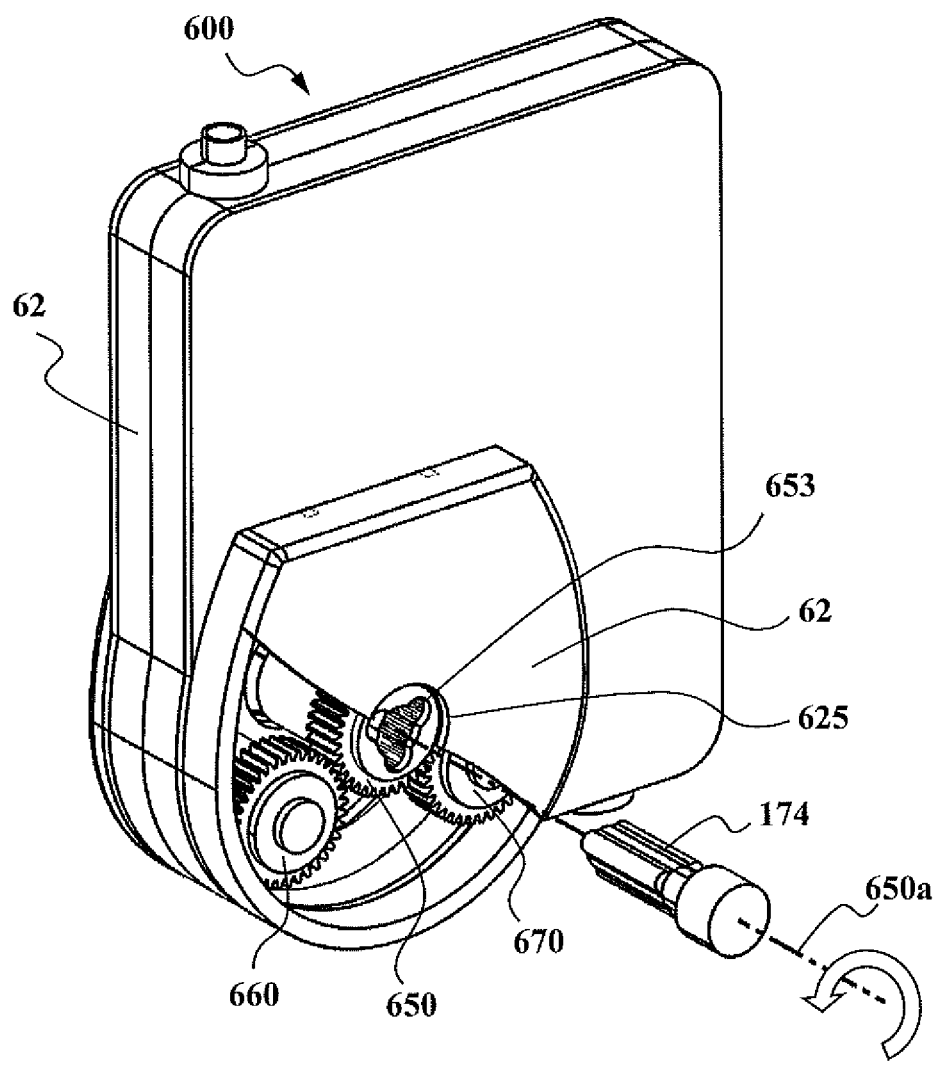
FIG. 45 is a partial cross sectional back view of FIG. 44.
Figure 46:
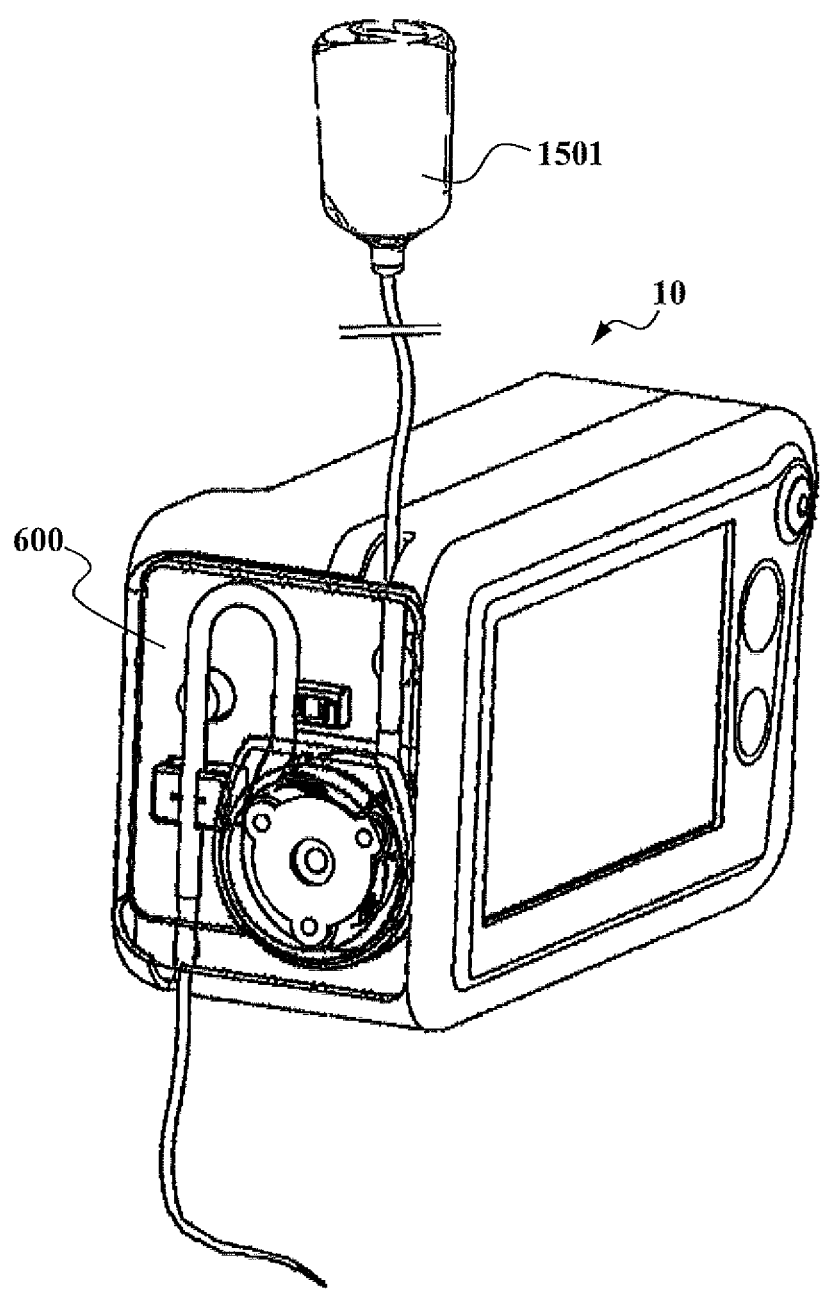
FIG. 46 is a perspective of FIG. 44 showing the tube cassette loaded to the infusion pump.
Figure 47:
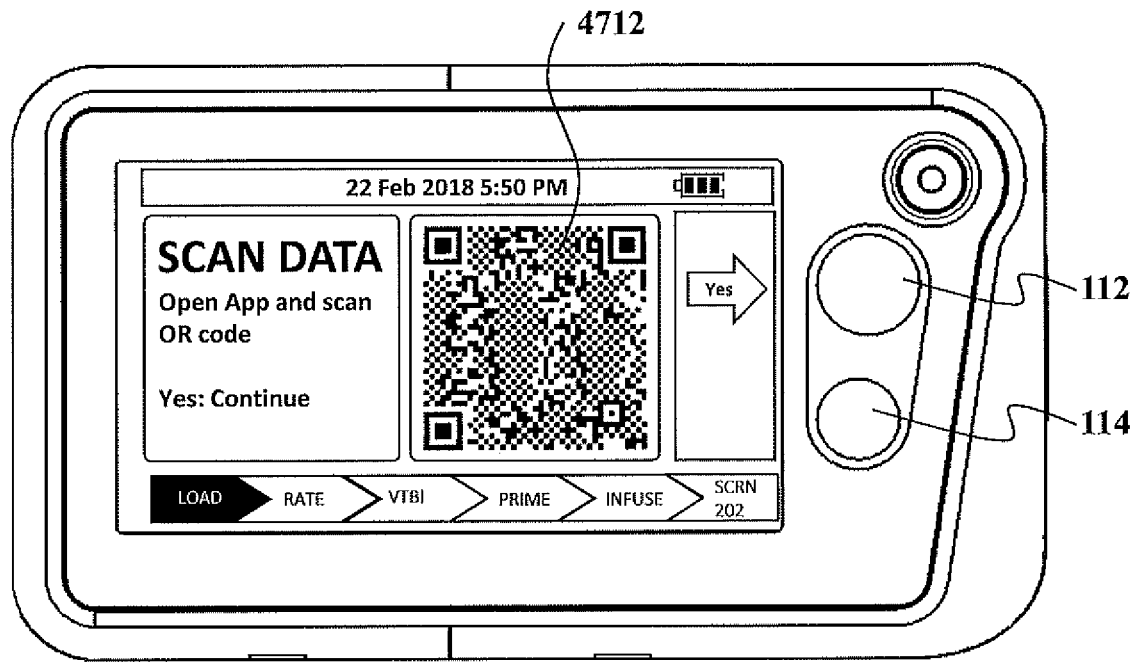
FIG. 47 is a schematic diagram showing a QR code displayed on a screen during control, configuration and operation of an infusion pump according to yet another embodiment.
Figure 48:
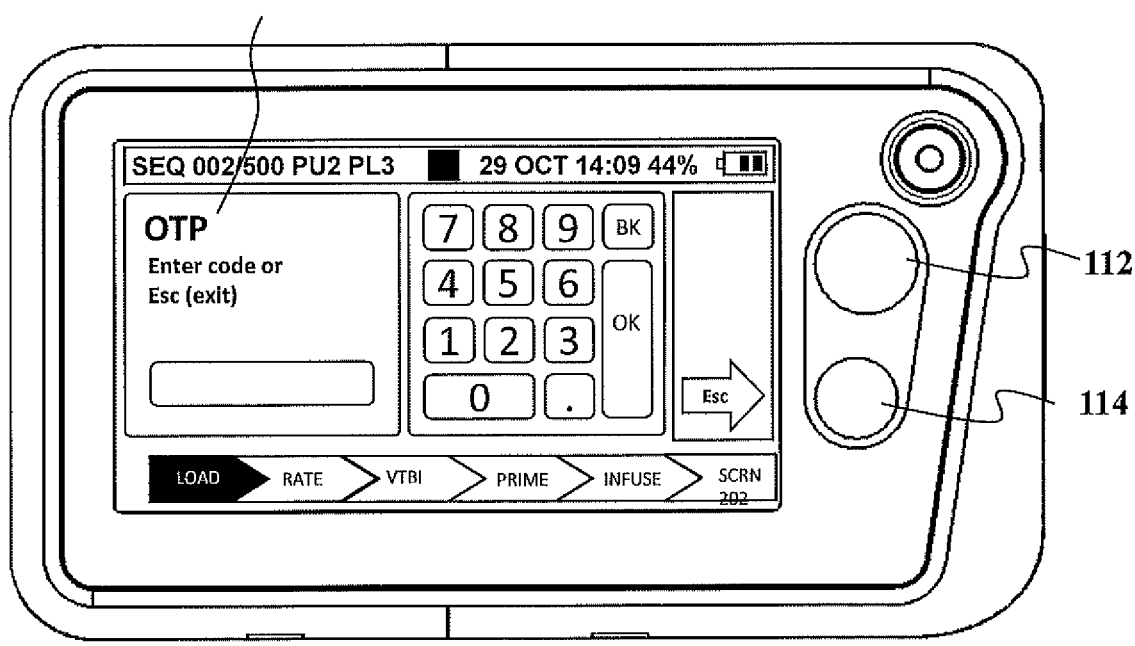
FIG. 48 is a schematic diagram showing password prompt displayed on a screen during control, configuration and operation of an infusion pump according to yet another embodiment.
Figure 49:
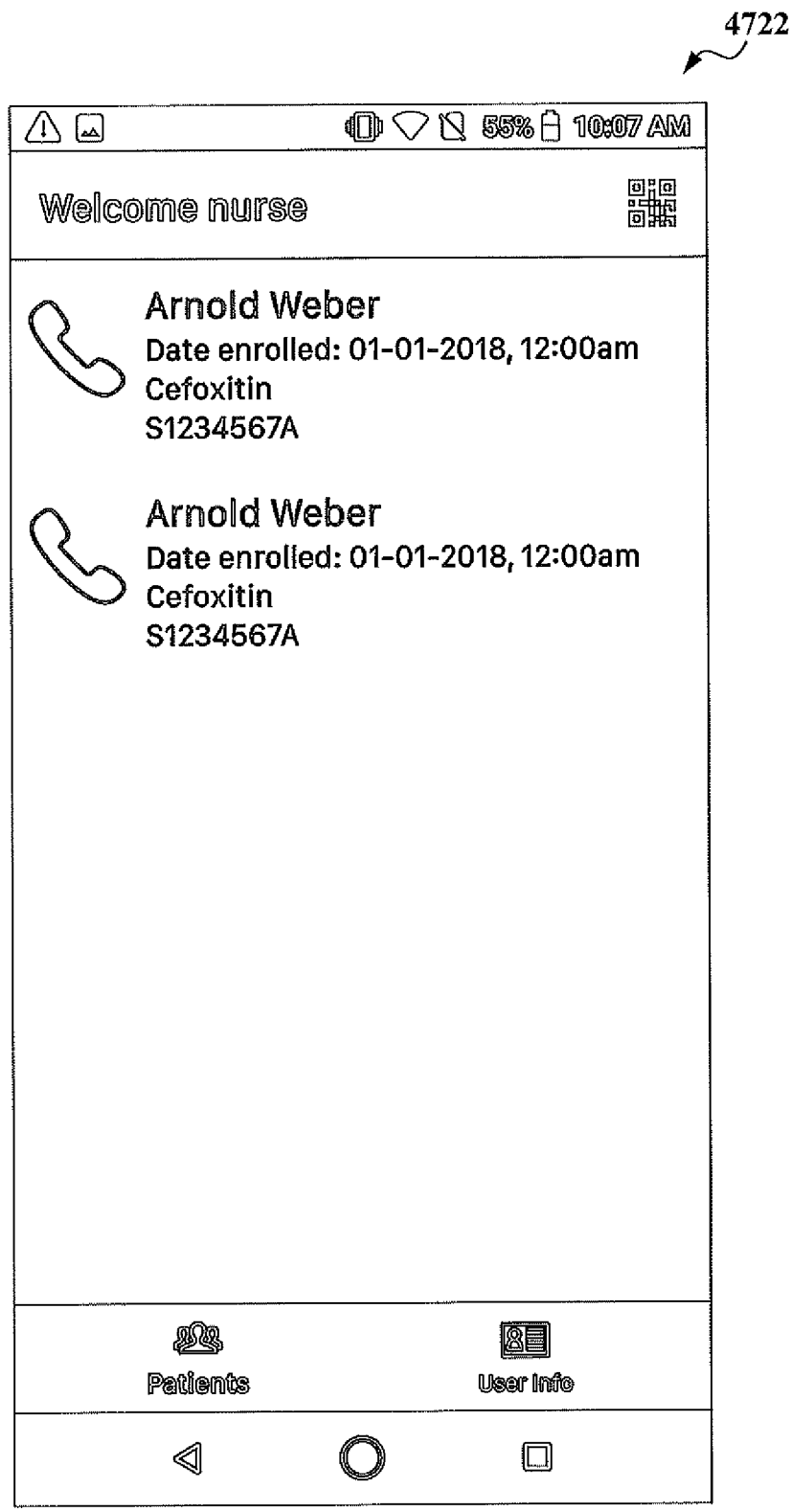
FIGS. 49 to 54 are schematic programs showing screen shots of an Apps used in line with an infusion pump according to still another embodiment.
Figure 50:
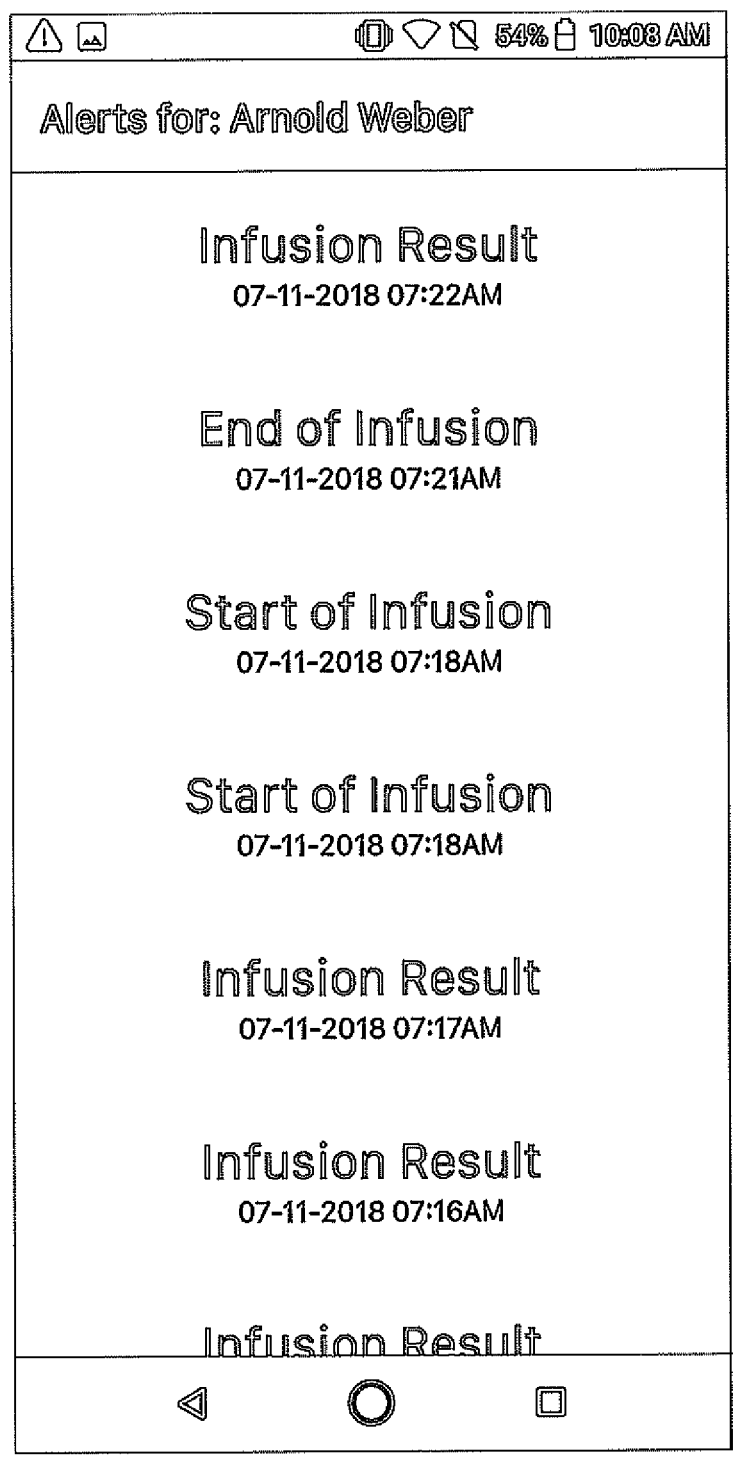
Figure 51:
Figure 52:
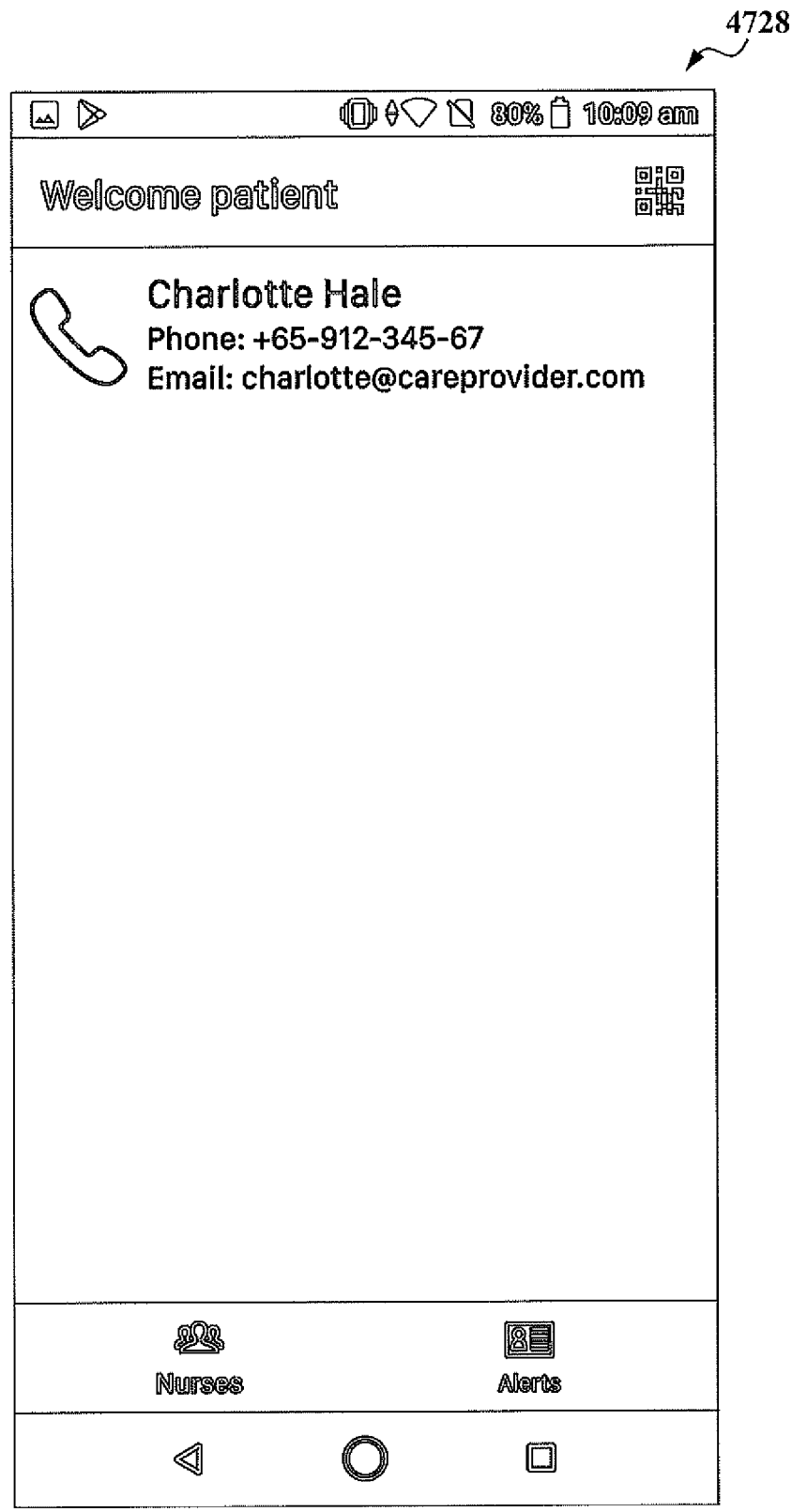
Figure 53:
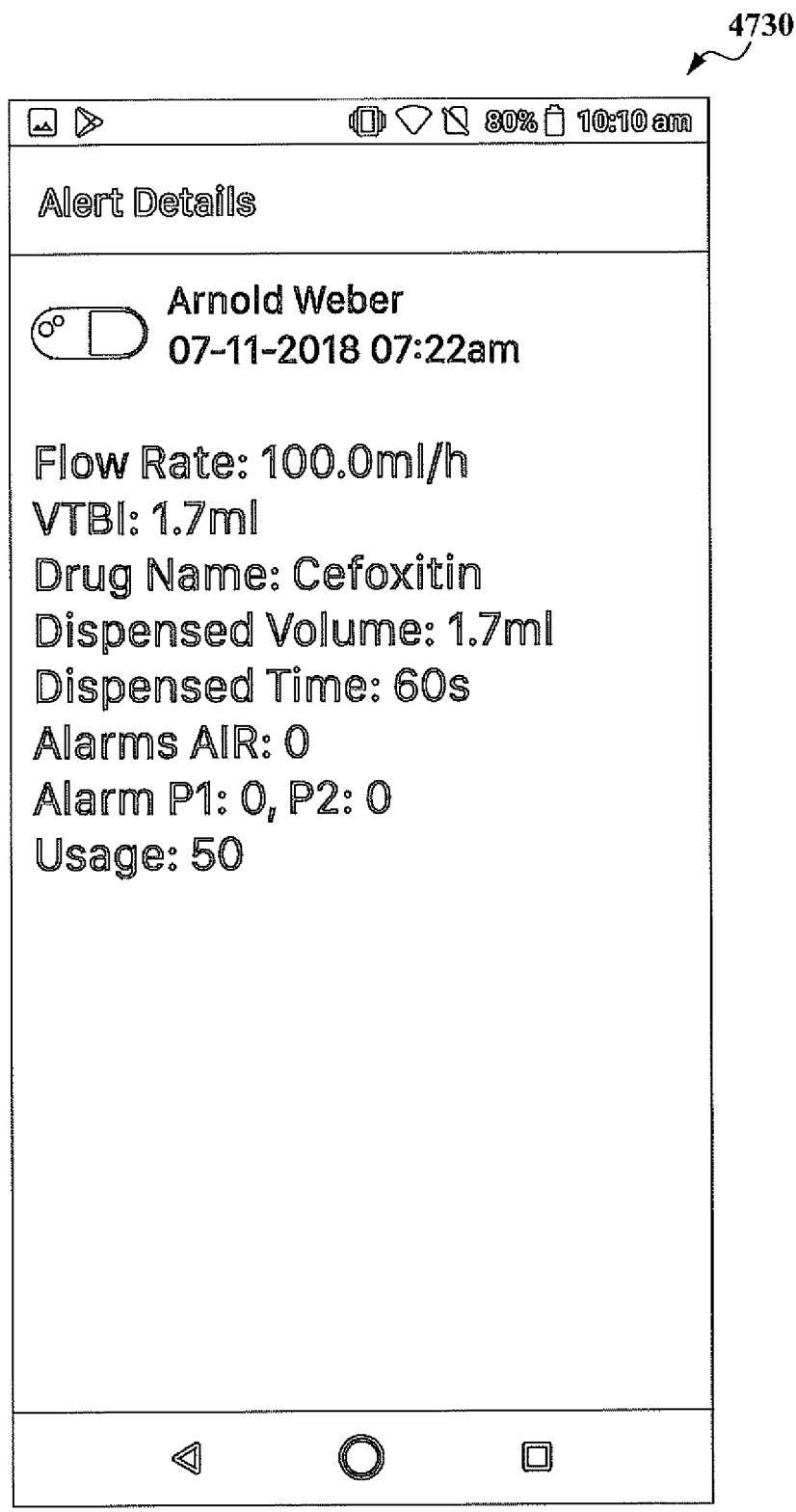
Figure 54:
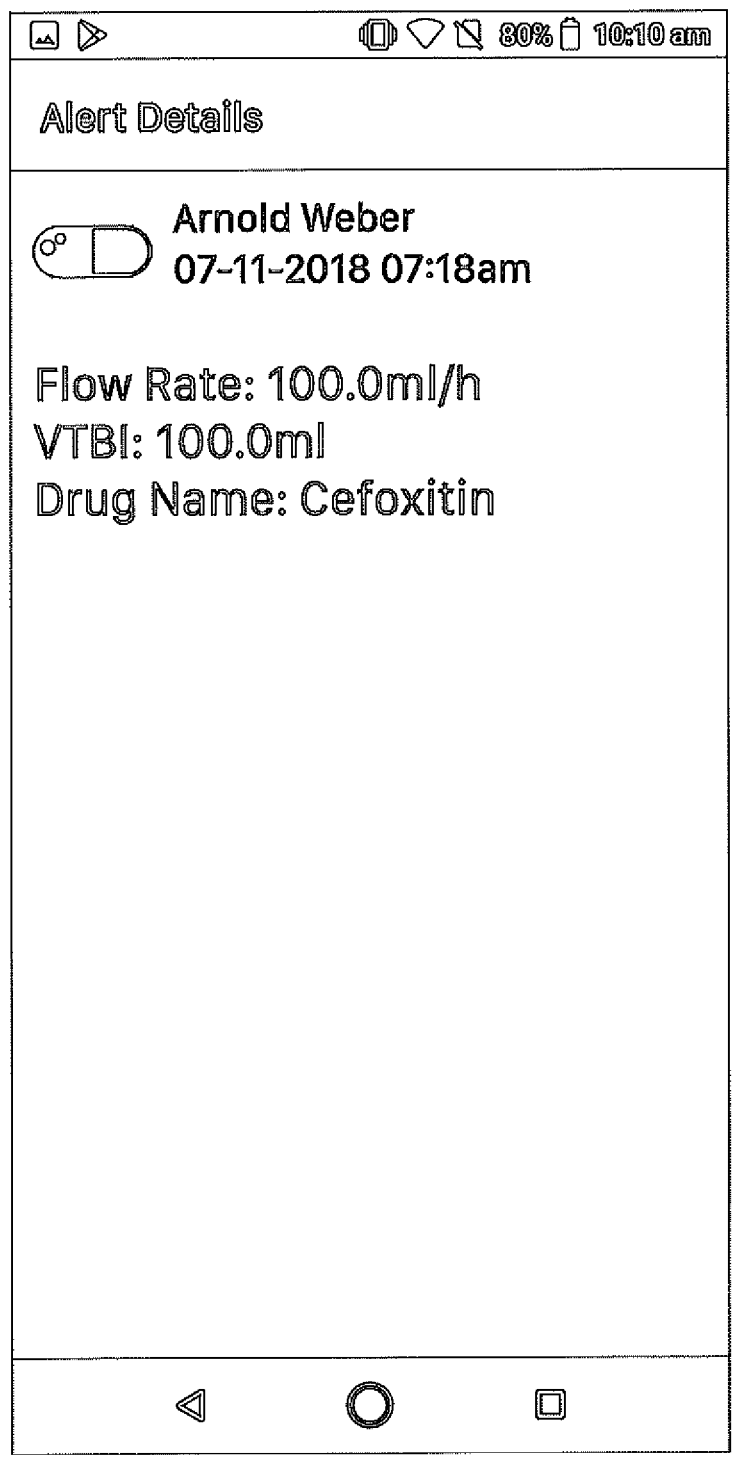

The tube 64 is made of an elastically deformable material such as silicon rubber. The rollers 660, 670 and 680 are made of relatively more rigid material such as PVC, which has a hardness greater than the tube 64. Accordingly, upon being brought into engagement with a first set of executing positions 6451 on the executing segment 645c, as shown in FIGS. 41, 42 and 43, the cylinders 664 and 674 of the respective rollers 660 and 670 squeeze the executing segment 645c to form a reduced cross section dimension D11 from an original cross section dimension D10, at each of the first set of executing positions 6451. Upon the rollers 660 and 670 moving away from the first set of executing positions 6451 to a second set of executing positions 6452 at a subsequent instance, the cross sections of the first set of executing positions 6451 resume to the original dimension D10, and the cross section of the subsequent set of executing positions 6452 becomes reduced to dimension D12 from the original dimension D10, as being deformed by the cylinders 664, 674 of the respective rollers 660, 670 (FIGS. 41 to 43).

In use, as shown in FIGS. 41 to 46, the tube cassette 600 with a fluid source 1501 connected to the inlet 642 of the tube 64 is loaded to a fluid pump 10, upon which, the driving member 650 is brought into engagement with the motor shaft 174 of the pump 10 via the coupling hole 653 of the driving member 650, through the third opening 625 of the housing 62.

Prior to an infusion operation, a prime process is carried out upon which the tube 64 of the tube cassette 600 is fully filled with the fluid medicine to be infused. The pump 10 then start an infusion operation by activating the motor shaft which causes the driving member 650 to rotate about the driving axis 650a. Following the motor shaft rotation, the driving member 650 causes the rollers 660, 670 and 680 to rotate about the respective roller axis 660a, 670a and 680a. As the first roller 660 and the second roller 670 are in contact with and engaged to the executing segment 645c of the tube 64, rotation of the first roller 660 and the second roller 670 about the respective roller axis 660a, 660b cause the first and the second rollers 660 and 670 to roll over on the surface of the executing segment 645c of the tube 64.

Connected to the carrier 632 through the roller shafts 661, and 671, movement of the first roller 660 and the second roller 670 rolling over on the surface of the executing segment 645c of the tube 64 causes the carrier 632 to rotate about the driving axis 651 and carry the third roller shaft 681 and the third roller 680 to move toward engagement with the executing segment 645c. As such, following the rotation of the motor shaft 174 of the pump 10, the rollers 660, 670 and 680 roll over on the tube 64 in an alternating, cyclic and continuous manner to deform a portion of the executing segment 645c.

As the curvature of the executing segment 645c is less than that of the external side surface of the cylinders 664, 674 and 684, there remains non-deformed portions 6453 on the executing segment 645c downstream each of the executing positions 6451. The movement of the cylinders 664 and 674 rolling over on the executing segment 645c from the first set of executing positions 6451 towards the second set of executing positions 6452 forces the fluid in the non-deformed portions 6453 to flow through the tube 64 toward the outlet 648 for infusion.

Working in the above-illustrated manner, the tube cassette 600 is operable to feed fluid medicine supplied to the tube 64 to a care receiver in an infusion operation, with a controlled flow rate which is configurable by an appropriate speed of the pump motor.

The tube cassette may be provided with indicators associated with usage status. The indicator may be configured to bear a first information corresponding to a situation where the tube cassette is one used the first time. Upon completion of the infusion, the first information is replaced by a second information corresponding to a situation where the tube cassette has been used. The indicators are readable by the infusion pump to determine whether a specific tube cassette loaded in the infusion pump is a first-time usage tube cassette or a re-used tube cassette. The infusion pump may be configured to reject a re-used tube cassette and prompt users to load a first-time usage tube cassette.

According to yet another embodiment, an infusion pump may be configured for using mobile Apps to scan information generated by the pump and communicating information to related parties e.g. nurses, care providers and insurance parties. The information may be one or more QR code displayed on the infusion pump screen, as that shown in FIGS. 47 to 54, together with Yes/No (Esc) buttons 112, 114 for controlling the operations of the infusion pump. The QR code 4712 may be shown when care givers' attention should be drawn during the infusion operation. For example, a QR code may be shown when an Alarm is activated, upon end of infusion, etc. Apps 4722 to 4732 (FIGS. 49 to 54) for mobile devices are also provided for scanning the QR code and providing follow up control functions. Additionally, One-Time-Password (OTP) 4714 may be provided such that upon the QR code being scanned, the OTP will be shown on the mobile device of a care giver or a nurse, for the purpose of checking and ensuring that the infusion pump will carry out infusion operation only a human check on the patient and medicine information are correct.

Figure 55:
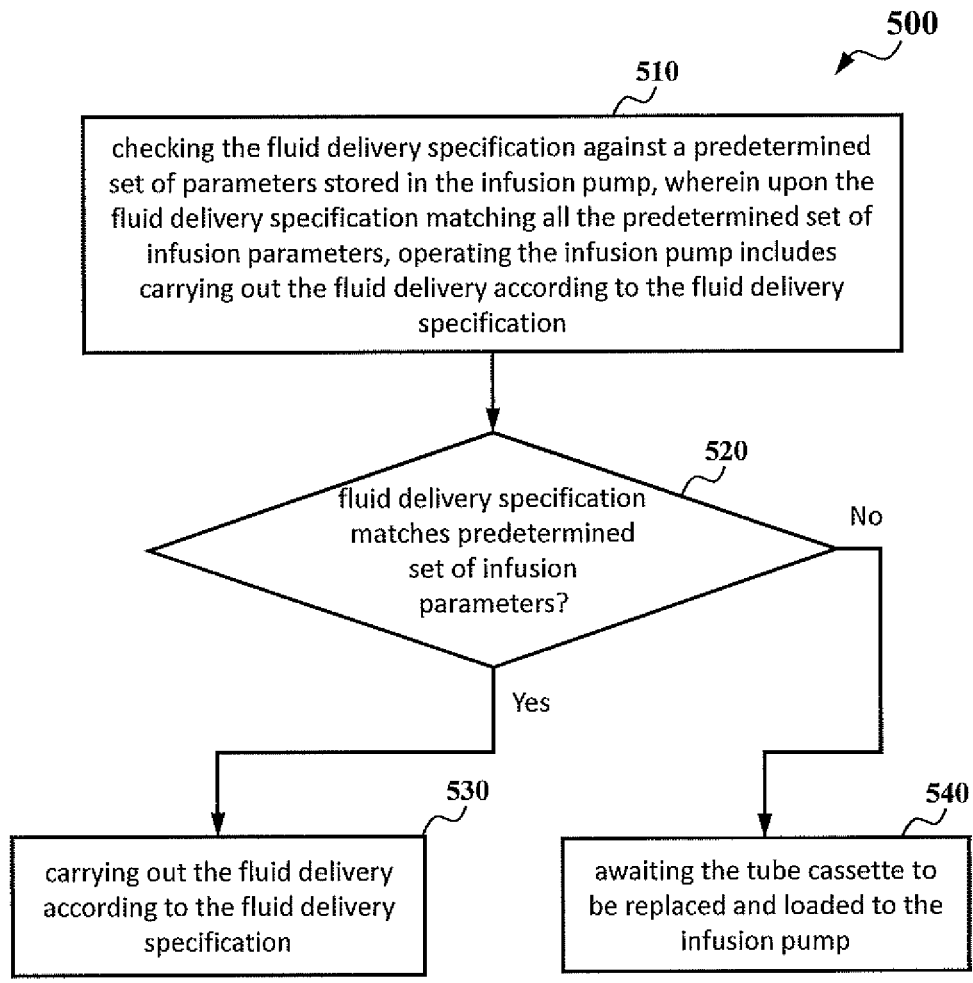
FIG. 55 is a flowchart showing a method of an infusion pump control according to a further embodiment.

In another embodiment, as shown in FIG. 55, a method 500 of infusion pump control further includes checking (block 510) the fluid delivery specification against a predetermined set of infusion parameters stored in the infusion pump, and determining whether the fluid delivery specification matches predetermined set of infusion parameters at block 520. Upon all the fluid delivery specification matches all the predetermined set of parameters, operating the infusion pump includes carrying out the fluid delivery (block 530) according to the fluid delivery specification. if at least one of the fluid delivery specification mismatches the predetermined set of parameters, operating the infusion pump includes awaiting the tube cassette to be replaced and loaded to the infusion pump (540).

As used herein, the singular "a" and "an" may be construed as including the plural "one or more" unless clearly indicated otherwise.

This disclosure has been presented for purposes of illustration and description but is not intended to be exhaustive or limiting. Many modifications and variations will be apparent to those of ordinary skill in the art. The example embodiments were chosen and described in order to explain principles and practical application, and to enable others of ordinary skill in the art to understand the disclosure for various embodiments with various modifications as are suited to the particular use contemplated.

Thus, although illustrative example embodiments have been described herein with reference to the accompanying figures, it is to be understood that this description is not limiting and that various other changes and modifications may be affected therein by one skilled in the art without departing from the scope or spirit of the disclosure.

The invention claimed is:

1. An infusion pump control method comprising:
   automatically downloading an information of a fluid delivery specification, including a flow rate under which the fluid delivery is to be carried out;
   displaying the information of the fluid delivery specification at a user interface of the infusion pump;
   after the displaying step, receiving a first response signal via the user interface, wherein the first response signal includes one of an affirmative indication of accepting the flow rate and a negative indication of rejecting the flow rate; and operating the infusion pump according to the first response signal,
wherein operating the infusion pump is allowed only after having received, via the user interface, the affirmative indication of accepting the flow rate displayed at the user interface, and wherein manual entry of the flow rate is disabled by the infusion pump at all times after the displaying step.

2. The method of claim 1, wherein upon the first response signal received being the affirmative indication, operating the infusion pump includes configuring the fluid delivery under the flow rate accepted.

3. The method of claim 2, wherein the fluid delivery specification includes a Volume-To-Be Infused (VTBI) under which the fluid delivery is to be carried out, the first response signal includes one of an affirmative indication of accepting the VTBI and a negative indication of revising the VTBI.

4. The method of claim 3, wherein upon the first response signal received being the affirmative indication, operating the infusion pump includes configuring the fluid delivery under the VTBI accepted.

5. The method of claim 4, further comprising displaying at the interface a request for a priming and receiving a second response signal via the user interface for the request, wherein the second response signal includes one of an affirmative indication of carrying out the priming and a negative indication of skipping the priming.

6. The method of claim 5, wherein upon the second response signal being the affirmative indication, operating the infusion pump includes carrying out the fluid delivery under the flow rate accepted and the VTBI accepted after the priming.

7. The method of claim 5, wherein upon the second response signal being the negative indication, operating the infusion pump includes carrying out the fluid delivery under the flow rate accepted and the VTBI accepted without the priming.

8. The method of claim 3, wherein upon the first response signal received being the negative indication, operating the infusion pump includes enabling input of a customized VTBI at the interface, and configuring the fluid delivery under the customized VTBI.

9. The method of claim 8, further comprising prompting at the interface a request for a priming and receiving a second response signal via the user interface for the request.

10. The method of claim 9, wherein the second response signal includes one of an affirmative indication of carrying out the priming and a negative indication of skipping the priming.

11. The method of claim 10, wherein upon the second response signal being the affirmative indication, operating the infusion pump includes carrying out the fluid delivery under the flow rate accepted and the customized VTBI after the priming.

12. The method of claim 10, wherein upon the second response signal being the negative indication, operating the infusion pump includes carrying out the fluid delivery under the flow rate accepted and the customized VTBI without the priming.

13. The method of claim 1, wherein upon the first response signal received being the negative indication, operating the infusion pump includes awaiting the tube cassette to be replaced and loaded to the infusion pump.

14. The method of claim 13, further comprising displaying at the user interface a notice of replacing the tube cassette.

15. The method of claim 1, further comprising checking the fluid delivery specification against a predetermined set of infusion parameters stored in the infusion pump, wherein upon the fluid delivery specification matching all the predetermined set of parameters, operating the infusion pump includes carrying out the fluid delivery according to the fluid delivery specification.

16. The method of claim 15, wherein the predetermined set of parameters include a flow rate, a Volume-To-Be Infused (VTBI), a date, a time and a sequence ID under each of which the fluid delivery is to be carried out.

17. The method of claim 16, wherein the predetermined set of parameters include a flow rate, a Volume-To-Be Infused (VTBI), a date, a time and a sequence ID under each of which the fluid delivery is to be carried out.

18. The method of claim 1, further comprising checking the fluid delivery specification against a predetermined set of infusion parameters stored in the infusion pump, wherein upon the fluid delivery specification mismatching at least one of the predetermined set of parameters, operating the infusion pump includes awaiting the tube cassette to be replaced and loaded to the infusion pump.

19. The method of claim 1, wherein the automatically downloading step comprises obtaining the information of the fluid delivery specification from a tube cassette loaded to the infusion pump.

20. The method of claim 19, wherein the step of obtaining an information of a fluid delivery specification from a tube cassette comprises scanning an optical label borne on the tube cassette, wherein the optical label is embedded with a code corresponding to the fluid delivery specification.

* * * * *